United States Patent
Cezar

(10) Patent No.: US 8,703,483 B2
(45) Date of Patent: Apr. 22, 2014

(54) REAGENTS AND METHODS FOR USING HUMAN EMBRYONIC STEM CELLS TO EVALUATE TOXICITY OF PHARMACEUTICAL COMPOUNDS AND OTHER CHEMICALS

(75) Inventor: Gabriela G. Cezar, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1238 days.

(21) Appl. No.: 11/733,677

(22) Filed: Apr. 10, 2007

(65) Prior Publication Data

US 2007/0248947 A1    Oct. 25, 2007

Related U.S. Application Data

(60) Provisional application No. 60/790,647, filed on Apr. 10, 2006, provisional application No. 60/822,163, filed on Aug. 11, 2006.

(51) Int. Cl.
*C12N 5/00* (2006.01)
(52) U.S. Cl.
USPC .......................... 435/325; 435/366; 435/375
(58) Field of Classification Search
USPC ........................................ 435/325, 366, 375
See application file for complete search history.

(56) References Cited

U.S. PATENT DOCUMENTS

| | | | |
|---|---|---|---|
| 6,197,575 | B1 | 3/2001 | Griffith et al. |
| 6,200,806 | B1 | 3/2001 | Thomson |
| 2002/0019023 | A1 | 2/2002 | Dasseux et al. |
| 2003/0219866 | A1 | 11/2003 | Kruijer et al. |
| 2004/0073958 | A1 | 4/2004 | Katsuki et al. |
| 2004/0121305 | A1 | 6/2004 | Wiegand et al. |

FOREIGN PATENT DOCUMENTS

| | | |
|---|---|---|
| CA | 2560334 | 10/2005 |
| EP | 0937779 | 8/1999 |
| WO | 0194616 | 12/2001 |
| WO | 03005628 | 1/2003 |
| WO | 03/018760 A2 | 3/2003 |
| WO | 03089635 | 10/2003 |
| WO | 2004/065616 A2 | 8/2004 |
| WO | 2005005162 | 1/2005 |
| WO | 2005005621 | 1/2005 |
| WO | 2005080551 | 9/2005 |

OTHER PUBLICATIONS

Meisel et al. "Human bone marrow stronal cells inhibit allogeneic T-cell responses by indoleamine 2,3-dioxygenase-mediated tryptophan degradation", Immunobiology, 2004, 103(12):4619-4621.*

Zhang et al. "Mass spectral evidence for carbonate-anion-radical-induced posttranslational modification of tryptophan to kynurenine in human Cu, Zn superoxide dismutase", Free Radical Biology & Medicine, 2004, 2018-2026.*

Trosko, J.E., "Use of human embryonic and adult stem cells for drug screening and safety assessment," Toxicology, Sep. 1, 2006, 226:31.

John C. Lindon et al., "Contemporary issues in toxicology the role metabonomics in toxicology and its evaluation by the COMET project," Toxicology and Applied Pharmacology, Mar. 15, 2003 187:3 137-146.

Derek J. Crockford et al., "Statistical Heterospectroscopy, an Approach to the Integrated Analysis of NMR and UPLC-MS Data Sets: Application in Metabonomic Toxicology Studies," Analytical Chemistry, Jan. 15, 2006, 78:2 363-361.

Lance Hareng et al., "The Integrated Project ReProTect: A novel approach in reproductive toxicity hazard assessment," Reproductive Toxicology, Sep. 2005, 20:3 441-452.

John McNeish, "Embryonic Stem Cells in Drug Discovery," Nature Reviews Drug Discovery, 2004 3:1 70-80.

Mark A Viant et al., "NMR-derived developmental metabolic trajectories: an approach for visualizing the toxic actions of trichloroethylene during embryogenesis," Metabolomics, Apr. 2005 1:2 149-158.

Adab et al., "The longer term outcome of children born to mothers with epilepsy," 2004, J Neurol Neurosurg Psychiatry 75:1575-83.

Beckman & Brent, "Mechanism of Teratogenesis," 1984, Annu Rev Pharmacol 24:483-500.

Bjerkedal et al., "Valproic Acid and Spina Bifida," 1982, Lancet 2:1096.

Brent & Beckman, "Enviromental Teratogens," Mar.-Apr. 1990, Bull NY Acad Med 66:123-63.

Capuron et al., "Interferon-Alpha-Induced Changes in Tyrptophan Metabolism: Relationship to Depression and Paroxetine Treatment," 2003, Biol Psychiatry 54:906-14.

Chiarugui et al., "Similarities and differences in the neuronal death processes activated by 3OH-kynurenine and quinolinic acid," 2001, J Neurochem 77:1310-8.

Chugani, "Serotonin in Autism and Pediatric Epilepsies," 2004, Ment Retard Dev Disabil Res Rev 10:112-116.

Claudio et al., "NIEHS Investigates Links between Children, the Environment, and Neurotoxicity," Jun. 2001, Environm Health Perspect 109(6):A254-A261.

Daston & Naciff, "Gene expression changes related to growth and differentiation in the fetal and juvenile reproductive system of the female rat: evaluation of microarray results," 2005, Reprod Toxicology 19:381-94.

Enviromental Protective Agency (EPA), "What Do We Really Know About the Safety of High Production Volume Chemicals," 1998, Chemical Hazard Data Availability Study, Office of Pollution Prevention and Toxins.

Fella et al., "Use of two-dimensional gel electrophoresis in predictive toxicology: Identification of potential early protein biomarkers in chemically induced hepatocarcinogenesis," 2005, Protemics 5:1914-21.

(Continued)

*Primary Examiner* — Bin Shen
(74) *Attorney, Agent, or Firm* — McDonnell Boehnen Hulbert & Berghoff LLP

(57) ABSTRACT

The invention provides biomarker profiles of cellular metabolites and methods for screening chemical compounds including pharmaceutical agents, lead and candidate drug compounds and other chemicals using human embryonic stem cells (hESC) or lineage-specific cells produced therefrom. The inventive methods are useful for testing toxicity, particularly developmental toxicity and detecting teratogenic effects of such chemical compounds.

48 Claims, 13 Drawing Sheets

(56) References Cited

OTHER PUBLICATIONS

Franks et al., "Thalidomide," 2004, Lancet 363:1802-11.
General Accounting Office (GAO), "Toxic Substances Control Act: Preliminary Observations on Legislative Changes to Make TSCA More Effective," 1994, Testimony Jul. 13, 1994, GAO/T-RCED-94-263.
Greaves et al., "First Does of Potential New Medicines to Humans: How Animals Help," 2004, Nat Rev Drug Discov 3:226-36.
Groenen et al., "High-resolution $^1$H NMR spectroscopy of amniotic fluids from spina bifida fetuses and controls," 2004, Eur J Obstet Gynecol Reprod Biol.;112:16-23.
Guillemin et al., "Quinolinic acid selectively induces apoptosis of human astrocytes: potential role in AIDS dementia complex," 2005, J Neuroinflammation 2:16.
He et al., "Human Embryonic Stem Cells Develop Into Multiple Types of Cardiac Myocytes," 2003, Circ Res 93:32-9.
Huuskonen, "New models and molecular markers in evaluation of developmental toxicity," 2005, Toxicology & Applied Pharm 207: S495-S500.
Kocki et al., "Enhancement of brain kynurenic acid production by anticonsulvants—Novel mechanism of antiepileptic activity," 2006, Eur J Pharmacol 542:147-51.
Kohl et al., "Measurement of tryptophan, kynurenine and neopterin in women with and without postpartum blues," 2005, J Affect Disord 86:135-42.
Levenstein et al.,"Basic Fibroblast Growth Factor Support of Human Embryonic Stem Cell Self Renewal," 2005, Stem Cells 24:568-574.
Li et al., "Targeted Mutation of the DNA Methyltransferase Gene Results in Embryonic Lethality," 1992, Cell 69:915-26.
Li et al., "Expansion of Human Embryonic Stem Cells in Defined Serum-Free Medium Devoid of Animal-Derived Products," 2005, Biotechnol Bioeng 91:688-698.
Livak & Schmittgen, "Analysis of Relative Gene Expression Data Using Real-Time Quantitative PCR and the 2-ΔΔCT Method," 2001, Methods 25:402-8.
Ludwig et al., "Feeder-independent culture of human embryonic stem cells," 2006, Nat Methods 3: 637-46.
Meador et al., "In utero antiepileptic drug exposure," 2006, Neurology 67:407-412.
Miller et al, "Upregulation of the initiating step of the kynurenine pathway in postmortem anterior cingulate cortex from individuals with schizophrenia and bipolar disorder," 2006, Brain Res 16:25-37.
Miyazaki et al., "Maternal administration of thalidomide or valproic acid causes abnormal serotonergic neurons in the offspring: implication for pathogenesis of autism ," 2005 Int J Devl Neuroscience 23:287-97.
Napierala et al, "Mutations and promoter SNPs in RUNX2, a transcriptional regulator of bone formation," 2005, Mol Genet Metab 86:257-68.
Narita et al., "Increased Monamine Concentration in the Brain and Blood of Fetal Thalidomide- and Valproic Acid-Exposed Rat: Putative Animal Models for Autism," 2000, Pediatric Res 52:576-79.
Nemeth et al., "Role of Kynurenines in the Central and Peripherial Nervous Systems," 2005, Curr Neurovasc Res 2:249-60.
Okada et al., "Polycomb Homologs Are Involved in Teratogenicity Valproic Acid in Mice," 2004, Birth Defects Res A Clin Mol Teratol 70:870-879.
Ornoy et al., "Fetal effects of primary and secondary cytomegalovirus infection in pregnancy," 2006, Reproductive Toxicol 21:399-409.
Perkins and Stone, "An iontophoretic investigation of the actions of convulsant kynurenines and their interaction with the endogenous excitant quinolinic acid," 1982, Brain Res 247:184-187.
Piersma, "Validation of alternative methods for developmental toxicity testing," 2004, Toxicology Letters 149:147-53.
Rasalam et al., "Characteristics of fetal anticonvulsant syndrome associated autistic disorder," 2005, Dev Med Child Neuro 47:551-555.
Reubinoff et al., "Embryonic stem cell lines from human blastocysts: somatic differentiation in vitro," 2000, Nature Biotechnology 18:399-404.
Rosano et al., "Infant mortality and congenital anomalies from 1950 to 1994: an international perspective," 2000, J Epidemiology Community Health 54:660-66.
Sabatine et al., "Metabolomic Identification of Novel Biomarkers of Mycardial Ischemia," 2005 Circulation 112:3868-875.
Shaw et al., "Periconceptional Vitamin Use, Dietary Folate, and the Occurrence of Neural Tube Defects," 1995, Epidemiology 6:219-226.
Soga et al., "Differential Metabolomics Reveals Ophthalmic Acid as an Oxidative Stress Biomarker Indicating Hepatic Glutathione Consumption," 2006, J Biol Chem 281:16788-78.
Spielmann et al., "The Embryonic Stem Cell Test, an In Vitro Embryotoxicity Test Using Two Permanent Mouse Cell Lines: 3T3 Fibroblasts and Embryonic Stem Cells," 1997, In Vitro Toxicology 10:119-27.
Wang et al., "Kynurenic Acid as a Ligand for Orphan G Protein-coupled Receptor GPR35*," 2006, J Biol Chem 281:22021-22028, published electronically on Jun. 5, 2006.
Want et al., "The Expanding Role of Mass Spectrometry in Metabolite Profiling and Characterization," 2005 Chem Bio Chem 6:1941-51.
Williams et al., "Fetal valproate syndrome and autism: additional evidence of an assosiation," 2001, Dev Med Child Neurol 43:202-06.
Wu and McAllister, "Exact mass measurement on an electrospray ionization time-of-flight mass spectrometer: error distribution and selective averaging," 2003, J Mass Spectrom 38:1043-53.
Wyszynski et al., "Increased rate of major malformations in offspring exposed to valproate during pregnancy," 2005, Neurology 64:961-5.
Yan et al., "Directed Differentiation of Dopaminergic Neuronal Subtypes from Human Embryonic Stem Cells," 2005, Stem Cells 22:781-90.
Ye et al., "FGF and Shh Signals Control Dopaminergic and Serotonergic Cell Fate in the Anterior Neural Plate," 1998, Cell 93:755-66.
Zeng et al., "Dopaminergic Differentiation of Human Embryonic Stem Cells," 2004, Stem Cell 22:925-40.
Zhao et al., "Neural Tube Defects and Maternal Biomarkers of Folate, Homocysteine, and Glutathione Metabolism," 2006, Birth Defects Res A Clin Mol Teratol 76:230-6.
Bhogal et al., 2005, Trends in Biotechnology 23:299-307.
Chen et al., 2006, Journal of Proteome Research in Toxicology, 5:995-1002.
Coecke et al., 2006, Environmental Toxicology and Pharmacology, 21:153-167.
Garrod et al., 2005, Chemical Research in Toxicology, 18:115-122.
Pellizzer et al., 2005, ALTEX, 22:47-57.
Lenz et al., 2004, Analyst, 129:535-541.
Scholz et al.,1999 Toxicology In Vitro, 13:675-681.
Barry et al., 2005, "Immunogenicity of adult mesenchymal stem cells: lessons from the fetal allograft." Stem Cells Dev. 14: 252-65.
Bonda et al., 2010, "Indoleamine 2,3-dioxygenase and 3-hydroxykynurenine modifications are found in the neuropathology of Alzheimer's disease." Redox Rep. 15: 161-8.
Copland et al., 2008, "CD34 expression on murine marrow-derived mesenchymal stromal cells: impact on neovascularization." Exp. Hematol. 36: 93-103.
English et al., 2007, "IFN-gamma and TNF-alpha differentially regulate immunomodulation by murine mesenchymal stem cells." Immunol Lett. 110: 91-100.
Gallo et al., 2007, "Limited plasticity of mesenchymal stem cells cocultured with adult cardiomyocytes." J Cell Biochem. 100: 86-99.
Jaishankar et al., 2009, "Human embryonic and mesenchymal stem cells express different nuclear proteomes." Stem Cells Dev. 18: 793-802.
Roche et al., 2009, "Comparative proteomic analysis of human mesenchymal and embryonic stem cells: towards the definition of a mesenchymal stem cell proteomic signature." Proteomics. 9: 223-32.
Rose et al., 2008, "Bone marrow-derived mesenchymal stromal cells express cardiac-specific markers, retain the stromal phenotype, and do not become functional cardiomyocytes in vitro." Stem Cells. 26: 2884-92.

(56) References Cited

OTHER PUBLICATIONS

Shi et al., 2008, "HRMAS 1H-NMR measured changes of the metabolite profile as mesenchymal stem cells differentiate to targeted fat cells in vitro: implications for non-invasive monitoring of stem cell differentiation in vivo." J Tissue Eng Regen Med. 2: 482-90.

Stone and Darlington, 2002, "Endogenous kynurenines as targets for drug discovery and development." Nat Rev Drug Discov. 1: 609-20.

Taylor et al., 1991, "Relationship between interferon-gamma, indoleamine 2,3-dioxygenase, and tryptophan catabolism." FASEB J. 5: 2516-22.

Thomson et al., 1998, "Embryonic stem cell lines derived from human blastocysts." Science. 282: 1145-1147.

Yan et al., 2005, "Directed differentiation of dopaminergic neuronal subtypes from human embryonic stem cells." Stem Cells. 23:781-790.

Yanes et al., 2010, "Metabolic oxidation regulates embryonic stem cell differentiation." Nat Chem Biol. 6: 411-7.

Harrigan et al., "Medicinal chemistry, metabolic profiling and drug target discovery: a role for metabolic profiling in reverse pharmacology and chemical genetics," Mini Rev Med Chem., 5(1):13-20 (2005).

Hayman et al., "Proteomic identification of biomarkers expressed by human pluripotent stem cells," Biochem Biophys Res Commun., 316(3):.018-23 (2004).

Bremmer et al., "The use of embryonic stem cells for regulatory developmental toxicity testing in vitro—the current status of test development," 2004, Curr Pharm Des., 10:2733-47.

Klemm et at., "Neurotoxicity of active compounds—establishment of hESC-lines and proteomics technologies for human embryo—and neurotoxicity screening and biomarker identification," 2004, ALTEX, 3:41-8.

* cited by examiner

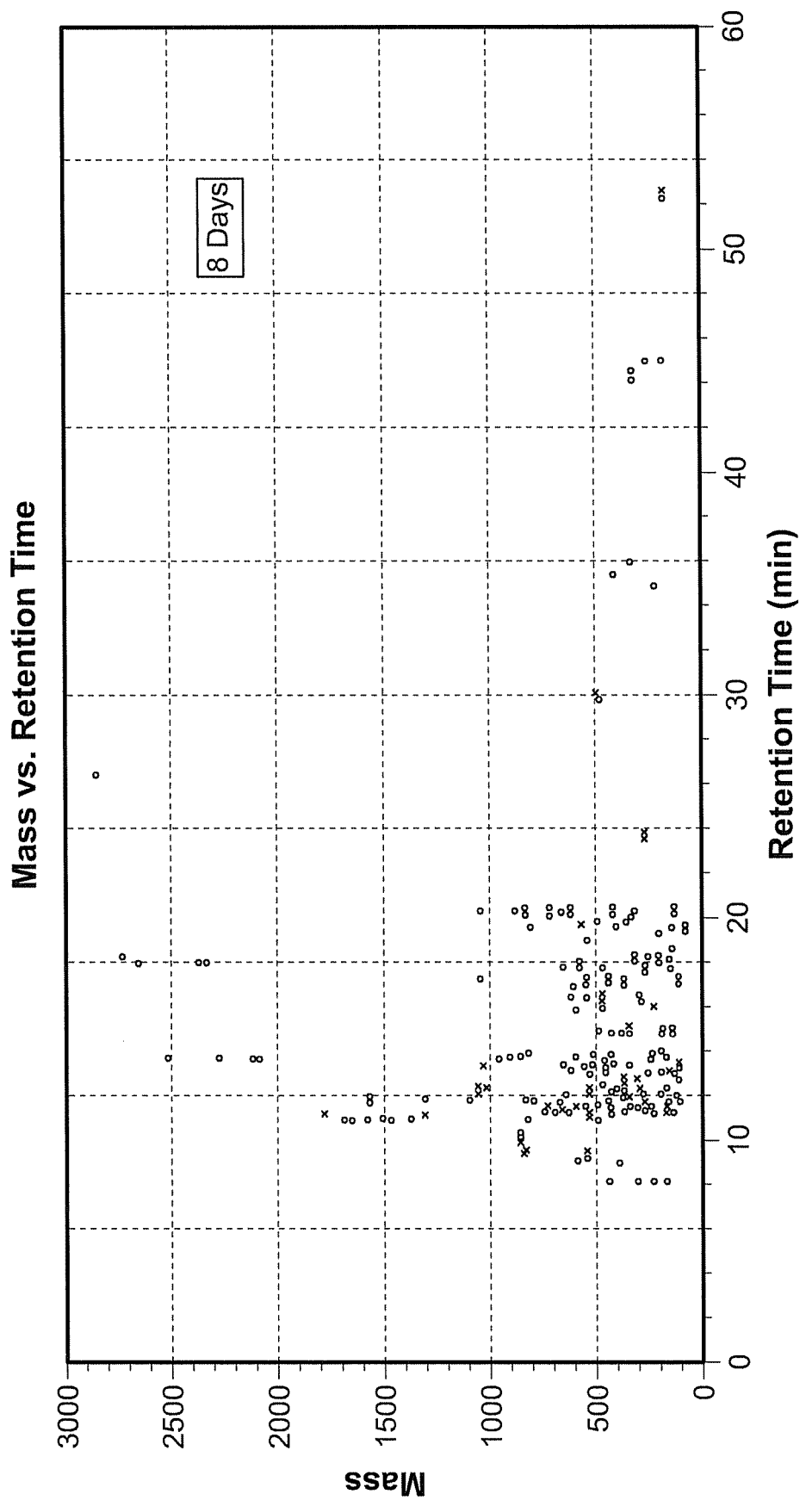

REAGENTS AND METHODS FOR USING HUMAN EMBRYONIC STEM CELLS TO EVALUATE TOXICITY OF PHARMACEUTICAL COMPOUNDS AND OTHER CHEMICALS

This application claims the priority benefit of U.S. provisional patent applications, Ser. Nos. 60/790,647, filed Apr. 10, 2006, and 60/822,163, filed Aug. 11, 2006, the entirety of which are incorporated by reference herein.

BACKGROUND OF THE INVENTION

1. Field of the Invention

This invention provides methods for toxicological screening of pharmaceuticals and other chemical compounds. The invention specifically provides reagents that are human embryonic stem cells (hESC) or hESC-derived lineage-specific cells, such as neural stem cells, neural precursor cells and neural cells, as well as methods for using these cells to detect developmental toxicity or teratogenic effects of pharmaceutical compounds and other chemicals. More particularly, the invention provides an in vitro means for analyzing toxicity of compounds predictive of their toxicity during human development. Candidate predictive biomarkers for toxic or teratogenic effects are also identified and provided herein.

2. Background of Invention

Birth defects are a major cause of infant morbidity in the United States, affecting 1 in every 33 infants born (Brent & Beckman, 1990, *Bull NY Acad Med* 66: 123-63; Rosano et al., 2000, *J Epidemiology Community Health* 54:660-66), or approximately 125,000 newborns per year. It is understood that developmental toxicity can cause birth defects, and can generate embryonic lethality, intrauterine growth restriction (IUGR), dysmorphogenesis (such as skeletal malformations), and functional toxicity, which can lead to cognitive disorders such as autism. There is an increasing concern about the role that chemical exposure can play in the onset of these disorders. Indeed, it is estimated that 5% to 10% of all birth defects are caused by in utero exposure to known teratogenic agents (Beckman & Brent, 1984, *Annu Rev Pharmacol* 24: 483-500).

Concern exists that chemical exposure may be playing a significant and preventable role in producing birth defects (Claudio et al., 2001, *Environm Health Perspect* 109: A254-A261). This concern has been difficult to evaluate, however, since the art has lacked a robust and efficient model for testing developmental toxicity for the more than 80,000 chemicals in the market, plus the new 2,000 compounds introduced annually (General Accounting Office (GAO), 1994, *Toxic Substances Control Act: Preliminary Observations on Legislative Changes to Make TSCA More Effective*, Testimony, Jul. 13, 1994, GAO/T-RCED-94-263). Fewer than 5% of these compounds have been tested for reproductive outcomes and even fewer for developmental toxicity (Environmental Protective Agency (EPA), 1998, *Chemical Hazard Data Availability Study*, Office of Pollution Prevention and Toxins). Although some attempts have been made to use animal model systems to assess toxicity (Piersma, 2004, *Toxicology Letters* 149:147-53), inherent differences in the sensitivity of humans in utero have limited the predictive usefulness of such models. Development of a human-based cell model system would have an enormous impact in drug development and risk assessment of chemicals.

Toxicity, particularly developmental toxicity, is also a major obstacle in the progression of compounds through the drug development process. Currently, toxicity testing is conducted on animal models as a means to predict adverse effects of compound exposure, particularly on development and organogenesis in human embryos and fetuses. The most prevalent models that contribute to FDA approval of investigational new drugs are whole animal studies in rabbits and rats (Piersma, 2004, *Toxicology Letters* 149: 147-53). In vivo studies rely on administration of compounds to pregnant animals at different stages of pregnancy and embryonic/fetal development (first week of gestation, organogenesis stage and full gestation length). However, these in vivo animal models are limited by a lack of robustness between animal and human responses to chemical compounds during development. Species differences are often manifested in trends such as dose sensitivity and pharmacokinetic processing of compounds. At present, animal models are only 50% efficient in predicting human developmental response to compounds (Greaves et al., 2004, *Nat Rev Drug Discov* 3:226-36). Thus, human-directed predictive in vitro models present an opportunity to reduce the costs of new drug development and enable safer drugs.

In vitro models have been employed in the drug industry for over 20 years (Huuskonen, 2005, *Toxicology & Applied Pharm* 207:S495-S500). Many of the current in vitro assays involve differentiation models using primary cell cultures or immortalized cells lines (Huuskonen, 2005, *Toxicology & Applied Pharm* 207:S495-S500). Unfortunately, these models differ significantly from their in vivo counterparts in their ability to accurately assess development toxicity. In particular, the ECVAM initiative (European Center for Validation of Alternative Methods) has used mouse embryonic stem cells as a screening system for predictive developmental toxicology. The embryonic stem cell test (EST) has shown very promising results, with a 78% statistically significant correlation to in vivo studies, and the test was able to differentiate strong teratogens from moderate/weak or non-embryotoxic compounds (Spielmann et al., 1997, *In Vitro Toxicology* 10:119-27). This model is limited in part because toxicological endpoints are defined only for compounds that impair cardiac differentiation. This model also fails to account for interspecies developmental differences between mice and humans, and so does not fully address the need in the art for human-specific model systems.

Thus there remains a need in this art for a human-specific in vitro method for reliably determining developmental toxicity in pharmaceutical agents and other chemical compounds. There also is a need in the art to better understand human development and its perturbation by toxins and other developmental disrupting agents, to assist clinical management of acquired congenital disorders and the many diseases that share these biochemical pathways, such as cancer.

The present invention provides for the assessment of a plurality of small molecules, preferably secreted or excreted by hES cells or hESC-derived lineage-specific cells, such as neural stem cells, neural precursor cells and neural cells, and is determined and correlated with health and disease or insult state. Similar analyses have been applied to other biological systems in the art (Want et al., 2005 *Chem Bio Chem* 6: 1941-51), providing biomarkers of disease or toxic responses that can be detected in biological fluids (Sabatine et al., 2005 *Circulation* 112:3868-875).

SUMMARY OF THE INVENTION

The present invention provides reagents and methods for in vitro screening of toxicity and teratogenicity of pharmaceutical and non-pharmaceutical chemicals using undifferentiated human embryonic stem cells (hESC) or hESC-derived lineage-specific cells, such as neural stem cells, neural precursor cells and neural cells. The invention provides human-specific in vitro methods for reliably determining toxicity, particularly developmental toxicity and teratogenicity, of pharmaceuticals and other chemical compounds using human embryonic stem cells (hESCs) or hESC-derived lineage-specific cells, such as neural stem cells, neural precursor cells and neural cells. As provided herein, hESCs or hESC-derived lineage-specific cells, such as neural stem cells, neural precursor cells and neural cells, are useful for assessing toxic effects of chemical compounds, particularly said toxic and teratogenic effects on human development, thus overcoming the limitations associated with interspecies animal models. In particular, the invention demonstrates that metabolite profiles of hES cells or hESC-derived lineage-specific cells, such as neural stem cells, neural precursor cells and neural cells are altered in response to known disruptors of human development.

The invention shows that the hESC metabolome is a source of human biomarkers for disease and toxic response. In particular embodiments, exposure of hESC to valproate induced significant changes in different metabolic pathways, consistent with its known activity as a human teratogen. In other embodiments, hESC exposure to varying levels of ethanol induced significant alterations in metabolic pathways consistent with alcohol's known effects on fetal development.

In one aspect, the invention provides methods for using undifferentiated pluripotent human embryonic stem cells (hESC) or hESC-derived lineage-specific cells, such as neural stem cells, neural precursor cells and neural cells, for in vitro evaluation. In the inventive methods, undifferentiated hESCs or hESC-derived lineage-specific cells, such as neural stem cells, neural precursor cells and neural cells are exposed to test compounds, preferably at concentrations reflective of in vivo levels or at levels found in maternal circulation. Further embodiments of this aspect of the invention provide for determination of the capacity of the test compound to induce differentiation of pluripotent hESC into particular cell types. In other embodiments, the inventive methods are provided using pluripotent, non-lineage restricted cells. The benefit of utilizing pluripotent stem cells is they permit analysis of global toxic response(s) and are isolated from the physiological target of developmental toxicity, i.e. the human embryo. In addition, because these cells have not differentiated into a specific lineage, the potential for false negatives is reduced. In yet further embodiments are provided methods using hESC-derived lineage-specific cells, such as neural stem cells, neural precursor cells and neural cells, for assessing toxicity and particularly developmental toxicity and teratogenicity.

In another aspect the invention provides methods for identifying predictive biomarkers of toxic responses to chemical compounds, particularly pharmaceutical and non-pharmaceutical chemicals, and particularly to known teratogens. In embodiments of this aspect, a dynamic set representative of a plurality of cellular metabolites, preferably secreted or excreted by hES cells or hESC-derived lineage-specific cells, such as neural stem cells, neural precursor cells and neural cells, is determined and correlated with health and disease or toxic insult state. Cellular metabolites according to this aspect of the invention generally range from about 10 to about 1500 Daltons, more particularly from about 100 to about 1000 Daltons, and include but are not limited to compounds such as sugars, organic acids, amino acids, fatty acids and signaling low-molecular weight compounds. Said biomarker profiles are diagnostic for toxicity of chemical compounds, particularly pharmaceutical and non-pharmaceutical chemicals, that participate in and reveal functional mechanisms of cellular response to pathological or toxic chemical insult, thus serving as biomarkers of disease or toxic response that can be detected in biological fluids. In particularly preferred embodiments of this aspect of the invention, these biomarkers are useful for identifying active (or activated) metabolic pathways following molecular changes predicted, inter alia, by other methods (such as transcriptomics and proteomics).

The invention thus also provides biomarker and pluralities of biomarkers, in some instances associated with metabolites from particular metabolic pathways, that are indicative of toxic or teratogenic insult. Said markers as provided by the invention are used to identify toxic and teratogenic insult, and in particular embodiments are used to characterize the amount or extent of said insult by being correlated with the amount or extent of the particular biomarker or plurality of biomarkers detected in cell culture media. In particular embodiments, said plurality of biomarkers provide a diagnostic pattern of toxic or teratogenic insult, more particularly identifying one or a multiplicity of specific metabolic pathways comprising metabolites detected after toxic or teratogenic insult.

The present invention is advantageous compared with inter alia the ECVAM mouse model because toxicity testing and biomarker identification are performed with human cells, specifically human embryonic stem cells (hESC). Human embryonic stem cells are able to recapitulate mammalian organogenesis in vitro (Reubinoff et al., 2000, *Nature Biotechnology* 18:399-404; He et al., 2003, *Circ Res* 93:32-9; Zeng et al., 2004, *Stem Cells* 22:925-40; Lee et al., 2000, *Mol Genet Metab* 86:257-68; Yan et al., 2005, *Stem Cells* 22:781-90) because they are pluripotent and self-renewing cells. Thus, hESCs can reveal mechanisms of toxicity, particularly developmental toxicity, and identify developmental pathways that are particularly sensitive to chemicals during early human development. The "human for human" embryonic model provided by the inventive methods disclosed herein permits a better understanding of the pathways associated with developmental toxicity, as this is a system developed directly from the target organism, as well as being a more accurate and sensitive assay for toxic or teratogenic insult in human development.

The methods of the invention provide further advantages in identifying important biomarkers for toxicity and teratogenicity by functional screening of hESCs or hESC-derived lineage-specific cells, such as neural stem cells, neural precursor cells and neural cells. These biomarkers advantageously identify metabolic and cellular pathways and mechanisms of toxicity, particularly developmental toxicity. Importantly, these biomarkers may also assist in the evaluation of toxic effects of chemicals on the developing human embryo.

In yet another aspect of the invention, differentially-detected secreted or excreted cellular products identified by methods of the invention include those associated with neurodevelopmental disorders and alterations in associated metabolic pathways, and include but are not limited to kynurenine, glutamate, pyroglutamic acid, 8-methoxykynurenate, N'-formylkynurenine 5-hydroxytryptophan, N-acetyl-D-tryptophan and other metabolites in the tryptophan and glutamate metabolic pathways.

Functional toxicity in post-natal life can be predicted using hESC since differentiated cells with critical in vivo properties can be generated in vitro. hESCs can be used to produce lineage-specific cells, including lineage-specific stem cells, precursor cells and terminally-differentiated cells, providing therein enriched populations of cells typically present in vivo in mixtures of different cell types comprising tissues. The invention thus provides methods for using hESCs to produce said enriched and developmental stage-specific populations of cells for toxicity screening of chemical compounds, particularly drugs, drug lead compounds and candidate compounds in drug development, to identify human-specific toxicities of said chemical compounds. These aspects of the methods of the invention are advantageous over art-recognized in vitro and in vivo animal model systems.

Specific preferred embodiments of the present invention will become evident from the following more detailed description of certain preferred embodiments and the claims.

BRIEF DESCRIPTION OF THE DRAWINGS

These and other objects and features of this invention will be better understood from the following detailed description taken in conjunction with the drawing wherein:

FIGS. 1A through 1C are profiles of secreted cellular metabolite biomarkers produced after contacting hESCs with 1 mM valproate. These profiles were produced using liquid chromatography/electrospray ionization-time of flight (TOF) mass spectrometry (LC/ESI-TOF-MS) after treating the cells with valproate for 24 hours (FIG. 1A), four days (FIG. 1B) and eight days (FIG. 1C). Secreted small molecules from treated (blue) and untreated (red) human embryonic stem cells were measured.

DETAILED DESCRIPTION OF PREFERRED EMBODIMENTS

Figure 1A:
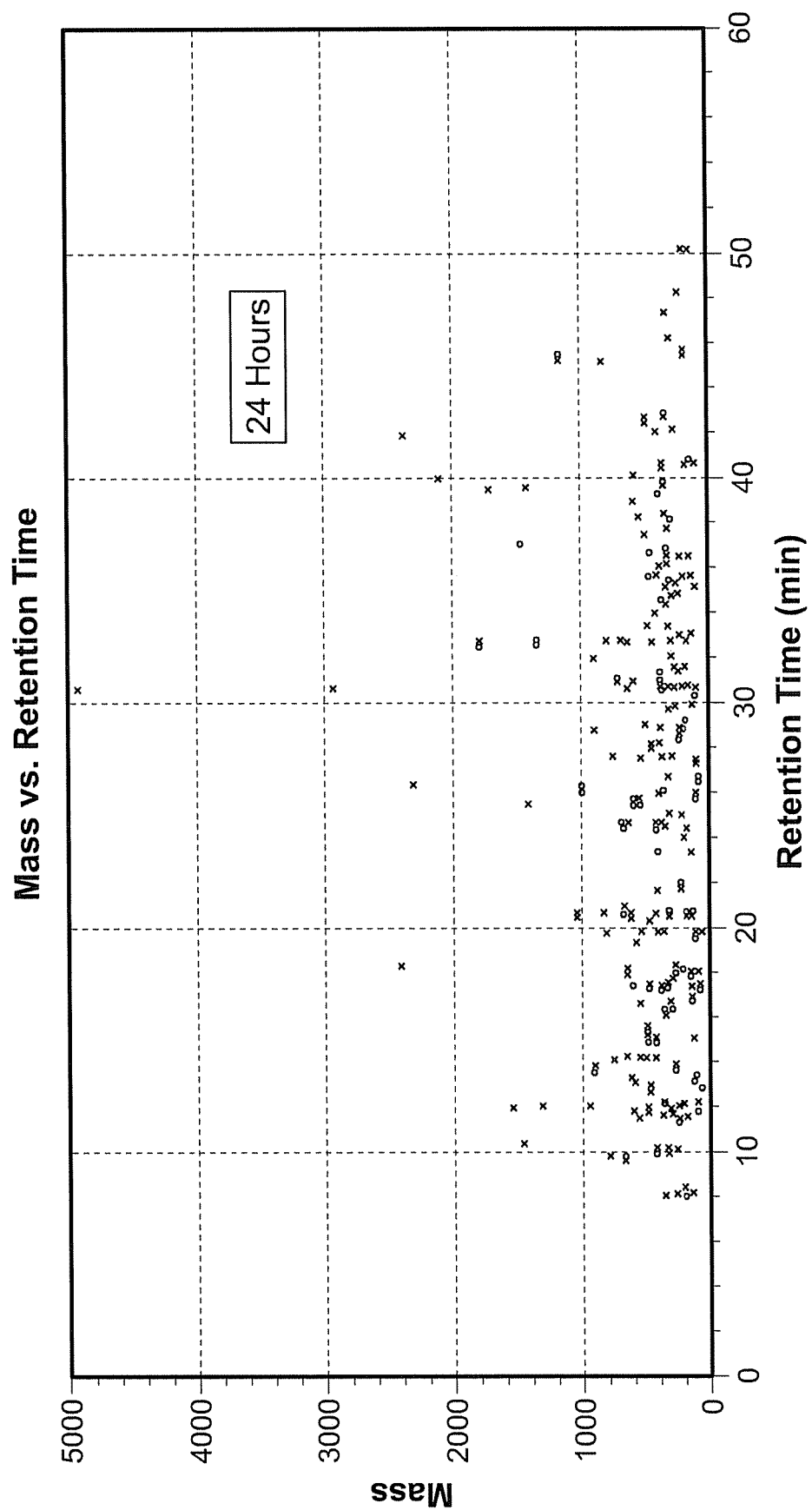

The invention provides reagents, including human embryonic stem cells (hESC) or hESC-derived lineage-specific cells, such as neural stem cells, neural precursor cells and neural cells produced therefrom, for assessing developmental toxicity using the human embryonic stem cell metabolome. Human embryonic stem cells are pluripotent, self-renewing cells isolated directly from preimplantation human embryos that recapitulate organogenesis in vitro. Lineage-specific precursor cells are derived from hES cells and have entered a specific cellular lineage, but yet remain multipotent with regard to cell type within that specific lineage. For example, neural precursors have committed to neural differentiation but yet remain unrestricted as to its neural cell type. Also within the scope of the inventive methods are terminally-differentiated cell types, such as neurons. Biochemical pathways of human development and disease are active in hESCs and or hESC-derived lineage-specific cells, because they recapitulate differentiation into functional somatic cells. Disruption of these pathways during development contributes to disorders such as neural tube defects (NTDs) and cognitive impairment. Environmental agents, namely chemicals or drugs, participate in the ontogenesis of certain acquired congenital disorders. The question of which pathways during early human development are particularly susceptible to the effects of the environment remains unsolved.

The metabolome, defined as the total dynamic set of cellular metabolites present in cells, is a product of health or disease/insult states. Metabolomics is particularly sensitive to environmental effects in comparison to other "omic" areas of study, such as genomics and proteomics. Cellular metabolites include but are not limited to sugars, organic acids, amino acids and fatty acids, particularly those species secreted or excreted from cells, that participate in functional mechanisms of cellular response to pathological or chemical insult. These cellular metabolites serve as biomarkers of disease or toxic response and can be detected in biological fluids (Soga et al., 2006, *J Biol Chem* 281:16768-78; Zhao et al., 2006, *Birth Defects Res A Clin Mol Teratol* 76:230-6), including hESC culture media. Importantly, metabolomic profiling may confirm functional changes that are often predicted by transcriptomics and proteomics.

However, because it was known that hESCs are highly sensitive to the culture microenvironment (Levenstein et al., 2005, *Stem Cells* 24: 568-574; Li et al., 2005, *Biotechnol Bioeng* 91:688-698.), their application as a source of predictive biomarkers in response to chemical compounds, including toxins, teratogens and particularly pharmaceutical agents, drug lead compounds and candidate compounds in drug development, and their usefulness in establishing in vitro models of disease and development was uncertain, inter alia because those of skill in the art could anticipate that exposure to an exogenous chemicals could be highly detrimental to survival of hES cells and preclude obtaining useful information from them. This concern has turned out not to be justified.

As used herein, the term "human embryonic stem cells (hESCs)" is intended to include undifferentiated stem cells originally derived from the inner cell mass of developing blastocysts, and specifically pluripotent, undifferentiated human stem cells and partially-differentiated cell types thereof (e.g., downstream progenitors of differentiating hESC). As provided herein, in vitro cultures of hESC are pluripotent and not immortalized, and can be induced to produce lineage-specific cells and differentiated cell types using methods well-established in the art. In preferred embodiments, hESCs useful in the practice of the methods of this invention are derived from preimplantation blastocysts as described by Thomson et al., in co-owned U.S. Pat. No. 6,200,806. Multiple hESC cell lines are currently available in US and UK stem cell banks.

The terms "stem cell progenitor," "lineage-specific cell," "hESC derived cell" and "differentiated cell" as used herein are intended to encompass lineage-specific cells that are differentiated from hES cells such that the cells have committed to a specific lineage of diminished potency. In some embodiments, these lineage-specific precursor cells remain undifferentiated with regard to final cell type. For example, neuronal stem cells are derived from hESCs and have differentiated enough to commit to neuronal lineage. However, the neuronal precursor retains 'stemness' in that it retains the potential to develop into any type of neuronal cell. Additional cell types include terminally-differentiated cells derived from hESCs or lineage-specific precursor cells, for example neural cells.

The term "cellular metabolite" as used herein refers to any small molecule secreted and/or excreted by a hESC or hESC-derived lineage-specific cells, such as neural stem cells, neural precursor cells and neural cells, produced therefrom. In preferred embodiments, cellular metabolites include but are not limited to sugars, organic acids, amino acids, fatty acids, hormones, vitamins, oligopeptides (less than about 100 amino acids in length), as well as ionic fragments thereof. Cells may also be lysed in order to measure cellular products present within the cell. In particular, said cellular metabolites are from about 10 to about 3600 Daltons in molecular weight, more particularly about 10 to about 1500 Daltons, and yet more particularly from about 100 to about 1000 Daltons.

hESCs are cultured according to the methods of the invention using standard methods of cell culture well-known in the art, including, for example those methods disclosed in Ludwig et al. (2006, Feeder-independent culture of human embryonic stem cells, *Nat Methods* 3: 637-46.). In preferred embodiments, hESCs are cultured in the absence of a feeder cell layer during the practice of the inventive methods; however, hESCs may be cultured on feeder cell layer prior to the practice of the methods of this invention.

The term "administering" as used herein refers to contacting in vitro cultures of hESCs or hESC-derived lineage-specific cells, such as neural stem cells, neural precursor cells and neural cells produced therefrom with a toxic, teratogenic, or test chemical compound. In a preferred embodiment the dosage of the compound is administered in an amount equivalent to levels achieved or achievable in vivo, for example, in maternal circulation.

Figure 1B:
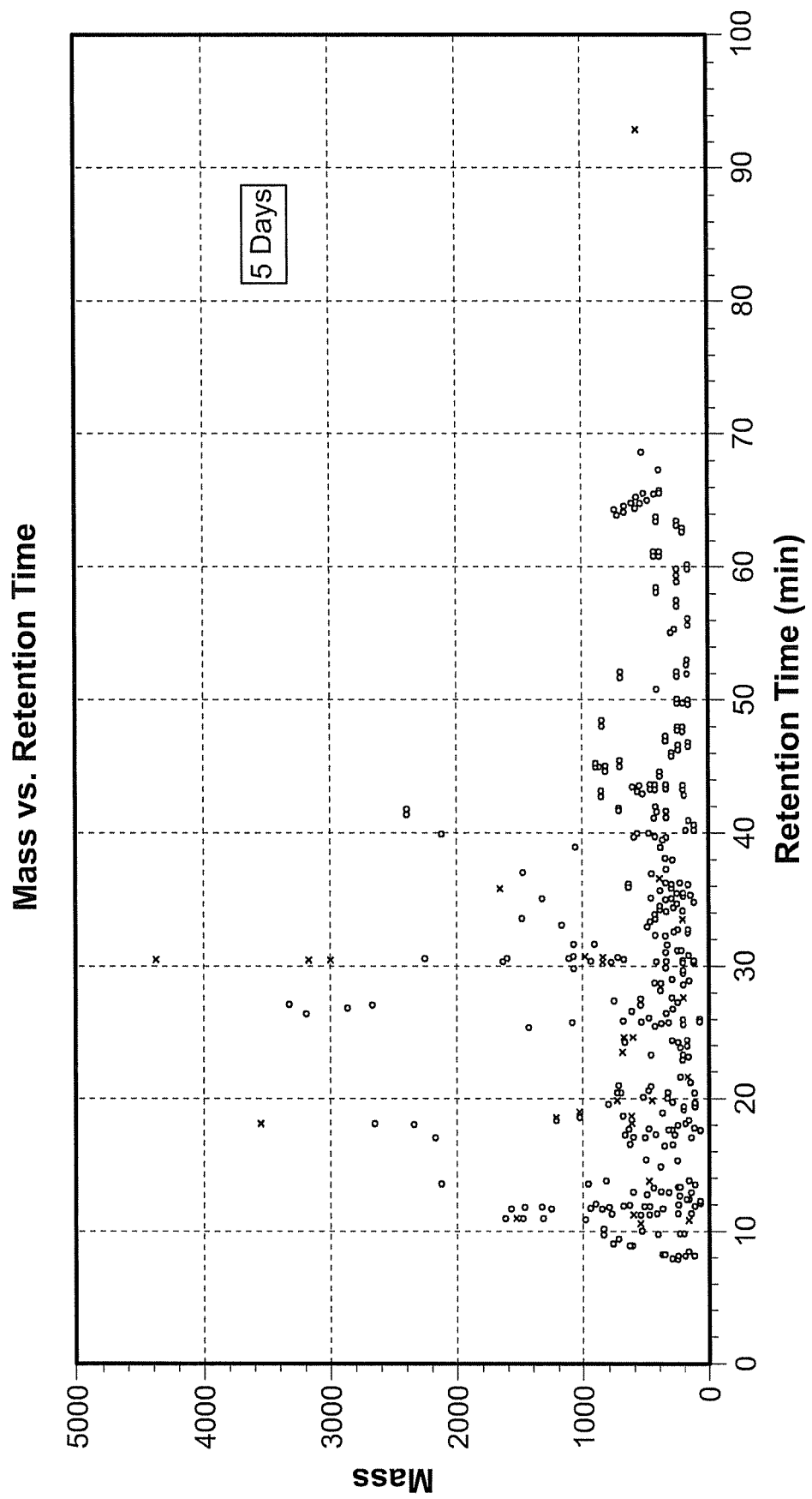

The phrases "identifying cellular metabolites that are differentially produced" or "detecting alterations in the cells or alternations in cell activity" as used herein include but are not limited to comparisons of treated hES cells or hESC-derived lineage-specific cells, such as neural stem cells, neural precursor cells and neural cells, to untreated (control) cells (i.e., cells cultured in the presence (treated) or absence (untreated) of a toxic, teratogenic, or test chemical compound). Detection or measurement of variations in cellular metabolites, excreted or secreted therefrom, between treated and untreated cells is included in this definition. In a preferred embodiment, alterations in cells or cell activity are measured by determining a profile of changes in cellular metabolites having a molecular weight of less than 3000 Daltons, more particularly between 10 and 1500 Daltons, and even more particularly between 100 and 1000 Daltons, in a treated versus untreated cell as illustrated in FIGS. 1A through 1C.

The term "correlating" as used herein refers to the positive correlation or matching of alterations in cellular metabolites including but not limited to sugars, organic acids, amino acids, fatty acids, and low molecular weight compounds excreted or secreted from hES cells or hESC-derived lineage-specific cells, such as neural stem cells, neural precursor cells and neural cells, to an in vivo toxic response. The screened cellular metabolites can be involved in a wide range of biochemical pathways in the cells and related to a variety of biological activities including, but not limited to inflammation, anti-inflammatory response, vasodilation, neuroprotection, oxidative stress, antioxidant activity, DNA replication and cell cycle control, methylation, and biosynthesis of, inter alia, nucleotides, carbohydrates, amino acids and lipids, among others. Alterations in specific subsets of cellular metabolites can correspond to a particular metabolic or developmental pathway and thus reveal effects of a test compound on in vivo development.

The term "physical separation method" as used herein refers to any method known to those with skill in the art sufficient to produce a profile of changes and differences in small molecules produced in hESCs or hESC-derived lineage-specific cells, such as neural stem cells, neural precursor cells and neural cells, contacted with a toxic, teratogenic or test chemical compound according to the methods of this invention. In a preferred embodiment, physical separation methods permit detection of cellular metabolites including but not limited to sugars, organic acids, amino acids, fatty acids, hormones, vitamins, and oligopeptides, as well as ionic fragments thereof and low molecular weight compounds (preferably with a molecular weight less than 3000 Daltons, more particularly between 10 and 1500 Daltons, and even more particularly between 100 and 1000 Daltons). In particular embodiments, this analysis is performed by liquid chromatography/electrospray ionization time of flight mass spectrometry (LC/ESI-TOF-MS), however it will be understood that cellular metabolites as set forth herein can be detected using alternative spectrometry methods or other methods known in the art for analyzing these types of cellular compounds in this size range.

Data for statistical analysis were extracted from chromatograms (spectra of mass signals) using the Agilent Mass Hunter software (Product No. G3297AA, Agilent Technologies, Inc., Santa Clara, Calif.); it will be understood that alternative statistical analysis methods can be used. Masses were binned together if they were within 10 ppm and eluted within a 2 minutes retention time window. A binned mass was considered to be the same molecule across different LC/ESI-TOF-MS analyses (referred to herein as an "exact mass," which will be understood to be ±10 ppm). Binning of the data is required for statistical analysis and comparison of masses across the entire experiment. If multiple peaks with the same mass at the same retention time within a single sample were detected by Mass Hunter, they were averaged to assist data analysis. Masses lacking a natural isotopic distribution or with a signal-to-noise ratio of less than 3 were removed from the data prior to analysis. One of skill in the art will appreciate that the results from this assay provide relative values that are assessed according to annotated values within 10 ppm to provide an identity for the molecular weight detected. Thus, a mass shift within 10 ppm is considered consistent with determining the identity of a specific cellular metabolite annotated known in the art due to differences in ionization source and instrumentation, e.g. between different experiments or using different instruments.

As used herein, a mass was considered to be the same across LC/ESI-TOF-MS runs using a simple algorithm that first sorts the data by mass and retention time. After sorting, a compound was considered unique if it had a retention time difference of less than or equal to three minutes and a mass difference less than or equal the weighted formula (0.000011× mass). If a series of measurements fit this definition it was considered to be from the same compound. If either the mass or the retention time varied by more than the limits listed above it was considered to be a different compound and given a new unique designation.

Significance tests were determined by performing ANOVAs on the log base 2 transformed abundance values of unique compounds present in treated and untreated media at each time point. A randomized complete block design was used with the ANOVA model including the effects of treatment, experiments, and a residual term, with the following formula: $Log_2(abundance_{tb})=treatment_t+experiment_b+error_{tb}$.

Missing data were omitted from the test changing the degrees of freedom rather than assuming the missing data were absent. This assumption was made because the extensive filtering performed by the Mass Hunter software may miss or filter certain peaks because they are below a certain abundance threshold and not zero. The ANOVA F-test was considered significant if its p-value was less than 0.05. Fold changes were calculated using the least squared means for a given time and treatment.

The term "biomarker" as used herein refers to cellular metabolites that exhibit significant alterations between treated and untreated controls. In preferred embodiments, biomarkers are identified as set forth above, by methods including LC/ESI-TOF-MS. Metabolomic biomarkers are identified by their unique molecular mass and consistency with which the marker is detected in response to a particular toxic, teratogenic or test chemical compound; thus the actual identity of the underlying compound that corresponds to the biomarker is not required for the practice of this invention. Alternatively, certain biomarkers can be identified by, for example, gene expression analysis, including real-time PCR, RT-PCR, Northern analysis, and in situ hybridization, but these will not generally fall within the definition of the term "cellular metabolites" as set forth herein.

The basal metabolome of undifferentiated hESCs served as a collection of biochemical signatures of functional pathways that are relevant for sternness and self-renewal. Metabolite profiling was conducted on excreted or secreted cellular metabolites as opposed to intracellular compounds. Ultimately, biomarkers discovered in vitro are expected to be useful for analyzing in vivo biofluids such as serum, amniotic fluid and urine, complex mixtures of extracellular biomolecules. This is advantageous over invasive procedures such as tissue biopsies because small molecules in biofluids can be detected non-invasively (in contrast to intracellular compounds). In addition, processing cellular supernatant for mass spectrometry is more robust and less laborious than cellular extracts. However, cellular extracts (from, for example, lysed cells) can be utilized in the methods of the invention.

The term "biomarker profile" as used herein refers to a plurality of biomarkers identified by the inventive methods. Biomarker profiles according to the invention can provide a molecular "fingerprint of the toxic and teratogenic effects of a test compound and convey what cellular metabolites, specifically excreted and secreted cellular metabolites, were significantly altered following test compound administration to hESCs or hESC-derived lineage-specific cells, such as neural stem cells, neural precursor cells and neural cells. In these embodiments, each of the plurality of biomarkers is characterized and identified by its unique molecular mass and consistency with which the biomarker is detected in response to a particular toxic, teratogenic or test chemical compound; thus the actual identity of the underlying compound that corresponds to the biomarker is not required for the practice of this invention.

The term "biomarker portfolio" as used herein refers to a collection of individual biomarker profiles. The biomarker portfolios may be used as references to compare biomarker profiles from novel or unknown compounds. Biomarker portfolios can be used for identifying common pathways, particularly metabolic or developmental pathways, of toxic or teratogenic response.

These results set forth herein demonstrated that human embryonic stem cell metabolomics, and metabolomics from hESC-derived lineage-specific cells, such as neural stem cells, neural precursor cells and neural cells, can be used in biomarker discovery and pathway identification. Metabolomics detected small molecules secreted by hESCs or hESC-derived lineage-specific cells, such as neural stem cells, neural precursor cells and neural cells, produced therefrom and the identified biomarkers can be used for at least two purposes: first, to determine specific metabolic or developmental pathways that respond to or are affected by toxin or teratogen exposure, particularly said pathways utilized or affected during early development that are sensitive to toxic, teratogenic or test chemical compounds that are developmental disruptors and participate in the ontogenesis of birth defects; and second, to provide cellular metabolites that can be measured in biofluids to assist management and diagnosis of toxic exposure, birth defects or other disease.

A biomarker portfolio from hESCs or hESC-derived lineage-specific cells, such as neural stem cells, neural precursor cells and neural cells, produced therefrom can also serve as a high throughput screening tool in preclinical phases of drug discovery. In addition, this approach can be used to detect detrimental effects of environmental (heavy metals, industrial waste products) and nutritional chemicals (such as alcohol) on human development. Ultimately, the methods of this invention utilizing the hESC metabolome or the metabolome of or hESC-derived lineage-specific cells, such as neural stem cells, neural precursor cells and neural cells, can assist pharmaceutical, biotechnology and environmental agencies on decision-making towards development of compounds and critical doses for human exposure. The integration of chemical biology to embryonic stem cell technology also offers unique opportunities to strengthen understanding of human development and disease. Metabolomics of cells differentiated from hESC should serve similar roles and be useful for elucidating mechanisms of toxicity and disease with greater sensitivity for particular cell or tissue types, and in a human-specific manner. For example, key metabolic pathways, including as set forth herein folate, glutamate and tryptophan synthesis and degradation, may be differentially disrupted in earlier versus later stages of human development. In addition, metabolite profiles of neural precursor cells or neuronal cell populations can reveal biomarkers of neurodevelopmental disorders in target cell types. The association of metabolomics to stem cell biology can inform the mechanisms of action of folic acid and neural tube defects in the early human embryo.

Biomarker portfolios produced using the hESC-dependent and hESC-derived lineage-specific cell-dependent methods of this invention can also be used in high throughput screening methods for preclinical assessment of drug candidates and lead compounds in drug discovery. This aspect of the inventive methods produces minimal impact on industry resources in comparison to current developmental toxicology models, since implementation of this technology does not require experimental animals. The resulting positive impact on productivity enables research teams in the pharmaceutical industry to select and advance compounds into exploratory development with greater confidence and decreased risk of encountering adverse developmental effects.

The term "developmental pathway" as used herein refers to developmental or metabolic pathways in embryonic and fetal development.

"Supernatant" as used herein may include but is not limited to extracellular media, co-cultured media, cells, or a solution of fractionated or lysed cells.

Cellular metabolite profiles obtained from analysis of toxins, teratogens, alcohol, and test chemical compounds can be used to compose a library of biomarker portfolios. These portfolios can then be used as a reference for toxicological analysis of unknown chemical compounds. A similar strategy has been validated as a means to determine cellular changes that arise in response to chemicals in non-hESC systems (Daston & Nacliff, 2005, *Reprod Toxicolog* 19:381-94; Fella et al., 2005, *Proteomics* 5:1914-21). Metabolic profiles of novel compounds can be compared to known biomarker portfolios to identify common mechanisms of toxic response. This approach can reveal functional markers of toxic response, which serve as screening molecules that are shared at least in part as a consequence of exposure to various different toxic and teratogenic compounds. Such hESC-derived small molecules can be used as measurable mediators of toxic response that refine or replace costly and complex screening systems (such as in vivo animal models) and have the additional advantage of being specific for human cells and human metabolic and developmental pathways.

EXAMPLES

The Examples which follow are illustrative of specific embodiments of the invention, and various uses thereof. They are set forth for explanatory purposes only, and are not to be taken as limiting the invention.

Example 1

Developmental Toxicology Screening

To demonstrate the efficacy of hESCs as a model system for developmental toxicity testing, hESCs were treated with a known teratogen, valproate (VPA). Valproate is a common mood stabilizer and anti-convulsant drug with clinical indications in epilepsy and bipolar disorder (Williams et al., 2001, *Dev Med Child Neuro* 43:202-6) that has been associated with developmental abnormalities (Meador et al., 2006, *Neurology* 67: 407-412). The mechanism by which valproate produces developmental defects, however, is not fully understood, despite the increased susceptibility of the nervous system (Bjerkedal et al., 1982, *Lance* 2:109: Wyszynski et al., 2005, *Neurology* 64:961-5; Rasalam et al., 2005, *Dev Med Child Neuro* 47:551-555). Exposure to valproate results in a pronounced increase in spina bifida and neural tube defects (NTDs; Bjerkedal et al., 1982, *Lancet* 2:109) at ten-to-twenty times that of the general population, as well as cognitive disorders such as autism (Adab et al., 2004, *J Neurol Neurosurg Psychiatry* 75:1575-83). However, since VPA is an anti-convulsant drug with clinical indications in epilepsy and bipolar disorder (Williams et al., 2001, *Dev Med Child Neurol* 43:202-06), treatment generally must be sustained throughout pregnancy.

Folic acid supplementation prior to pregnancy reduces the incidence of spina bifida by 70% (Shaw et al., 1995, *Epidemiolog* 6:219-226) although its precise mechanism of action is unknown. In addition, homocysteine and glutathione have also been implicated in NTDs (Zhao et al., 2006, *Birth Defects Res A Clin Mol Teratol* 76:230-6). Thus, metabolite profiles of folate and related pathways were candidates for changes in response to valproate. In the results set forth herein, folic acid was significantly increased (by 16%) in the extracellular media of hES cells treated with valproate (p=0.022 at eight days, Table 3 and FIG. 4) but not its derivative dihydrofolate. Since mammalian cells do not synthesize folic acid, valproate may act by interfering with cellular uptake of folic acid.

Exposure of hESCs was performed as follows. H1 hESC (passage 41) were cultured on Matrigel (BD Scientific, San Jose, Calif.) in the absence of a feeder layer. hESCs were maintained in conditioned medium (CM) collected from mouse embryonic fibroblasts (MEFs) (80% DMEM/F12, Invitrogen, Carlsbad, Calif.) and 20% KNOCKOUT serum replacement (Invitrogen) supplemented with 1 mM L-glutamine (Invitrogen), 1% MEM non-essential amino acids (Invitrogen), and 0.1 mM 2-mercaptoethanol (Sigma, Chemical Co., St. Louis, Mo.). Prior to feeding hESCs, the culture medium was supplemented with 4 ng/mL human recombinant basic fibroblast growth factor (Invitrogen). hESCs were passaged when the wells were ~80% confluent. To passage, hESCs were incubated in a 1 mg/mL dispase (Invitrogen)/DMEM/F12 solution for 7-10 minutes at 37° C. After this treatment hESCs were washed and seeded on fresh Matrigel coated plates. In parallel studies disclosed herein, H1 and H9 cells were cultured in defined medium known as TeSR (Ludwig et al., 2006, Id.).

H1 and H9 (equivalent to NIH code WA01/WA09) hESC were treated with valproate (VPA) (22 μM and 1 mM) (Sigma # P4543) according to the procedure outlined below; each experiment involved three separate VPA treatments, and each treatment group had a parallel control group with a total of six 6-well culture dishes (Nunc, Naperville, Ill.) per experiment (two 6-well culture dishes per treatment). Treatment 1 (labeled 24 H) exposed hESC cells to 1 mM VPA (Sigma) for 24 hours followed by collection of supernatant and cell pellets. In a second treatment group (labeled 4 D), hESC cells were exposed to 22 μM or 1 mM VPA for 4 days and harvested on day 4. In a third treatment group (labeled extended culture, EC), hESC cells received 22 μM or 1 mM VPA for 4 days followed by culture in standard hESC media for an additional four days. For this group, cells and supernatant were harvested on day eight.

To assess the effects of teratogenic VPA treatment on hESCs, the treated cells were analyzed as set forth below to determine changes in a total dynamic set of small molecules present in cells according to health and disease or insult states. Small molecules including but not limited to sugars, organic acids, amino acids, fatty acids, hormones, vitamins, oligopeptides (less than about 100 amino acids in length), as well as ionic fragments thereof and signaling low molecular weight compounds were known to participate in and reveal functional mechanisms of cellular response to pathological or chemical insult. These analyses were also used to identify active pathways following molecular changes predicted by other analyses including for example transcriptomics and proteomics.

Supernatant from VPA-treated and control hESCs were subjected to liquid chromatography and electrospray ionization time of flight mass spectrometry (LC/ESI-TOF-MS) to assess changes and differences in small molecules (as defined herein) produced by the cells in the presence and absence of VPA treatment. Supernatant was collected from control and treated plates of hESCs at 24 H, 4 D, and 8 D, and CM was collected as a "no treatment" control. The supernatant and media were stored at −80° C. until preparation for mass spectrometry analysis. For analysis, samples were prepared in a 20% Acetonitrile (Fisher Scientific Co., Pittsburgh, Pa.) solution (comprising 500 µL of supernatant, 400 µL acetonitrile and 1.1 mL distilled water) and centrifuged through a Millipore 3 kDa Centricon column (Millipore, Billerica, Mass.) for 3 hours at 4575×g to remove proteins. The flow-through was retained for analysis, as it contains small molecules free of high molecular weight compounds such as proteins. In each analysis, three replicates for each sample were injected into a 2.1×200 mm C18 column using a 90 minute gradient from 5% Acetonitrile, 95% Water, 0.1% Formic Acid to 100% Acetonitrile, 0.1% Formic Acid at a flow rate of 40 µL/min. ESI-TOF-MS (TOF) was performed on the flow-through using an Agilent ESI-TOF mass spectrometer. Data was collected from 100-3600 m/z, and particularly in the 0-1500 m/z range. The raw data was analyzed to identify the separated small molecules using a computer compilation and analysis program (Mass Hunter) provided by the manufacturer and according to manufacturer's instructions (Agilent; statistical analyses were performed as described above in the Detailed Description and Preferred Embodiments. This analysis generated lists of retention time/accurate mass pair feature. Another program (Mass Profiler, Agilent) was used to compare multiple run sets to find ion intensity changes of features that changed between the sample conditions. Significance tests were determined by performing ANOVAs on the log base 2 transformed abundance values of unique compounds present in treated and untreated media at each time point.

The plurality of small molecules identified using these methods were then compared with exact mass and retention time from ESI-TOF-MS using public databases (for example, at http://metlin.scripps.edu., www.nist.gov/srd/chemistry.htm; http://www.metabolomics.ca/). Mass spectrometry analysis also included predicted chemical structures of small molecules based upon exact mass, although currently-available public databases do not in every instance include matching small molecules due to database limitations. In addition, more comprehensive private databases are available for comparative analysis, such as the NIST/EPA/NIH Mass Spectral Library: 05. NIST ASCII Version.

The results of these analyses are shown in FIGS. 1A through 1C and FIG. 2A through 2C. In FIGS. 1A through 1C each feature on the plot corresponds to a small molecule with specific exact mass and retention time. The plots summarize significant differences found between treated (blue) and untreated (red) groups at different time points. As shown in the Figure, at 24 hours (24 H) there was consistent down-regulation of the secreted biomolecules in treated (blue) cells in comparison to untreated (red) controls. At four days (4 D) and eight days (EC), treated (blue) cells secreted a higher number of small molecules in comparison to untreated cells (red); said small molecules were thus considered as candidate biomarkers. In particular, metabolites from the folate pathway, including tetrahydrofolate (exact mass 444) and dihydrofolate (exact mass 441) were detected. These findings were considered significant, since they show for the first time that hESCs contacted with a known teratogen (VPA) that causes a birth defect (spina bifida) respond by up-regulating a metabolic pathway that produces a compound (folate) known to ameliorate the effects of the teratogen when administered to a woman bearing a developing embryo or fetus.

Further, the results shown in FIGS. 1A through 1C revealed approximately 40 small molecules that were absent in treated groups, suggesting that multiple cellular pathways were "silenced" in response to VPA at 24 hours in comparison to untreated controls. At four and eight days after treatment, however, multiple candidate biomarkers were upregulated in treated versus untreated human embryonic stem cells; these results are shown in Table 1. Candidate biomarkers were identified as small molecules showing a change in treated versus untreated cells measured to be at least a two-fold difference. In many instances, these small molecules are absent or detected at very low concentrations in untreated human embryonic stem cells.

These studies demonstrated that the claimed methods for assessing developmental toxicity and the identification of biomarkers using hESCs provided robust information on changes in small molecule content of cells in response to being contacted with a known teratogen, VPA. The results concerning a compound (VPA) that is involved in the etiology of spina bifida and neural tube defects (NTDs) (Bjerkedal et al., 1982, *Lancet* 2:109) when exposed to a developing human conceptus are particularly striking. The results shown here indicated a marked increase (2 to 8 fold) in key metabolites of the folate pathway (dihydrofolic acid, tetrahydrofolic acid, S-adenosylmethionine) following treatment with VPA (in comparison to untreated cells). These methods were reproducible, having been repeated with consistent results obtained in three independent studies using hESCs and on non-embryonic cells (human fibroblasts) as controls (data not shown), and suggested a heretofore unknown adaptive response of the fetus to the chemical/environmental insult and identified sensitive markers for said insult(s).

The mechanism for VPA developmental defects, however, is not fully understood despite the fact that the nervous system is particularly sensitive to its effects (Bjerkedal et al., 1982, *Lancet* 2:109; Narita et al., 2000, *Pediatric Res* 52:576-79; Rasalam et al., 2005, *Dev Med Child Neurol* 47:551-55). Folic acid supplementation prior to pregnancy prevents the incidence of spina bifida by 70% (Shaw et al., 1995, *Epidemiolog* 6:219-226), although the exact mechanism of action is also unknown. The information obtained herein can be used to elucidate mechanisms of action of folic acid and neural tube defects in the early human embryo. These methods can also be applied to other known teratogens, such as retinoic acid, warfarin, and thalidomide (Franks et al., 2004, *Lancet* 363:1802-11) to validate the predictive ability of hESCs using the methods of the invention.

Table 1: Candidate small molecules (biomarkers) of developmental toxicity detected in undifferentiated human embryonic stem cells treated with 1 mM valproate in comparison to untreated controls.

TABLE 1

Candidate small molecules (biomarkers) of developmental toxicity detected in undifferentiated human embryonic stem cells treated with 1 mM valproate in comparison to untreated controls.
Change in VPA Treated hESCs in comparison to untreated controls

| Exact mass | RT | 24 Hours | 4 Days | 8 Days | Candidate Biomarker |
|---|---|---|---|---|---|
| 355.066 | 16 | | UP | | SAM S-ADENOSYLMETHIONINAMINE |
| 355.12 | 30 | | UP | | SAM |
| 381.1574 | 12 | | UP | UP | GLUTATHIONE |
| 398.21 | 39 | DOWN | UP | | SAM OXOBUTANOATE |
| 441.8831 | 12 | | | UP | DIHYDROFOLIC ACID |
| 444.1729 | 17 | | UP | UP | TETRAHYDROFOLIC ACID |
| 472.16 | 17 | ZERO | UP | UP | TETRAHYDROFOLATE |
| 612.15 | 17 | DOWN | DOWN | UP | GLUTATHIONE OXIDIZED |

RT = retention time
Small molecule detection was conducted with LC/ESI-TOF-MS in triplicate samples of supernatant processed independently.

Figure 2A:
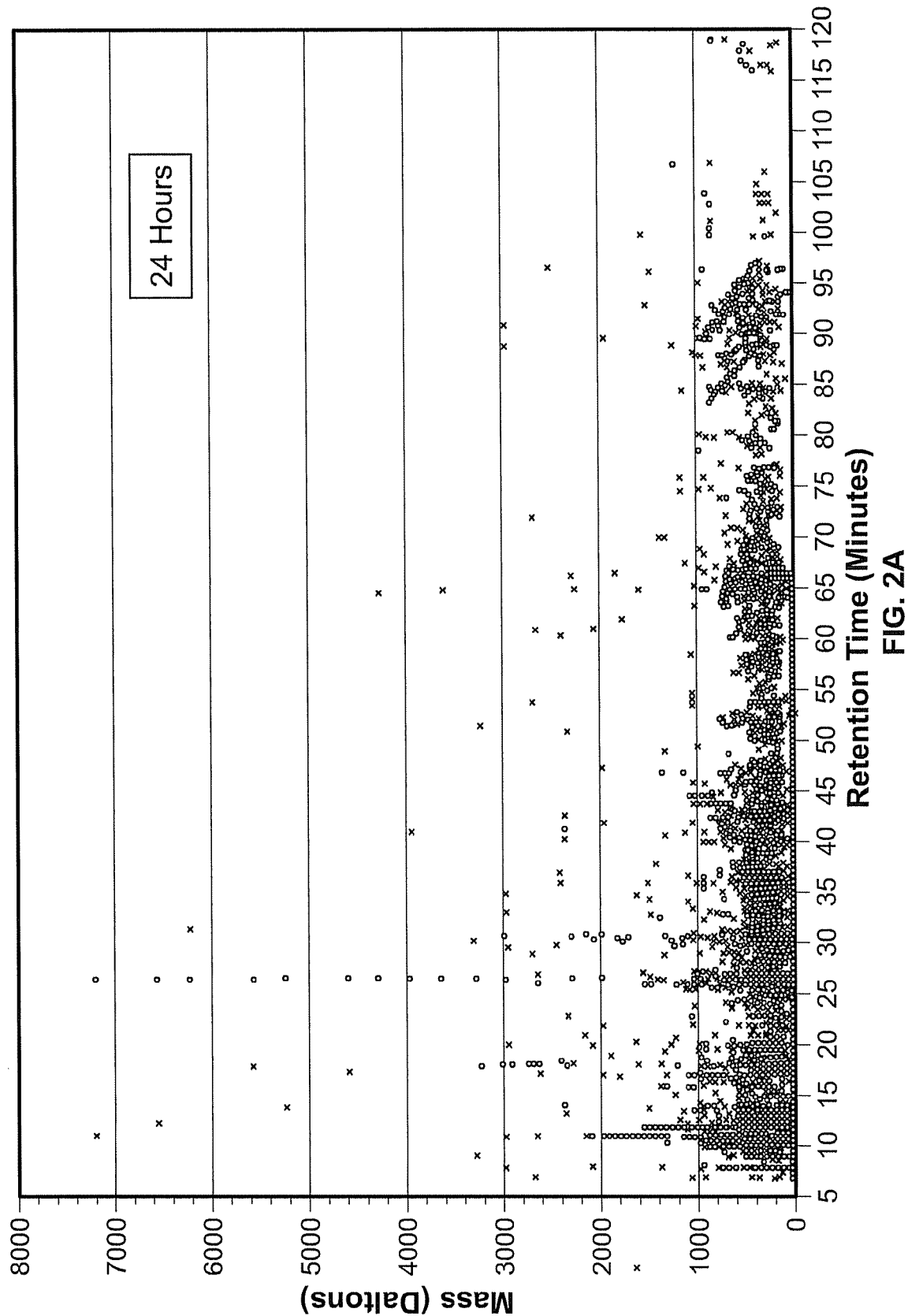
FIGS. 2A through 2D are profiles of secreted/excreted cellular metabolite biomarkers produced after contacting hESCs with 1 mM valproate. These profiles were produced using liquid chromatography/electrospray ionization time of flight mass spectrometry (LC/ESI-TOF-MS) after treating cells with valproate for 24 hours (FIG. 2A), four days (FIG. 2B), eight days (FIG. 2C), and comparative metabolic profiling of hES cells (blue) and conditioned media (yellow) (FIG. 2D).
Figure 2B:
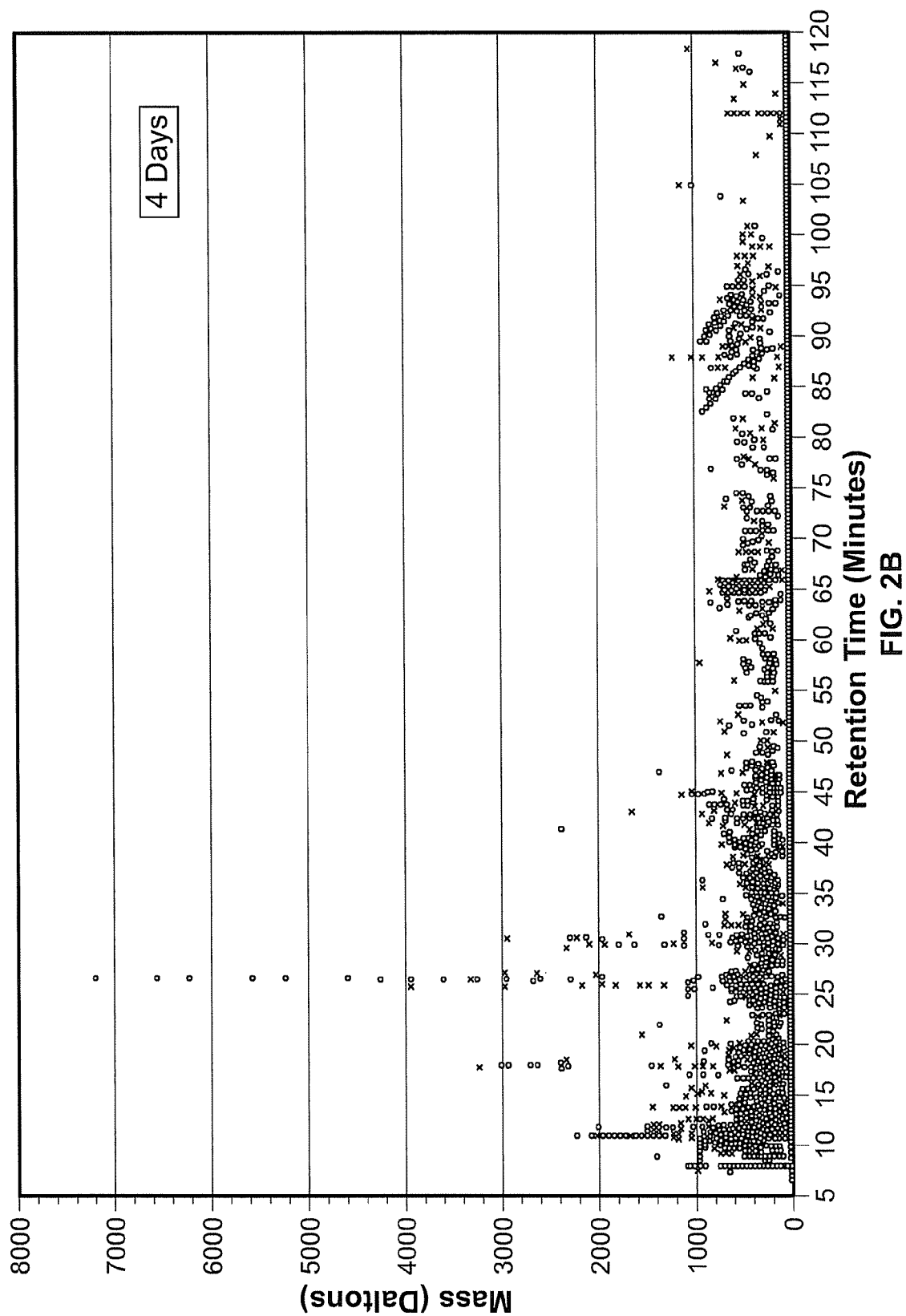
Figure 2C:
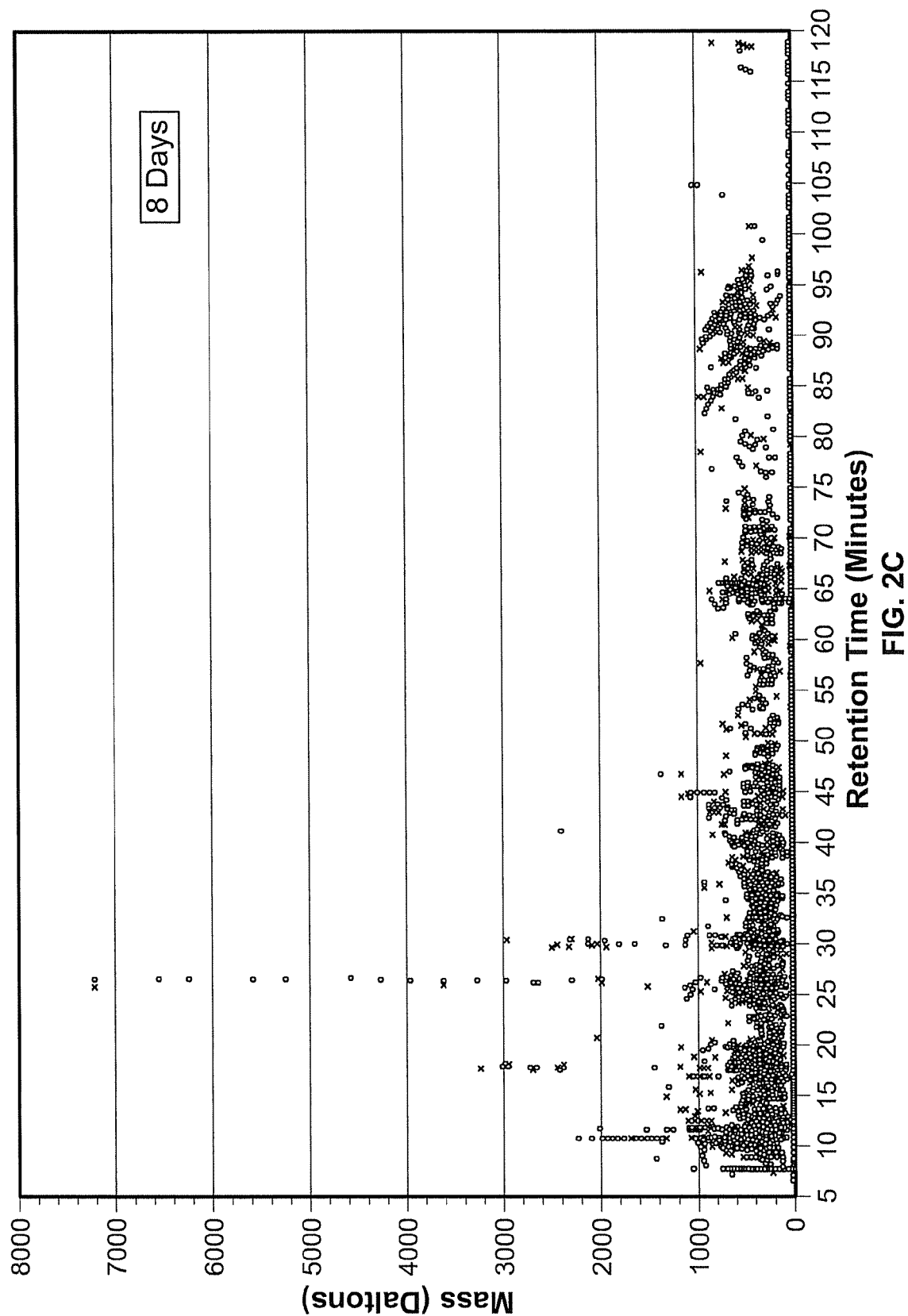
Figure 2D:
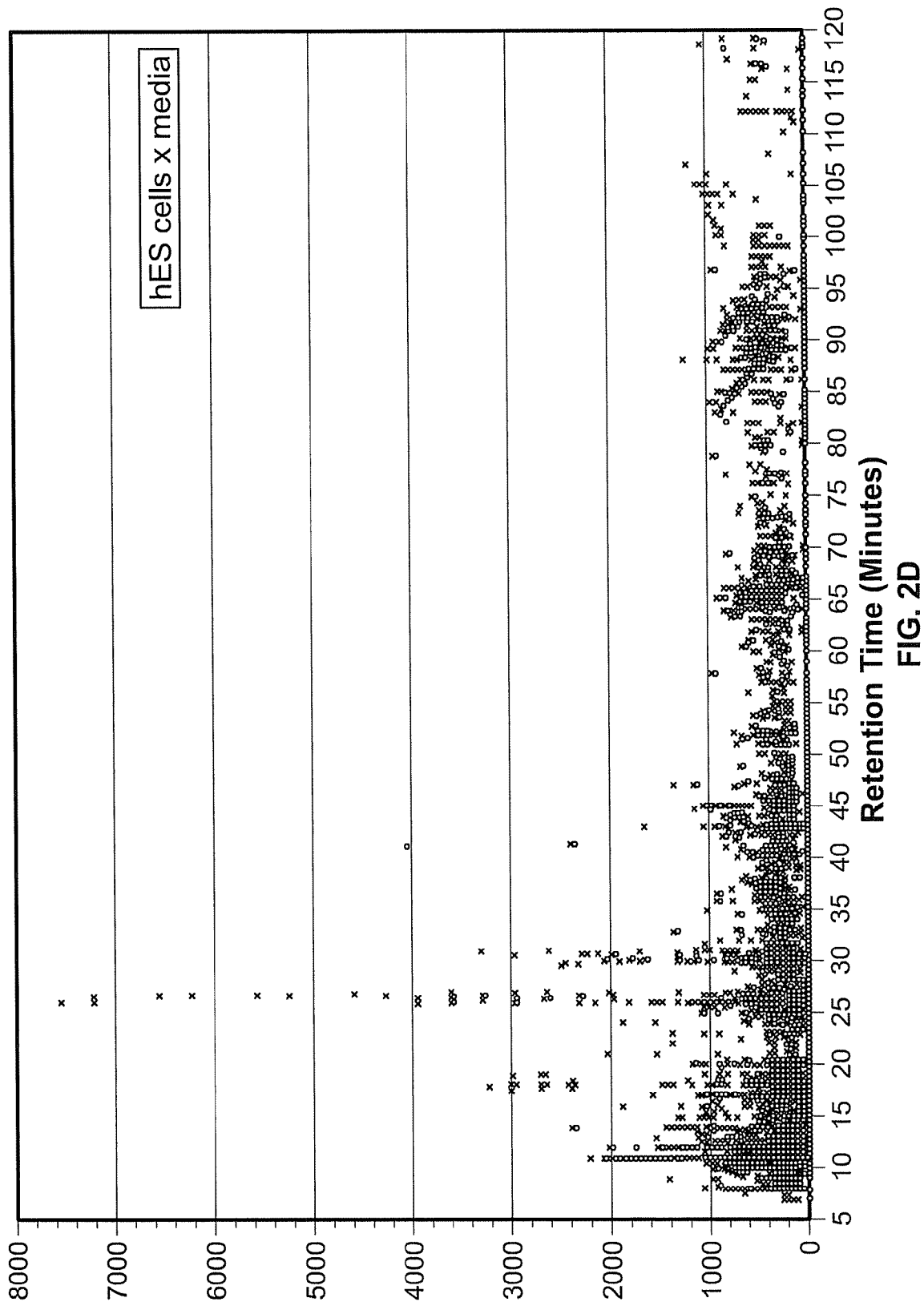
Figure 3:
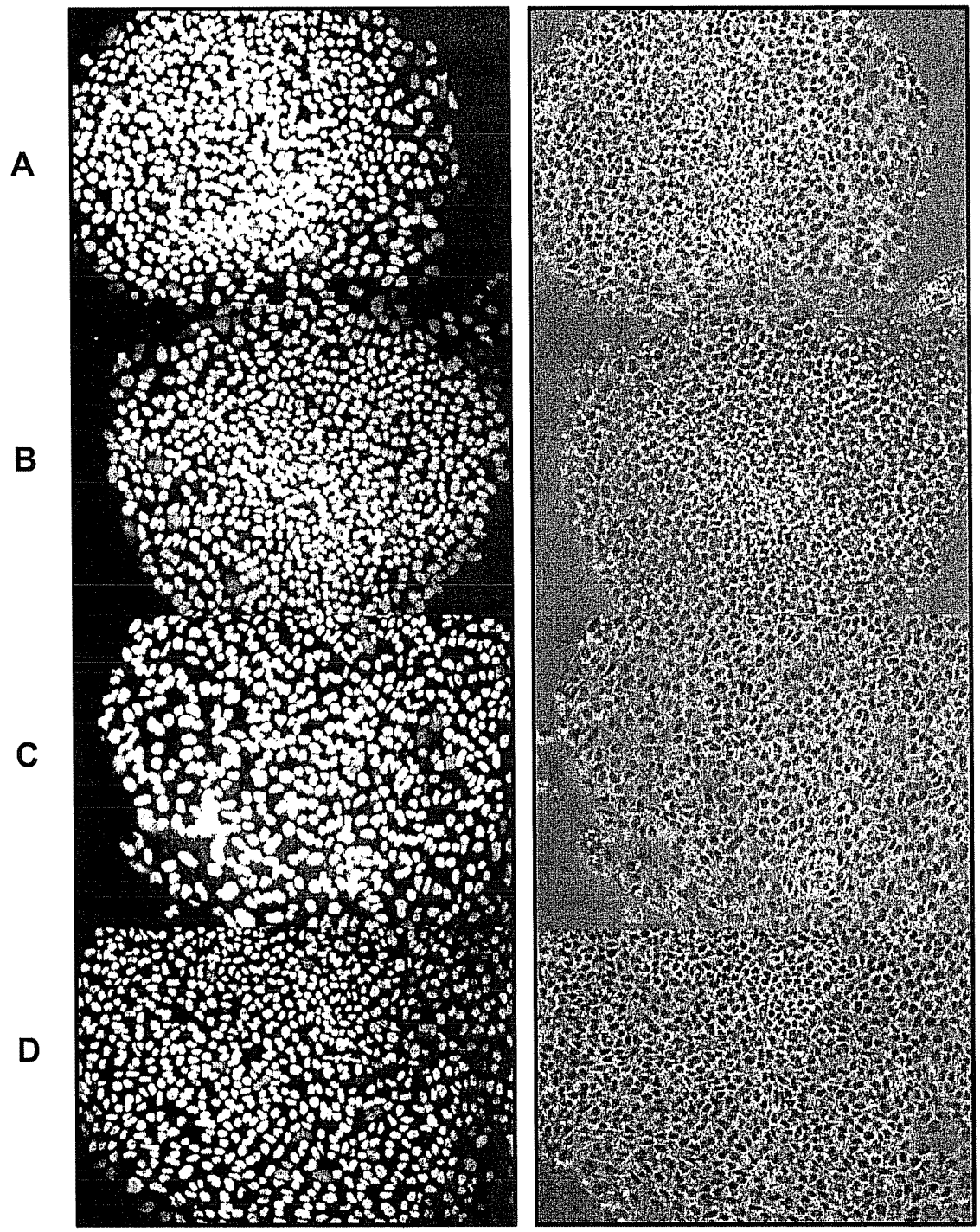
FIGS. 3A through 3D are photomicrographs of cellular morphology showing the pluripotent embryonic stem cells following extended culture. The marker Oct-4 was retained in a similar manner as untreated controls (FIG. 3A=5 days valproate, FIG. 3B=5 days control, FIG. 3C-8 days valproate, FIG. 3D-8 days control).

As discussed above, metabolite profiles were determined at 24 hours, four days and eight days after valproate treatment. At four days after treatment, multiple candidate biomarkers were upregulated in treated versus untreated human embryonic stem cells (shown in FIGS. 2A through 2C). In addition to the results set forth above regarding increased levels of certain metabolites, multiple metabolite peaks were down-regulated in response to valproate at 24 hours in comparison to untreated controls (FIGS. 2A through 2C).

hESCs were cultured in conditioned media from mouse embryonic fibroblasts, which generated 1277 of the 3241 measured compounds. Many metabolites in human development and disease are likely present in conditioned media from mouse embryonic fibroblasts due to common metabolic pathways. Rigorous investigation is required to validate candidate biomarkers that are not exclusive to hESCs and are also present in the media.

Example 2

Gene Expression Analysis

The efficacy of the analysis shown in Example 1 was confirmed by gene expression studies, wherein changes in gene expression were observed following VPA treatment of hESCs. VPA treatment was not detrimental to hESCs, which remained viable for multiple passages following teratogen exposure, thus enabling gene expression analysis to be performed.

Treated and control H1/NIH code WA01 hES cells (passage 41) were analyzed by real-time PCR, and each treatment group was paired with a corresponding control group that received the standard growth media combination of CM+bFGF without VPA. In these studies, total cellular RNA was extracted from cells harvested at 24 hours (24 H), 4 days (4 D) and 8 days (EC) using the RNA Easy Kit (Qiagen, Valencia, Calif.) according to the manufacturer's instructions.

Expression levels of candidate test genes and a housekeeping gene (Beta-2-microglobulin) were evaluated by quantitative real-time PCR using a DNA Engine-Opticon 2 Detection System (MJ Research, Watertown, Mass.). The housekeeping gene acts as an internal control for normalization of RNA levels. The primers used for real-time PCR reactions were designed using Beacon Designer software (Premier Biosoft International, Palo Alto, Calif.). RNA was reverse transcribed using iScript cDNA Synthesis kit (Bio-Rad, Hercules, Calif.), wherein each cDNA synthesis reaction (20 µL) included 4 µL of 5× iScript reaction mix, 1 µL of iScript reverse transcriptase, and 2 µL of RNA. PCR was performed on cDNA in PCR reaction mixtures (25 µL) each containing 12.5 µL of Supermix (contains dNTPs, Taq DNA polymerase, SYBR Green I, and fluorescein), 250 nM forward primer, 250 nM reverse primer, and 1.6 µL RT-PCR products. Melting curve analysis and agarose gel electrophoresis were performed after real-time PCR reaction to monitor PCR specificity, wherein PCR products were detected with SYBR Green I using the iQ SYBR Green Supermix kit (Bio-Rad).

Quantifying the relative expression of real-time PCR was performed using the 2-ΔΔCt method (Livak & Schmittgen, 2001, *Methods* 25:402-8), and a general linear model was employed to fit the expression data. The PROC GLM procedure in SAS (version 8.2; SAS Institute, Cary, N.C.) was used to estimate least squares means in expression between treated and untreated hESCs and $P<0.05$ was considered statistically significant Real-time PCR was conducted on samples from 24 hours (24 H), 4 days (4 D) and 8 days (EC) after VPA treatment to investigate expression levels of epigenetic regulators (such as DNA methyltransferase-1, DNMT-1, BMI-1, EED) and critical transcription factors responsible for embryonic patterning and neurodevelopment (RUNX2, BMP7, FGF8, CBX2, GLI3, SSH and SP8) in human embryonic stem cells. These experiments showed hESCs treated with VPA were subject to marked changes in their transcriptional activity following teratogen treatment. VPA induced overall marked (2 to 30 fold) downregulation of transcription levels as early as 24 hours after exposure in all genes tested (with the exception of DNMT-1 and Shh). At 4 days after treatment, however, expression of the ubiquitous DNA methyltransferase-1 was almost abolished, and sonic hedgehog, which is absolutely critical for neurogenesis (Ye et al., 1998, *Cell* 93:755-66), was down-regulated five-fold in comparison to untreated controls. At 8 days after VPA treatment, the majority of the genes were upregulated in comparison to untreated controls.

These results embodied two major implications for developmental toxicology. First, VPA induced persistent changes in key epigenetic modulators that also participate in differentiation of other tissues, such as DNMT-1 and the polycomb family member EED. Second, the effects of teratogens persisted in hESCs during critical stages of neurogenesis and organogenesis. For example, genes whose expression was affected as shown herein (including sonic hedgehog and FGF-8) are known to be master regulators of differentiation of serotonergic neurons in the brain (Ye et al., 1998, *Cell* 93:755-66). Of particular notice is the fact that DNMT-1 expression is almost abolished at four days after treatment. In vivo, disruption of this enzyme is lethal to embryos, since it is the major maintenance methyltransferase during DNA replication (Li et al., 1992, *Cell* 69:915-26).

Following teratogen exposure, temporal-specific alterations in developmental gene expression were observed. Developmental genes differ in their susceptibility to teratogens at different times. This indication may be critical to understanding specificity of epigenetic disruptors on certain organs or tissues. RUNX2, for example, is a transcriptional activator of bone development (Napierala et al., 2005, *Mol Genet Metab* 86:257-68), and is more sensitive to VPA-mediated up-regulation at very early or late stages following exposure. Real-time PCR results from hESCs disclosed herein were correlated to previous findings in vivo in mice (Okada et al., 2004, *Birth Defects Res A Clin Mol Teratol* 70:870-879) and rats (Miyazaki et al., 2005, *Int J Devl Neuroscience* 23:287-97). In these animal studies, VPA inhibited the expression of Polycomb genes, Eed, Bmil and Cbx2 and induced downregulation of Shh while FGF8 levels remained unchanged. The results shown here at four days following VPA treatment (Table 2) were consistent with these observations using other developmental model systems.

TABLE 2

1 mM VPA treatment resulted in marked changes in the expression of epigenetic regulators and developmental genes that are critical for embryonic patterning and differentiation of neurons.

| Gene | 1-24 H control | 2-24 H VPA treated | 3-4 D control | 4-4 D VPA treated | 5-EC control | 6-EC VPA treated |
|---|---|---|---|---|---|---|
| BMI-1 | 0.543 | 0.252 | 1.651 | 0.112 | 1.020 | 1.071 |
| DNMT1 | 0.664 | 0.624 | 1.742 | 0.002 | 0.731 | 1.124 |
| EED | 0.757 | 0.342 | 1.501 | 0.185 | 1.381 | 1.769 |
| H19 | 0.207 | 0.006 | 0.144 | 0.846 | 10.660 | 2.756 |
| RUNX2 | 0.325 | 1.769 | 5.198 | 4.020 | 1.177 | 2.434 |
| BMP7 | 0.511 | 0.093 | 0.397 | 0.342 | 0.731 | 1.664 |
| FGF8 | 2.544 | 0.801 | 0.384 | 0.314 | 0.16 | 0.837 |
| CBX2 | 1.113 | 0.245 | 1.221 | 1.1881 | 0.81 | 1.946 |
| GLI3 | 0.202 | 0.015 | 0.016 | 0.774 | 0.950 | 1.918 |
| Shh | 0.562 | 0.562 | 2.772 | 0.533 | 1.369 | — |
| SP8 | 0.49 | 0.235 | 0.25 | 1.703 | 2.132 | 5.808 |

Gene expression levels are relative to a housekeeping gene (target gene/Beta-2-Microglobulin).

Example 3

Figure 5:
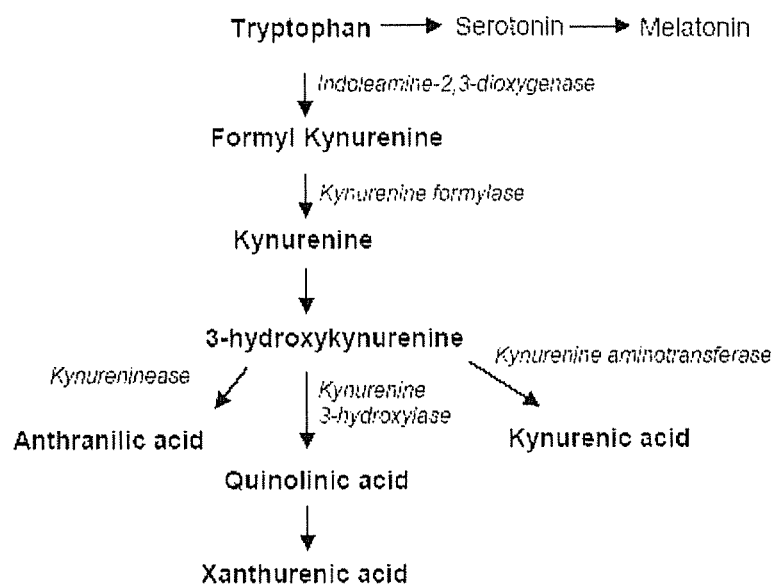
FIG. 5 represents the kynurenine metabolism pathway of tryptophan in humans (Wang et al., 2006, *J Biol Chem* 281: 22021-22028, published electronically on Jun. 5, 2006).

Human Embryonic Stem Cell Metabolome: Metabolite Profiles Following Teratogen Exposure Exposure of hES cells to the teratogen valproate induced significant changes in different metabolic pathways, including pathways important during pregnancy and development. An alternative metabolic pathway activated during pregnancy are shown in FIG. 5, wherein tryptophan is converted to kynurenine. To investigate this aspect of the invention, hESCs were cultured as described in Example 1, and the procedure for valproate treatment was performed as described therein. Treatment 1 (24 hours) exposed hES cells to 22 µM valproate for 24 hours followed by collection of supernatant and cell pellets. In the second treatment group (4 days), hES cells were exposed to 22 µM valproate for 4 days and harvested on day 4. In the third treatment or extended culture (EC, 8 days), hES cells received valproate for 4 days followed by culture in standard hES cell media for an additional four days. Cells and supernatant were harvested on day eight. Each treatment had a parallel control group with a total of six 6-well culture dishes per experiment (two 6-well culture dishes per treatment).

Figure 4A:
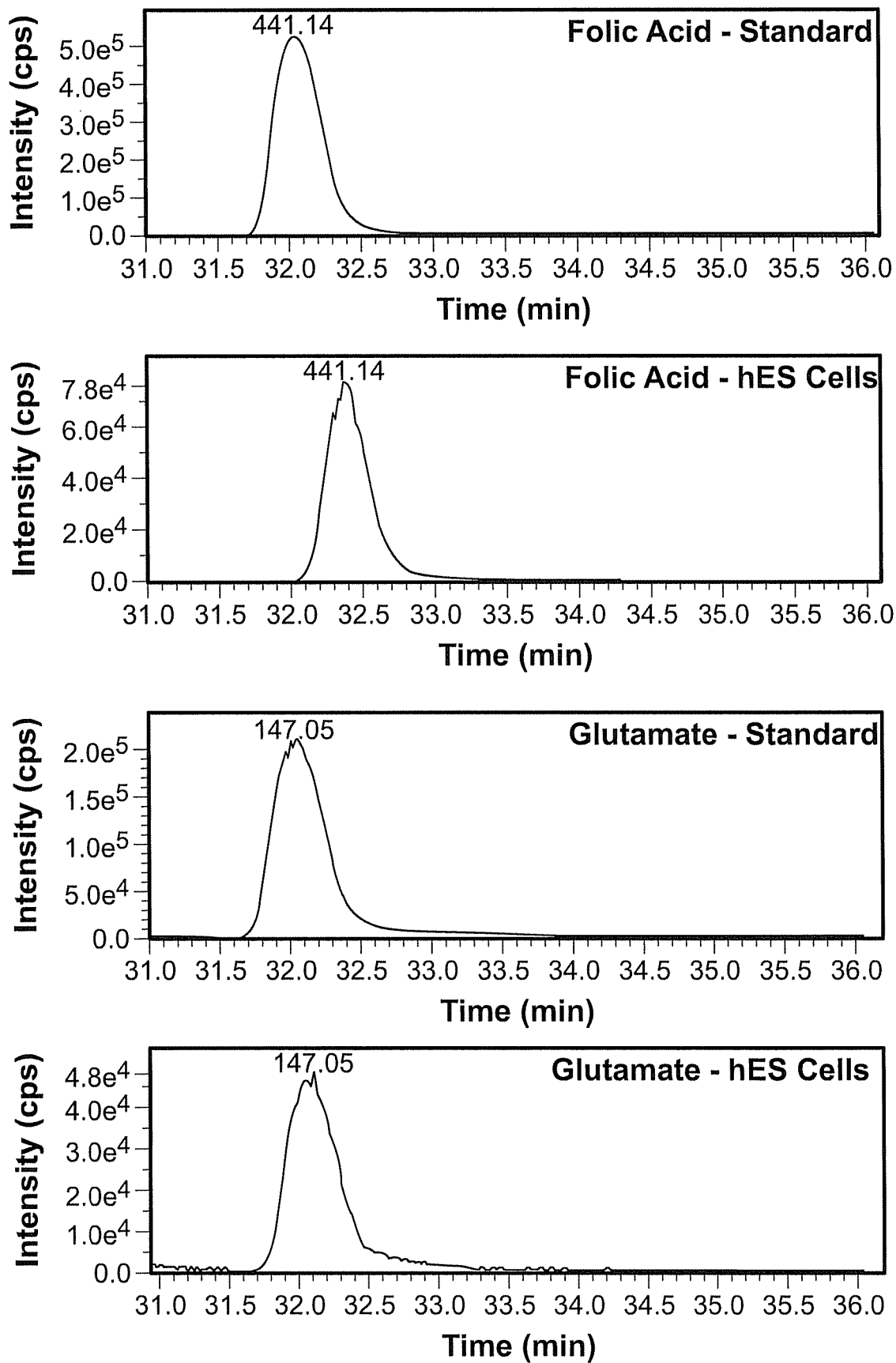
FIG. 4 shows the results of comparative mass spectrometry in the presence of chemical standards confirming the chemical identity of folic acid (exact mass 441.14), pyroglutamic acid (exact mass 129.04), glutamate (exact neutral mass 147.05) and kynurenine (exact mass 208.08).
Figure 4B:
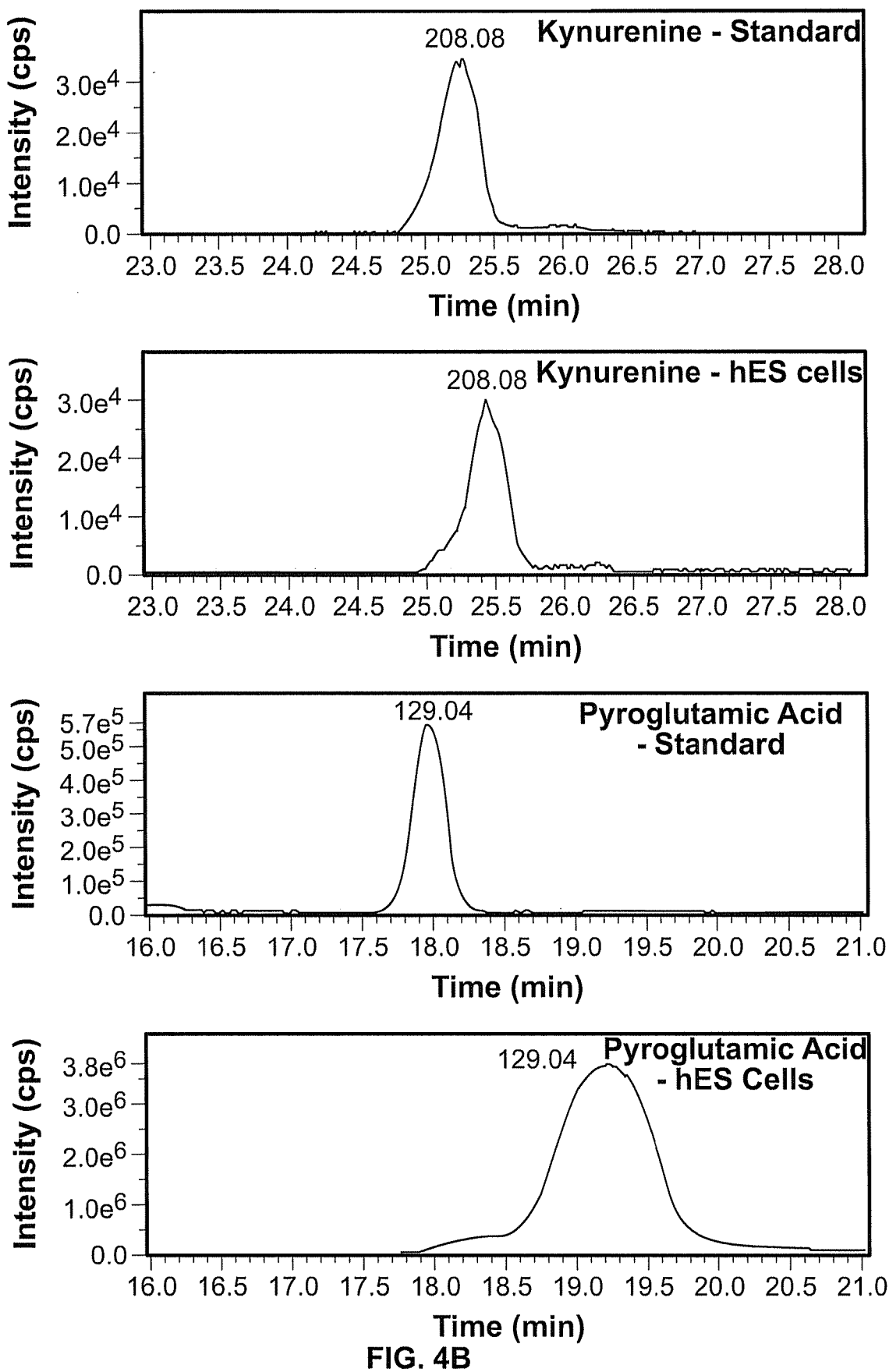

Metabolome analysis was performed as described in Example 1 (Wu and McAllister, 2003, *J Mass Spectrom* 38:1043-53). Complex mixtures were separated by liquid chromatography (LC) prior to electrospray ionization (ESI) time of flight (TOF) mass spectrometry according to the methods described in this Example and Example 1. Mass Hunter (Agilent) software was applied to deconvolute the data and determine the abundance of each mass. Data were extracted from the entire mass spectrum using the m/z range of 0 to 1500 and the top 2 million most abundant mass peaks from each sample were used for data deconvolution. The minimum signal-to-noise ratio was set to 5. The masses with a minimum relative abundance greater than 0.1% were exported from the Mass Hunter software and used for further analysis.

hESCs treated with 22 µM valproate resulted in 3,241 detected mass signals 42 injections. Of the total of 3,241 mass signals detected in these experiments, 1,963 compounds were measured solely in hES cells and 1,278 compounds were also present in conditioned media; 443 of these were only measured in 1 of 42 injections. 110 compounds (3%) had statistically-significant differences in at least one time point in valproate-treated hESCs compared with control. Fold changes as high as seven- to thirteen-fold were measured after valproate treatment, but these mass signals exhibited high variability across experiments. Representative masses identified following treatment of cells with 1 mM and 22 µM VPA are summarized in Tables 3 and 4, respectively. Several peaks (1,963) were detected in hES cells but not in conditioned media. One of these small molecules was kynurenine, a compound produced by an alternative tryptophan metabolic pathway, activated during pregnancy and immune response. The levels of kynurenine increased by 44% (p value=0.004 at four days, Table 5) following valproate treatment. Kynurenine was detected exclusively in hES cells and absent in conditioned media. The chemical identity of this peak was confirmed by comparative mass spectrometry in the presence of the chemical standard (FIG. 4).

The results of these experiments suggested that kynurenine is a candidate biomarker for neurodevelopmental disorders, in particular those originated by exposure of the human embryo to anti-epileptic drugs such as VPA (Ornoy et al., 2006, *Reproductive Toxicol* 21:399-409). Strikingly, recent studies have suggested that kynurenine metabolism may be a novel target for the mechanism of action of anti-epileptic drugs (Kocki et al., 2006, *Eur J Pharmacol* 542:147-51). Cognitive and behavioral disorders are known adverse effects of antiepileptic exposure during pregnancy. Tryptophan is the precursor of serotonin, a key neurotransmitter in the pathogenesis of these and other diseases, such as depression. In addition, increased plasma levels of kynurenine have been linked to postpartum depression (Kohl et al., 2005, *J Affect Disord* 86:135-42). The alteration in tryptophan metabolism detected herein is a means for examining novel mechanisms in pathogenesis of serotonin-related behavioral disorders such as autism (Chugani, 2004, *Ment Retard Dev Disabil Res Rev* 10:112-116). An increase in kynurenine levels during development may reduce the bioavailability of tryptophan and consequently serotonin, leading to cognitive dysfunction.

Glutamate and pyroglutamic acid were also elevated in hESCs treated with valproate. Glutamate and pyroglutamic acid were elevated in response to valproate (20% and 27%, respectively), although only pyroglutamic acid exhibited statistically significant changes (p=0.021 at 4 days, FIGS. 3A through 3D). Glutathione (GSH) is metabolized by gamma-glutamyltranspeptidase into glutamate, a neurotransmitter of NMDA receptors, and cysteinylglycine (Cys-Gly). Glutathione (exact neutral mass 612.15) and S-adenosyl-homocysteine (exact neutral mass 384.12) were detected at very low levels in comparison to other mass signals (data not shown). For these experiments for low level detection, small molecules were identified by comparative ESI-TOF-MS with chemical standards that were "spiked" into conditioned media at different concentrations and used to confirm neutral exact masses and retention times of experimental mass signals (FIGS. 3A through 3D). Neutral exact masses and/or empirical chemical formulas generated by ESI-TOF-MS were searched in public databases (including, for example, metlin.scripps.edu., www.nist.gov/srd/chemistry.htm, www-.metabolomics.ca) for candidate compounds.

These results suggested that valproate affects the glutamate synthesis pathway in the developing human embryo. The affinity of anti-epileptic drugs towards glutamate targets has been previously suggested (Rogawski and Loscher, 2004, *Nat Rev Neurosci* 2004 5:553-64). Abnormal levels of glutamate metabolites were measured in maternal serum and amniotic fluid of pregnant women whose infants were diagnosed with spina bifida (Groenen et al., 2004, *Eur J Obstet Gynecol Reprod Biol.*; 112:16-23) with nuclear magnetic resonance (NMR). The levels of glutamine and hydroxyproline were significantly higher in NTDs, and as a result the hESC methods provided herein provide a robust resource to model in vivo alterations of development.

Table 5. Changes in metabolic profiles of four compounds in hES cells treated with valproate versus untreated controls at 24 hours (24 h), 4 days (4 D), and eight days (8 D) after treatment.

The amino acid tryptophan (TRP) is a precursor of the neurotransmitter serotonin, a key mediator of numerous CNS disorders, such as depression, neurodegeneration and cognitive impairment. Tryptophan catabolism into kynurenic acid is an alternative route for tryptophan metabolism (FIG. 5), that is activated in specific circumstances such as inflammatory response or pregnancy. Up-regulation of the kynurenine pathway is correlated with psychosis in adult diseases such as schizophrenia and bipolar disorder, an indication that increased levels of pathway intermediates may trigger psychotic features (Miller et al., 2006, *Brain Res* 16:25-37). Significantly, metabolism using the kynurenine pathway is accompanied by decreased tryptophan metabolism using the serotonin pathway (in the absence of exogenous tryptophan, an essential amino acid not synthesized by mammals including man). An increase in kynurenine levels during development can reduce the bioavailability of tryptophan and consequently serotonin, leading to cognitive dysfunction.

In addition, kynurenic acid (KYNA), one of the end products of this tryptophan metabolic pathway, is an antagonist of glutamate neurotransmission and N-methyl-D-aspartate (NMDA) receptors. Recent studies have demonstrated that kynurenic acid is a druggable target via its role in the activation of the previously orphan GPCR receptor GPR35 (Wang et al., 2006, *J Biol Chem* 281:22021-8). Quinolinic acid (QUIN), another end product of the pathway (FIG. 5), and 3-hydroxy-kynurenine, an intermediate, act as neurotoxicants (Guillemin et al., 2005, *J Neuroinflammation* 26:16; Chiarugui et al., 2001, *J Neurochem* 77:1310-8). QUIN is involved in the pathogenesis of Alzheimer's disease where its neurotoxicity may be involved in increased inflammation and in convulsions by interacting with the N-methyl-D-aspartate (NMDA) receptor complex, a type of glutamate receptor

TABLE 5

Changes in metabolic profiles of four compounds in hES cells treated with valproate versus untreated controls at 24 hours (24 h), 4 days (4 D), and eight days (8 D) after treatment.

| Molecule | 24 h P-value | 24 h fold | 4 D P-value | 4 D fold | 8 D P-value | 8 D fold | Mass | RT |
|---|---|---|---|---|---|---|---|---|
| Pyroglutamic acid | 0.242 | 57% decrease | 0.021 | 27% increase | 0.917 | 3% decrease | 129.0426 | 19.9 |
| Folic acid | 0.638 | 3% increase | 0.626 | 4% increase | 0.022 | 16% increase | 441.1395 | 32.7 |
| Glutamate | 0.969 | 1% increase | 0.108 | 24% increase | 0.651 | 10% increase | 147.0535 | 20.0 |
| Kynurenine | 0.087 | 29% increase | 0.004 | 44% increase | N.D. | N.D. | 208.0850 | 25.9 |

RT = retention time
Fold changes are represented as percent difference of the least squared means of valproate treated and untreated hES cells. p-values were determined by ANOVA. The mass is the average neutral mass detected by ESI-TOF-MS and the RT is the average retention time the molecule eluted at. P-values less than 0.05 are in bold.

Example 4

Kynurenine: Biomarker for Diagnosis and Treatment of Developmental Toxicity and CNS Disorders Kynurenine was shown in Example 3 to be detected in valproate-treated hES cells. Kynurenine (along with glutamate and pyroglutamic acid) was differentially produced in valproate-treated human embryonic stem cells (hES) versus controls. Kynurenine is a novel biomarker useful for the identification of neurodevelopmental disorders in infants and in vitro developmental toxicity of chemicals. This example describes the identification of biomarkers for neurodevelopmental disorders, including cellular products differentially produced in teratogen-treated hESCs.

(Guillemin et al., 2002, *J Neuroinflammation* 26:16; Nemeth et al., 2005, *Curr Neurovasc Res* 2:249-60). Kynurenin (KYN), another pathway intermediate, is synthesized in the brain and is transported across the blood-brain barrier (Nemeth et al., 2005, *Curr Neurovasc Res* 2:249-60). KYN is metabolized to the neurotoxic quinolinic acid (QUIN) and the neuroprotective kynurenic acid (KYNA) (FIG. 5). Increased serum levels of KYN have been correlated to clinical manifestation of depression with different etiologies, such as postpartum disorder (Kohl et al., 2005, *J Affect Disord* 86:135-42) and interferon-alpha treatment (Capuron et al., 2003, *Biol Psychiatry* 54:906-14).

Exposure of hES cells to valproate, a disruptor of human development, induced significant changes in different metabolic pathways, including the production of kynurenine (exact neutral mass 208.08), which was significantly upregulated in response to valproate as detected by liquid chromatography electrospray ionization time of flight mass spectrometry (LC/ESI-TOF-MS) as described in Example 4. Additionally, novel chemical entities, having exact neutral masses of 328.058, 336.163, 343.080, were detected and are not yet catalogued in public databases.

When neural precursors derived from hESCs were exposed to 1 mM valproate, a marked decrease in both serotonin (176.0946) and indoleacetaldehyde (159.0689), a downstream sub-product of serotonin generated by monoaminoxoidase activity (MAO) was observed (Table 6). Glutamate and pyroglutamic acid or hydroxyproline (p=0.021) were also elevated in hES cells treated with valproate. These results suggest that valproate affects the glutamate synthesis pathway in the developing human embryo. This finding emulates in vivo neurophysiology, where compounds from the kynurenine pathway modulate activity at NMDA glutamate receptors and produce epileptic phenotypes, including seizures (Perkins and Stone, 1982, *Brain Res* 247:184-187.).

As a consequence of the identification of kynurenine herein, chemical inhibitors of kynurenine synthesis can be used as novel therapeutics in mood disorders; for example, small molecules that antagonize indoleamine 2,3-dioxygenase (IDO) or kynurenine formylase activities, which converts tryptophan (TRP) into kynurenine (KYN). Inhibition of TRP catabolism to KYN can be used to ameliorate disease symptoms in cognitive and neurodegenerative disorders by increasing serotonin levels, via elevated synthesis of this neurotransmitter or reduced depletion through the kynurenine pathway.

Figure 6:
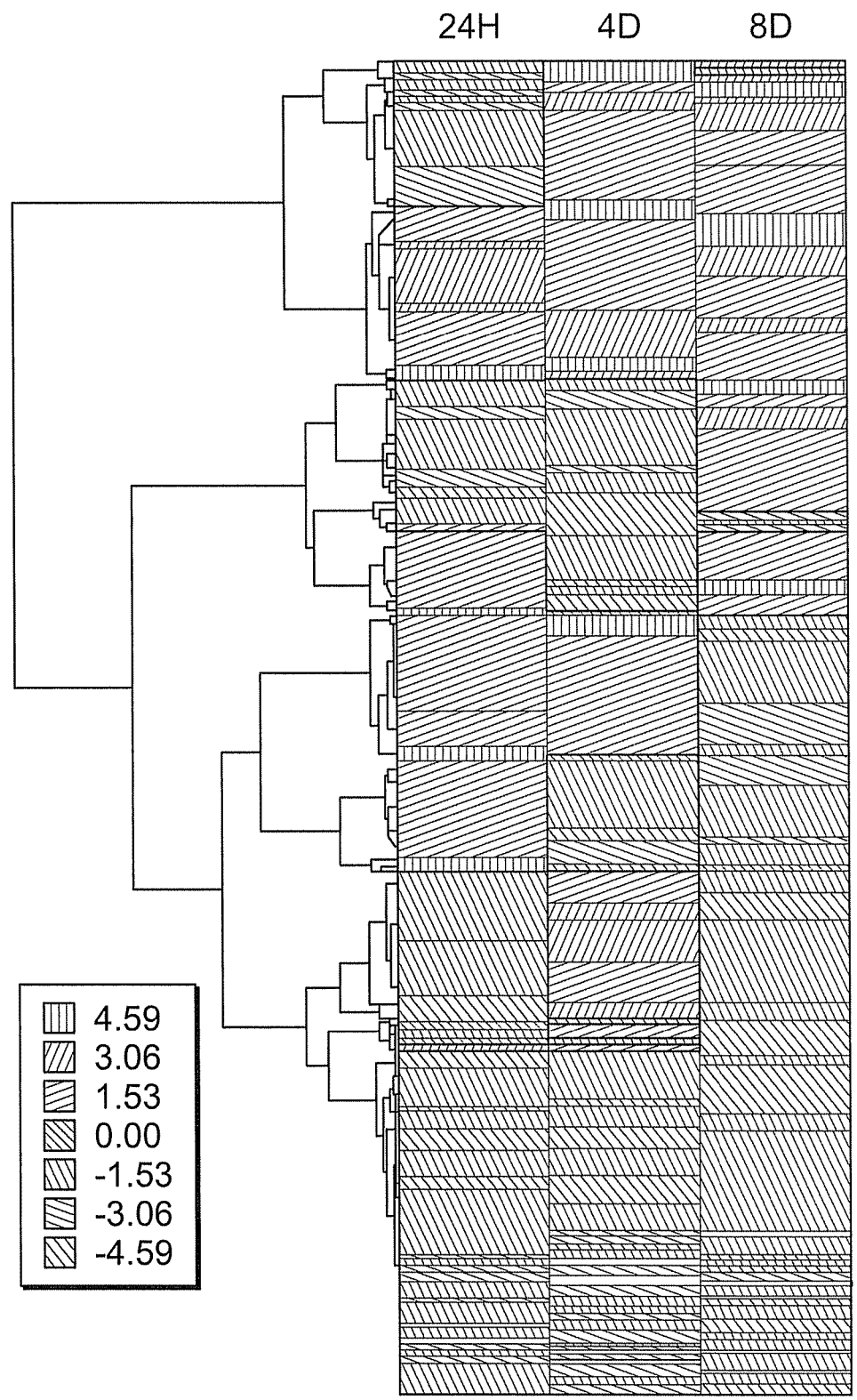
FIG. 6 illustrates a hierarchical clustering of fold-change differences from 22,573 unique masses and is representative of multiple independent experiments in which hESCs and neural precursors produced from hESCs were treated with 1 mM valproate. Non-embryonic cells (human fibroblasts) were used as controls (data not shown). Positive fold changes are red, negative fold changes are green, and missing data is grey.

Collectively, the metabolite changes detected in hES cells in response to valproate converge functionally towards folate, kynurenine and glutamate pathways. FIG. 6 illustrates the hierarchical clustering of the fold change differences from 22,573 unique masses. Changes in the above-mentioned pathways were consistent and reproducible in multiple independent studies of 1 mM VPA treated hESCs, and neural precursors produced from hESCs (FIG. 6).

Example 5

Gene Expression Analysis of Kynurenine Pathway

The efficacy of the analysis in Example 4 was confirmed by gene expression studies, wherein changes in gene expression were observed following VPA treatment of hESC. Valproate treatment of human embryonic stem cells induced a marked upregulation in the small molecule kynurenine, an intermediate metabolite in the catabolism of tryptophan. Tryptophan is the precursor of the neurotransmitter serotonin (5HT). Thus, whether expression of enzymes in the metabolism of tryptophan to kynurenine and its opposite route, serotonin synthesis, was altered in human embryonic stem cells was investigated to examine the mechanistic properties of the kynurenine pathway and its response to valproate.

Human embryonic stem cells treated with 1 mM valproate and untreated controls were harvested at four days after treatment and stored at −80° C. prior to RNA isolation using RNeasy (Qiagen). 5 µg of RNA templates were reverse transcribed and amplified (QIAGEN OneStep RT-PCR) according to the manufacturer's instructions using primers designed for transcribed human sequences of the following genes: INDO, indoleamine 2,3 dioxygenase, TDO or TDO2, tryptophan 2,3-dioxygenase, AFMID, arylformamidase, TPH1, tryptophan hydroxylase the rate-limiting enzyme in serotonin biosynthesis, AADAT, aminoadipate aminotransferase, KYNU, kynunreninase, KMO, kynurenine 3-monooxygenase, GAPDH, glyceraldehyde 3-phosphate dehydrogenase.

Figure 7:
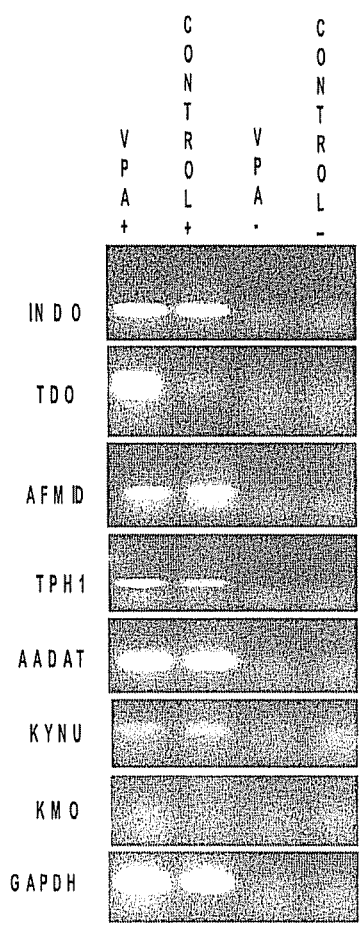
FIG. 7 shows the relative expression of enzymes in the kynurenine and serotonin synthesis pathways in hES cells. INDO, indoleamine 2,3 dioxygenase, TDO or TDO2, tryptophan 2,3-dioxygenase. (TDO2 was upregulated in valproate-treated hES cells in comparison to controls.) AFMID, arylformamidase, TPH1, tryptophan hydroxylase, AADAT, aminoadipate aminotransferase, KYNU, kynunreninase, GAPDH, glyceraldehyde 3-phosphate dehydrogenase, housekeeping control gene. KMO, kynurenine 3-monooxygenase, was not expressed in valproate-treated cells or controls.

The results of this study showed that the majority of enzymes in the kynurenine pathway and serotonin synthesis were expressed in hES cells at four days after treatment of hES cells with 1 mM valproate (FIG. 7). Indoleamine 2,3 dioxygenase INDO, catabolizes tryptophan into the kynurenine pathway, and produces kynurenine as an end product. The expression of tryptophan 2,3 dioxygenase (TDO or TDO2) was also examined. TDO2, like INDO, catalyzes the first step in the kynurenine pathway. These data suggested that TDO2 expression was upregulated in hES cells treated with valproate in comparison to untreated controls. The rate limiting enzyme in 5HT synthesis, TPH1, was also expressed in hES cells (FIG. 7). Expression of these enzymes supported the conclusion that hES cells recapitulate metabolic pathways of tryptophan catabolism and serotonin synthesis. Interestingly, VPA induced pronounced expression of rate-limiting enzymes in this pathway.

Example 6

Developmental Toxicology Screening for Prenatal Alcohol Exposure

To identify differentially secreted metabolites in response to alcohol, as well as the pathways involved in fetal alcohol syndrome, human embryonic stem cells were treated with 0, 0.1 and 0.3% ethanol for four days followed by LC/ESI-TOF mass spectrometry according to the general methods described above for valproate in Example 1. Extracellular media was collected and processed at 24 hours and four days after treatment, and 49,481 mass signals were detected following three technical replications. Of the 49,481 mass signals, 1,860 compounds were significantly different (p<0.05) in at least one treatment and had a significant time change (<1 or >1). (Table 7). Binned masses were annotated in silico by querying the neutral masses in several different databases. These databases included Metlin, Biological Magnetic Resonance Data Bank (BMRB), NIST Chemistry WebBook, and the Human Metabolome Database. A mass was considered identified when its neutral mass was within 10 ppm of a known compound annotated in one of the databases listed above.

The putative kynurenine compound (measured exact neutral mass 208.0816) was upregulated three-fold at day four, but not 24 hours, in both treatments (0.1%, p=0.001 and 0.3% p=0.002, respectively). Another putative metabolite in the kynurenine pathway, 8-methoxykynurenate (219.0532) was also upregulated at four days in response to both 0.1% and 0.3% alcohol treatment (p<0.05). The analysis also detected a significant downregulation of 5-hydroxy-L-tryptophan (220.0848) at four days following 0.3% alcohol treatment (p<0.05) in comparison to untreated controls. 5-hydroxy-L-tryptophan is the only intermediate metabolite between tryptophan and serotonin and its synthesis is mediated by tryptophan hydroxylase, the rate limiting enzyme in serotonin synthesis. These results suggest that alcohol exposure during human development can affect serotonin bioavailability due to upregulation of tryptophan catabolism into kynurenines. In addition, alcohol exposure induced significant changes in metabolic pathways and small molecules involved in neural development such as glutamate, gabapentin, adrenaline and glutathione.

Example 7

Developmental Toxicology Screening of Neuronal Precursor Cells

Metabolomic assessment of teratogens on embryonic development is not limited exclusively to hESCs. The methods of the invention are also useful with other progenitor stem cells, including lineage-restricted stem cells such as neural precursor cells. To illustrate the efficacy of toxicology screening on lineage-specific stem cells, neuronal precursors derived from hESCs were treated with 1 mM valproate according to the methods described in Example 1.

Approximately 135 compounds were differentially secreted in VPA-treated neuronal precursors versus control. (See Table 6). The results of this study illustrated that the methods of the invention reveal alterations in the metabolic profile of lineage-specific stem cells in response to teratogen exposure.

The results disclosed herein are set forth in the following tables

TABLE 3

Cellular metabolites measured in human embryonic stem cells treated with 1 mM of valproate

| EXP | RT | roundMASS | time | trt | Fold | Probt | annotation.1 | annotation.2 |
|---|---|---|---|---|---|---|---|---|
| 1 mM VPA | 8.31910526 | 103.056358 | 4 D | 1 mM VPA | 1.987286671 | 0.01734377 | gamma-Aminobutryic acid | |
| 1 mM VPA | 6.78779869 | 103.098349 | 4 D | 1 mM VPA | 2.143101233 | 0.00047552 | 2-Aminoisobutyric acid | |
| 1 mM VPA | 8.39854546 | 113.082093 | 4 D | 1 mM VPA | 16.4054129 | 0.01342684 | 1-Pyrroline-5-carboxylic acid | |
| 1 mM VPA | 11.7534444 | 120.043328 | 4 D | 1 mM VPA | 1.355758298 | 0.03951319 | 3,4-Dihydroxybutyric acid | |
| 1 mM VPA | 85.7330833 | 121.088708 | 24 H | 1 mM VPA | 10.30519572 | 0.02442001 | Phenylethylamine | |
| 1 mM VPA | 7.307128 | 122.071261 | 4 D | 1 mM VPA | −2.2989897 | 0.01870947 | Unknown | |
| 1 mM VPA | 38.1047857 | 129.070626 | 8 D | 1 mM VPA | 3.023878137 | 0.03988213 | 2-Ketobutyric acid; 2-Oxobutyric acid; alpha-Ketobutyric acid; alpha-Ketobutyrate | |
| 1 mM VPA | 14.2761702 | 136.038753 | 8 D | 1 mM VPA | 2.696709281 | 0.00083818 | Hypoxanthine | Allopurinol |
| 1 mM VPA | 31.3610896 | 141.114252 | 8 D | 1 mM VPA | 1.865419366 | 0.02273706 | Unknown | |
| 1 mM VPA | 43.9201842 | 143.095482 | 8 D | 1 mM VPA | 2.064797071 | 0.03120757 | 1-Aminocyclohexanecarboxylic acid | |
| 1 mM VPA | 51.283453 | 144.113677 | 24 H | 1 mM VPA | 4.820891632 | 0.02775836 | Caprylic acid | Valproic acid |
| 1 mM VPA | 51.283453 | 144.113677 | 4 D | 1 mM VPA | 8.26720694 | 0.0011089 | Caprylic acid | Valproic acid |
| 1 mM VPA | 16.307931 | 147.068314 | 4 D | 1 mM VPA | −2.05380612 | 0.03872229 | 3-Methyloxindole | |
| 1 mM VPA | 16.307931 | 147.068314 | 24 H | 1 mM VPA | −1.80875876 | 0.037812 | 3-Methyloxindole | |
| 1 mM VPA | 22.5095926 | 153.079352 | 4 D | 1 mM VPA | −2.65737163 | 0.01268393 | Dopamine | |
| 1 mM VPA | 5.36288806 | 155.068364 | 8 D | 1 mM VPA | −1.34957018 | 0.0476914 | L-Histidine | |
| 1 mM VPA | 20.6395854 | 155.072941 | 4 D | 1 mM VPA | 3.82298622 | 0.00676609 | L-Histidine | |
| 1 mM VPA | 14.2071091 | 160.060653 | 8 D | 1 mM VPA | 12.348809 | 1.23E-06 | Unknown | |
| 1 mM VPA | 14.3670392 | 161.081539 | 8 D | 1 mM VPA | 4.777314979 | 0.0001252 | Unknown | |
| 1 mM VPA | 44.8165285 | 162.067353 | 4 D | 1 mM VPA | 1.640573238 | 0.01289447 | Unknown | |
| 1 mM VPA | 31.5154611 | 162.124096 | 24 H | 1 mM VPA | 1.911228139 | 0.01933211 | Unknown | |
| 1 mM VPA | 31.3624074 | 165.079533 | 8 D | 1 mM VPA | 1.705269784 | 0.00206584 | 4-(3-Pyridyl)-butanoic acid | |
| 1 mM VPA | 32.0426154 | 167.094942 | 8 D | 1 mM VPA | −2.20640862 | 0.01874726 | Methyldopamine | |
| 1 mM VPA | 20.0098065 | 173.083484 | 4 D | 1 mM VPA | 5.458861144 | 0.00198632 | 2-Oxoarginine | |
| 1 mM VPA | 15.3496532 | 177.082617 | 8 D | 1 mM VPA | 2.397781171 | 0.01291216 | Unknown | |
| 1 mM VPA | 24.1314286 | 179.094351 | 4 D | 1 mM VPA | 1.851635336 | 0.03464009 | Salsolinol | Homophenylalanine |
| 1 mM VPA | 21.8046482 | 187.064183 | 8 D | 1 mM VPA | 2.839427352 | 0.00590774 | Unknown | |
| 1 mM VPA | 21.8046482 | 187.064183 | 4 D | 1 mM VPA | 3.356831218 | 1.24E-05 | Unknown | |
| 1 mM VPA | 23.317 | 187.08492 | 4 D | 1 mM VPA | 3.781608467 | 0.03987705 | 6-Acetamido-3-oxohexanoate | |

TABLE 3-continued

Cellular metabolites measured in human embryonic stem cells treated with 1 mM of valproate

| EXP | RT | roundMASS | time | trt | Fold | Probt | annotation.1 | annotation.2 |
|---|---|---|---|---|---|---|---|---|
| 1 mM VPA | 27.7865556 | 189.042631 | 8 D | 1 mM VPA | 2.865724657 | 0.02214848 | Kynurenic acid | |
| 1 mM VPA | 61.5462473 | 196.090684 | 4 D | 1 mM VPA | 3.519815968 | 0.01102697 | Unknown | |
| 1 mM VPA | 24.0551398 | 197.105003 | 4 D | 1 mM VPA | 2.231478645 | 0.00076838 | L-Metanephrine | |
| 1 mM VPA | 20.0989286 | 197.175657 | 8 D | 1 mM VPA | 4.237754463 | 0.00034728 | Unknown | |
| 1 mM VPA | 73.9582188 | 198.16015 | 4 D | 1 mM VPA | 2.039619449 | 0.01232495 | 5-Dodecenoic acid | |
| 1 mM VPA | 29.2935714 | 201.100569 | 4 D | 1 mM VPA | 5.966976107 | 0.00328699 | Unknown | |
| 1 mM VPA | 28.6036393 | 203.115212 | 8 D | 1 mM VPA | 1.872544495 | 0.00040874 | L-Glutamic acid n-butyl ester | Acetylcarnitine |
| 1 mM VPA | 9.07926923 | 209.06985 | 8 D | 1 mM VPA | −12.4054314 | 0.01848957 | 4-Carboxyphenylglycine | |
| 1 mM VPA | 48.3434453 | 213.079468 | 8 D | 1 mM VPA | 2.512458907 | 0.02116099 | Unknown | |
| 1 mM VPA | 44.6001887 | 214.064259 | 4 D | 1 mM VPA | 1.446032522 | 0.02767084 | Unknown | |
| 1 mM VPA | 44.6001887 | 214.064259 | 8 D | 1 mM VPA | 1.783609761 | 0.00082206 | Unknown | |
| 1 mM VPA | 69.6687917 | 214.064356 | 24 H | 1 mM VPA | 1.316493137 | 0.0171064 | Unknown | |
| 1 mM VPA | 18.7504371 | 216.094569 | 4 D | 1 mM VPA | 2.349086763 | 0.01043169 | Unknown | |
| 1 mM VPA | 30.5773235 | 216.100485 | 4 D | 1 mM VPA | 2.050108123 | 0.04358571 | Unknown | |
| 1 mM VPA | 6.39474737 | 218.076897 | 4 D | 1 mM VPA | 1.737243521 | 0.02003307 | Unknown | |
| 1 mM VPA | 6.68071429 | 219.144891 | 24 H | 1 mM VPA | −1.58008262 | 0.02066251 | Unknown | |
| 1 mM VPA | 10.5609423 | 220.085746 | 4 D | 1 mM VPA | −2.39827983 | 1.63E−06 | 5-Hydroxytryptophan | |
| 1 mM VPA | 53.8814512 | 222.078039 | 4 D | 1 mM VPA | 2.882259036 | 0.02550855 | Unknown | |
| 1 mM VPA | 73.0997018 | 223.049411 | 8 D | 1 mM VPA | −4.31392173 | 0.04819747 | 7,8-Dihydro-7,8-dihydroxykynurenate | |
| 1 mM VPA | 6.45641791 | 229.095757 | 8 D | 1 mM VPA | 2.4471457 | 0.00094873 | Malonylcarnitine | |
| 1 mM VPA | 23.7927189 | 229.095855 | 4 D | 1 mM VPA | 2.057653416 | 0.00038761 | Malonylcarnitine | |
| 1 mM VPA | 55.5371429 | 229.145042 | 4 D | 1 mM VPA | 2.032140286 | 0.00236036 | Unknown | |
| 1 mM VPA | 19.9783175 | 229.164555 | 8 D | 1 mM VPA | 3.779774064 | 1.34E−08 | Unknown | |
| 1 mM VPA | 32.6065714 | 229.201979 | 4 D | 1 mM VPA | 3.088058322 | 0.00439209 | Unknown | |
| 1 mM VPA | 9.79255 | 230.080163 | 4 D | 1 mM VPA | −1.383766 | 0.02197836 | Unknown | |
| 1 mM VPA | 7.80846914 | 233.123128 | 8 D | 1 mM VPA | 6.784300156 | 0.00043647 | Unknown | |
| 1 mM VPA | 14.3537949 | 236.080213 | 4 D | 1 mM VPA | −3.35334287 | 0.00032832 | N'-Formylkynurenine | |
| 1 mM VPA | 45.2867439 | 238.12327 | 8 D | 1 mM VPA | 3.718961983 | 0.01466842 | 2-Amino-3-methylbutyric acid | |
| 1 mM VPA | 12.1171264 | 244.109135 | 4 D | 1 mM VPA | 1.659329044 | 0.01962434 | Unknown | |
| 1 mM VPA | 12.127642 | 245.119507 | 4 D | 1 mM VPA | 2.061936638 | 0.02383097 | Unknown | |
| 1 mM VPA | 19.8036863 | 246.100428 | 4 D | 1 mM VPA | 4.924577653 | 0.02636633 | N-Acetyl-D-tryptophan | |
| 1 mM VPA | 8.947 | 247.140975 | 8 D | 1 mM VPA | 2.877468231 | 0.01777412 | Unknown | |
| 1 mM VPA | 19.7590488 | 247.173942 | 8 D | 1 mM VPA | 3.071620539 | 3.15E−06 | Unknown | |
| 1 mM VPA | 48.7837308 | 248.191881 | 4 D | 1 mM VPA | 2.692786782 | 0.00724013 | Unknown | |
| 1 mM VPA | 8.00665714 | 249.119037 | 4 D | 1 mM VPA | 1.948008537 | 0.01865508 | Unknown | |
| 1 mM VPA | 53.1723271 | 256.1093 | 8 D | 1 mM VPA | 3.068428571 | 0.00024804 | D-2-Amino-3-hydroxybutyric acid | gamma-Amino-beta-hydroxybutyric acid |
| 1 mM VPA | 23.22678 | 257.099256 | 8 D | 1 mM VPA | 2.601240877 | 0.00033049 | 5-Methylcytidine | |

TABLE 3-continued

Cellular metabolites measured in human embryonic stem cells treated with 1 mM of valproate

| EXP | RT | roundMASS | time | trt | Fold | Probt | annotation.1 | annotation.2 |
|---|---|---|---|---|---|---|---|---|
| 1 mM VPA | 5.57045 | 257.891738 | 24 H | 1 mM VPA | −1.17015529 | 0.01640996 | Unknown | |
| 1 mM VPA | 7.08067539 | 258.019715 | 24 H | 1 mM VPA | 1.315125063 | 0.02206679 | Unknown | |
| 1 mM VPA | 22.8759189 | 258.121153 | 4 D | 1 mM VPA | 1.510263204 | 0.01588551 | Unknown | |
| 1 mM VPA | 28.8676889 | 258.133722 | 24 H | 1 mM VPA | 5.578974665 | 0.03000729 | Unknown | |
| 1 mM VPA | 47.6525584 | 258.133727 | 4 D | 1 mM VPA | −1.91733177 | 0.01442461 | Unknown | |
| 1 mM VPA | 18.7499759 | 259.11867 | 4 D | 1 mM VPA | 1.504620863 | 0.02037249 | N-(gamma-L-Glutamyl)amino-D-proline | |
| 1 mM VPA | 13.2221957 | 260.083648 | 8 D | 1 mM VPA | 2.984522231 | 0.02760558 | Unknown | |
| 1 mM VPA | 22.373 | 264.109282 | 4 D | 1 mM VPA | −1.74811488 | 0.01791457 | Acetyl-N-formyl-5-methoxykynurenamine | |
| 1 mM VPA | 58.8093824 | 265.132541 | 8 D | 1 mM VPA | 2.363623094 | 0.03359569 | (2R,3S)-rel-2,3-dihydroxy-- Butanoic acid | |
| 1 mM VPA | 27.779593 | 271.112691 | 4 D | 1 mM VPA | 1.685060044 | 0.03867385 | Unknown | |
| 1 mM VPA | 24.7259575 | 272.124009 | 4 D | 1 mM VPA | 2.036511555 | 0.02960407 | Unknown | |
| 1 mM VPA | 44.0582051 | 272.168272 | 8 D | 1 mM VPA | 2.056227653 | 0.00325332 | Unknown | |
| 1 mM VPA | 41.65612 | 272.211662 | 8 D | 1 mM VPA | −5.12943527 | 0.00643051 | 3-Oxo-delta1-steroid | |
| 1 mM VPA | 39.378469 | 273.105953 | 4 D | 1 mM VPA | 2.674742484 | 0.00030929 | Unknown | |
| 1 mM VPA | 8.93373171 | 276.136639 | 4 D | 1 mM VPA | 5.215118375 | 0.0006752 | Unknown | |
| 1 mM VPA | 67.6599775 | 280.237772 | 24 H | 1 mM VPA | 2.086232575 | 0.04410145 | Linoleic acid | Octadecadienoic acid |
| 1 mM VPA | 14.2211017 | 281.125398 | 8 D | 1 mM VPA | 8.170361997 | 1.56E−06 | 1-Methyladenosine | |
| 1 mM VPA | 71.5568571 | 282.225649 | 4 D | 1 mM VPA | 4.282045127 | 0.00101203 | Unknown | |
| 1 mM VPA | 72.7757434 | 282.253397 | 8 D | 1 mM VPA | −1.86257691 | 0.03054583 | Oleic acid | Elaidic acid |
| 1 mM VPA | 59.4208378 | 284.19613 | 4 D | 1 mM VPA | 5.253576839 | 0.0351483 | Unknown | |
| 1 mM VPA | 5.70108824 | 284.980449 | 4 D | 1 mM VPA | 1.366608495 | 0.03819988 | Unknown | |
| 1 mM VPA | 6.9018125 | 285.140063 | 4 D | 1 mM VPA | 15.96344365 | 0.00293691 | Unknown | |
| 1 mM VPA | 64.3362162 | 286.186749 | 4 D | 1 mM VPA | 2.524154118 | 0.04701735 | N-Acetyl-leucyl-leucine | |
| 1 mM VPA | 64.3362162 | 286.186749 | 24 H | 1 mM VPA | 2.577549261 | 0.00532464 | N-Acetyl-leucyl-leucine | |
| 1 mM VPA | 75.3938769 | 288.263273 | 4 D | 1 mM VPA | 2.556553115 | 0.0003234 | Unknown | |
| 1 mM VPA | 26.6263806 | 289.137569 | 8 D | 1 mM VPA | 7.105814367 | 0.00077408 | Unknown | |
| 1 mM VPA | 15.0419293 | 289.139413 | 8 D | 1 mM VPA | 3.953690666 | 0.00671585 | Unknown | |
| 1 mM VPA | 15.8950204 | 295.128678 | 8 D | 1 mM VPA | 2.286752138 | 1.23E−06 | N6,N6-Dimethyladenosine | |
| 1 mM VPA | 6.02850649 | 301.172858 | 4 D | 1 mM VPA | 5.302600282 | 0.00165331 | Unknown | |
| 1 mM VPA | 59.5394364 | 301.222733 | 4 D | 1 mM VPA | 4.091131755 | 0.01328711 | Unknown | |
| 1 mM VPA | 72.4551579 | 304.237816 | 8 D | 1 mM VPA | −5.09223853 | 0.00158305 | Arachidonic acid | |
| 1 mM VPA | 44.6849231 | 305.936181 | 8 D | 1 mM VPA | 2.13864941 | 0.00372138 | 3-Iodo-4-hydroxyphenylpyruvate | |
| 1 mM VPA | 7.93489796 | 306.092269 | 24 H | 1 mM VPA | −2.59907813 | 0.00116532 | Unknown | |
| 1 mM VPA | 22.339 | 306.121765 | 24 H | 1 mM VPA | 2.666042908 | 0.00540921 | Z-Gly-Pro; Z-Gly-Pro-OH | |
| 1 mM VPA | 59.461 | 306.180711 | 4 D | 1 mM VPA | 2.390810858 | 0.01473431 | | |
| 1 mM VPA | 12.9788342 | 307.161748 | 8 D | 1 mM VPA | 5.76411852 | 0.00135244 | Unknown | |
| 1 mM VPA | 4.76167568 | 308.158497 | 8 D | 1 mM VPA | 3.212062578 | 7.02E−05 | Unknown | |
| 1 mM VPA | 7.58973529 | 316.131974 | 4 D | 1 mM VPA | 1.861931503 | 0.01887819 | Unknown | |

TABLE 3-continued

Cellular metabolites measured in human embryonic stem cells treated with 1 mM of valproate

| EXP | RT | roundMASS | time | trt | Fold | Probt | annotation.1 | annotation.2 |
|---|---|---|---|---|---|---|---|---|
| 1 mM VPA | 66.9950694 | 316.200989 | 4 D | 1 mM VPA | 2.178145003 | 0.00392399 | Gibberellin A12 aldehyde | |
| 1 mM VPA | 62.665 | 319.244008 | 24 H | 1 mM VPA | 3.088914632 | 0.0457215 | Unknown | |
| 1 mM VPA | 19.019754 | 320.137541 | 4 D | 1 mM VPA | 2.083198045 | 0.04299189 | Unknown | |
| 1 mM VPA | 67.8541343 | 320.230187 | 4 D | 1 mM VPA | 1.784846494 | 0.03271491 | Unknown | |
| 1 mM VPA | 67.8541343 | 320.230187 | 24 H | 1 mM VPA | 1.981647012 | 0.01061379 | Unknown | |
| 1 mM VPA | 10.672 | 321.168775 | 24 H | 1 mM VPA | 2.153375627 | 0.00361195 | Unknown | |
| 1 mM VPA | 35.4656491 | 324.169472 | 4 D | 1 mM VPA | 2.684214566 | 0.00585101 | Unknown | |
| 1 mM VPA | 63.932859 | 326.0008 | 24 H | 1 mM VPA | 1.479797739 | 0.00340947 | Unknown | |
| 1 mM VPA | 63.932859 | 326.0008 | 4 D | 1 mM VPA | 1.541142217 | 0.01010729 | Unknown | |
| 1 mM VPA | 62.4897344 | 328.242558 | 4 D | 1 mM VPA | 1.831213495 | 0.03531113 | Docosahexaenoic acid | |
| 1 mM VPA | 55.092 | 329.001202 | 24 H | 1 mM VPA | 1.889887032 | 0.01315641 | Unknown | |
| 1 mM VPA | 6.02840404 | 330.105879 | 8 D | 1 mM VPA | 4.856779538 | 0.01414085 | Unknown | |
| 1 mM VPA | 12.8257065 | 330.153322 | 4 D | 1 mM VPA | −1.46094311 | 0.02278769 | Unknown | |
| 1 mM VPA | 47.63185 | 330.240548 | 4 D | 1 mM VPA | 2.777910272 | 0.01585359 | Unknown | |
| 1 mM VPA | 67.7267647 | 330.242694 | 4 D | 1 mM VPA | 3.168939244 | 0.02399703 | Unknown | |
| 1 mM VPA | 9.01253333 | 331.103633 | 8 D | 1 mM VPA | 5.010657754 | 0.00879812 | Unknown | |
| 1 mM VPA | 18.8430244 | 334.151446 | 24 H | 1 mM VPA | 7.598422851 | 0.04853637 | Unknown | |
| 1 mM VPA | 4.05694118 | 336.031706 | 4 D | 1 mM VPA | −23.1557728 | 5.36E−05 | Unknown | |
| 1 mM VPA | 6.7701658 | 336.15353 | 4 D | 1 mM VPA | 2.062222503 | 0.01789166 | Unknown | |
| 1 mM VPA | 54.915974 | 347.982073 | 4 D | 1 mM VPA | 16.74896451 | 0.02976287 | Unknown | |
| 1 mM VPA | 45.6079091 | 348.203076 | 4 D | 1 mM VPA | 3.375263185 | 0.00190076 | Unknown | |
| 1 mM VPA | 6.04629167 | 349.134979 | 8 D | 1 mM VPA | 1.449645356 | 0.02177991 | Unknown | |
| 1 mM VPA | 67.3780816 | 352.221576 | 24 H | 1 mM VPA | 2.329951622 | 0.01190993 | Prostaglandin | |
| 1 mM VPA | 22.8247245 | 353.157641 | 4 D | 1 mM VPA | 3.01822425 | 0.00974537 | 2-Keto-3-Methylvaleric acid | |
| 1 mM VPA | 19.103773 | 353.158931 | 4 D | 1 mM VPA | 2.134354771 | 0.00286811 | Unknown | |
| 1 mM VPA | 29.94892 | 355.242828 | 4 D | 1 mM VPA | 3.751584361 | 0.01212028 | Unknown | |
| 1 mM VPA | 15.1070313 | 356.156972 | 4 D | 1 mM VPA | 5.181249294 | 0.00024122 | l-Glutamic-gamma-semialdehyde | |
| 1 mM VPA | 59.1895507 | 358.229755 | 4 D | 1 mM VPA | 4.389936283 | 0.00450968 | Unknown | |
| 1 mM VPA | 7.78296 | 359.071286 | 8 D | 1 mM VPA | 3.504721971 | 0.02819084 | Unknown | |
| 1 mM VPA | 27.8286847 | 359.198793 | 4 D | 1 mM VPA | 2.67566964 | 0.04513681 | Unknown | |
| 1 mM VPA | 7.67294845 | 362.15214 | 24 H | 1 mM VPA | 3.677690313 | 0.01613594 | Aminohexanoic acid | |
| 1 mM VPA | 6.16412 | 364.18324 | 4 D | 1 mM VPA | 4.422922613 | 0.01590116 | Unknown | |
| 1 mM VPA | 19.3098372 | 364.185514 | 8 D | 1 mM VPA | 2.529233091 | 0.00135633 | Gibberellin A44 | |
| 1 mM VPA | 53.9854054 | 366.239292 | 4 D | 1 mM VPA | 6.176116644 | 3.03E−05 | 3b-Allotetrahydrocortisol | |
| 1 mM VPA | 17.7238836 | 372.188649 | 4 D | 1 mM VPA | 3.32395304 | 2.43E−07 | Ornithine | |
| 1 mM VPA | 11.4481111 | 374.168865 | 8 D | 1 mM VPA | 3.707636994 | 0.00715743 | Unknown | |
| 1 mM VPA | 13.8172619 | 374.207426 | 8 D | 1 mM VPA | 2.50185816 | 0.03397986 | Unknown | |
| 1 mM VPA | 17.6750468 | 388.183189 | 8 D | 1 mM VPA | 3.124878291 | 0.00060074 | Malic acid | Diglycolic acid |

TABLE 3-continued

Cellular metabolites measured in human embryonic stem cells treated with 1 mM of valproate

| EXP | RT | roundMASS | time | trt | Fold | Probt | annotation.1 | annotation.2 |
|---|---|---|---|---|---|---|---|---|
| 1 mM VPA | 21.3150329 | 392.209899 | 4 D | 1 mM VPA | 2.402938958 | 0.02146723 | Unknown | |
| 1 mM VPA | 79.7277263 | 404.258123 | 4 D | 1 mM VPA | 2.231633324 | 0.02122436 | 7a,12a-Dihydroxy-3-oxo-4-cholenoic acid | |
| 1 mM VPA | 24.7042427 | 407.206755 | 4 D | 1 mM VPA | 2.564362115 | 0.03457095 | Unknown | |
| 1 mM VPA | 16.9907536 | 408.172332 | 8 D | 1 mM VPA | 1.47549599 | 0.01779219 | 4-Hydroxyphenylacetaldehyde; | |
| 1 mM VPA | 16.9907536 | 408.172332 | 4 D | 1 mM VPA | 1.84894204 | 0.00218606 | 4-Hydroxyphenylacetaldehyde; | |
| 1 mM VPA | 29.02944 | 411.227331 | 4 D | 1 mM VPA | 3.412904392 | 0.00663705 | Gln His Lys | |
| 1 mM VPA | 31.0764706 | 411.788303 | 4 D | 1 mM VPA | 4.812211329 | 0.01959219 | Unknown | |
| 1 mM VPA | 9.74277941 | 412.191819 | 8 D | 1 mM VPA | 4.778970957 | 0.02280244 | Unknown | |
| 1 mM VPA | 24.0870602 | 416.213608 | 8 D | 1 mM VPA | 1.904483779 | 0.00013882 | Unknown | |
| 1 mM VPA | 13.7165 | 420.160178 | 4 D | 1 mM VPA | 4.500233939 | 0.04166145 | Unknown | |
| 1 mM VPA | 27.4410904 | 421.219685 | 4 D | 1 mM VPA | 2.92999865 | 0.01453378 | Unknown | |
| 1 mM VPA | 84.9993429 | 424.278966 | 4 D | 1 mM VPA | 2.302178983 | 0.02079967 | 1b,3a,7a,12a-Tetrahydroxy-5b-cholanoic acid | |
| 1 mM VPA | 84.9993429 | 424.278966 | 24 H | 1 mM VPA | 2.318995467 | 0.00016902 | 1b,3a,7a,12a-Tetrahydroxy-5b-cholanoic acid | |
| 1 mM VPA | 54.5975206 | 429.099036 | 4 D | 1 mM VPA | 3.524698852 | 2.05E−05 | Unknown | |
| 1 mM VPA | 25.5684706 | 430.183077 | 4 D | 1 mM VPA | 1.148698355 | 0.00012401 | Unknown | |
| 1 mM VPA | 47.39725 | 432.071275 | 4 D | 1 mM VPA | 2.645059178 | 0.01175067 | Unknown | |
| 1 mM VPA | 14.5288987 | 445.217914 | 8 D | 1 mM VPA | 2.820595921 | 0.00824753 | Unknown | |
| 1 mM VPA | 7.5585 | 445.286693 | 4 D | 1 mM VPA | −1.13705339 | 0.04453994 | Unknown | |
| 1 mM VPA | 19.9357624 | 455.226453 | 8 D | 1 mM VPA | 2.768491323 | 0.0146344 | Adipate | |
| 1 mM VPA | 84.7522195 | 470.350048 | 4 D | 1 mM VPA | 3.767741534 | 0.00027941 | Unknown | |
| 1 mM VPA | 8.479 | 471.146232 | 24 H | 1 mM VPA | 2.569343893 | 0.02598742 | 10-Formyldihydrofolate | |
| 1 mM VPA | 22.7650396 | 471.202698 | 4 D | 1 mM VPA | 2.257302866 | 1.30E−06 | Unknown | |
| 1 mM VPA | 15.4262845 | 491.253192 | 8 D | 1 mM VPA | 4.916392167 | 0.00321994 | Unknown | |
| 1 mM VPA | 60.5202059 | 493.458959 | 4 D | 1 mM VPA | 2.789487333 | 0.00131052 | Unknown | |
| 1 mM VPA | 44.8878444 | 502.216027 | 4 D | 1 mM VPA | 1.922921676 | 0.00968802 | Unknown | |
| 1 mM VPA | 14.5675854 | 502.227438 | 8 D | 1 mM VPA | 3.101787817 | 0.00862582 | Unknown | |
| 1 mM VPA | 31.0262667 | 504.2848 | 4 D | 1 mM VPA | 5.119489655 | 7.48E−05 | Unknown | |
| 1 mM VPA | 17.4495833 | 516.244788 | 4 D | 1 mM VPA | 2.722628233 | 0.00035163 | Unknown | |
| 1 mM VPA | 44.14925 | 527.321492 | 8 D | 1 mM VPA | 2.213454933 | 0.00740287 | Unknown | |
| 1 mM VPA | 70.8363171 | 528.362659 | 4 D | 1 mM VPA | 2.941801698 | 0.03554601 | Unknown | |
| 1 mM VPA | 74.25245 | 530.344375 | 24 H | 1 mM VPA | 3.680750602 | 0.03848341 | Unknown | |
| 1 mM VPA | 9.15167857 | 532.249475 | 8 D | 1 mM VPA | 7.170133597 | 0.00736475 | Unknown | |
| 1 mM VPA | 29.9863488 | 535.254098 | 8 D | 1 mM VPA | 6.049014001 | 0.00097203 | Unknown | |
| 1 mM VPA | 87.9394 | 535.392963 | 4 D | 1 mM VPA | 1.80125196 | 0.03183737 | Unknown | |
| 1 mM VPA | 8.02928261 | 549.20135 | 8 D | 1 mM VPA | 11.08087574 | 0.00035145 | Unknown | |
| 1 mM VPA | 19.5000458 | 550.228302 | 4 D | 1 mM VPA | 2.35969435 | 0.00064579 | Unknown | |
| 1 mM VPA | 24.7983934 | 551.248871 | 24 H | 1 mM VPA | 1.396388132 | 0.01890342 | Unknown | |
| 1 mM VPA | 74.3730889 | 552.326244 | 24 H | 1 mM VPA | 1.885569072 | 0.031072 | Lithocholate 3-O-glucuronide | |

TABLE 3-continued

Cellular metabolites measured in human embryonic stem cells treated with 1 mM of valproate

| EXP | RT | roundMASS | time | trt | Fold | Probt | annotation.1 | annotation.2 |
|---|---|---|---|---|---|---|---|---|
| 1 mM VPA | 75.3072222 | 561.322428 | 4 D | 1 mM VPA | 5.181249294 | 0.00798648 | Unknown | |
| 1 mM VPA | 14.1881491 | 565.230107 | 4 D | 1 mM VPA | 2.651300141 | 0.04312251 | Unknown | |
| 1 mM VPA | 5.97658065 | 574.262774 | 8 D | 1 mM VPA | 2.982867719 | 0.00682514 | Unknown | |
| 1 mM VPA | 70.4439429 | 594.37144 | 4 D | 1 mM VPA | 2.591881931 | 0.04970674 | 2-Hydroxyadenine | |
| 1 mM VPA | 15.895551 | 598.283549 | 8 D | 1 mM VPA | 4.074717385 | 0.00446383 | 2-Hydroxyadenine | |
| 1 mM VPA | 76.5242159 | 599.574322 | 8 D | 1 mM VPA | 2.569165805 | 2.63E−05 | Unknown | |
| 1 mM VPA | 76.2647 | 600.576755 | 4 D | 1 mM VPA | 1.998614186 | 0.00464652 | Unknown | |
| 1 mM VPA | 76.2647 | 600.576755 | 8 D | 1 mM VPA | 2.690920931 | 0.00059418 | Unknown | |
| 1 mM VPA | 79.7894576 | 613.589997 | 8 D | 1 mM VPA | 3.099853425 | 0.01314731 | Unknown | |
| 1 mM VPA | 8.59329167 | 658.254492 | 8 D | 1 mM VPA | 13.32441233 | 0.02367066 | Unknown | |
| 1 mM VPA | 60.8503 | 688.51026 | 4 D | 1 mM VPA | 3.690969971 | 0.00301918 | Unknown | |
| 1 mM VPA | 69.7080715 | 690.409258 | 4 D | 1 mM VPA | 3.89061979 | 0.001728 | Unknown | |
| 1 mM VPA | 65.32996 | 738.583348 | 4 D | 1 mM VPA | 3.877159268 | 0.00021681 | Unknown | |
| 1 mM VPA | 69.7792917 | 810.640892 | 4 D | 1 mM VPA | 3.934008296 | 0.00141534 | Unknown | |
| 1 mM VPA | 21.6729286 | 921.002586 | 24 H | 1 mM VPA | 10.91318268 | 0.00761215 | Unknown | |
| 1 mM VPA | 5.86856 | 1007.84992 | 4 D | 1 mM VPA | 23.49041018 | 0.04324009 | 3-Dehydrocarnitine | |

TABLE 4

Cellular metabolites produced in hESCs treated with 22 µM valproate

| cpdID | RT | MASSavg | time | _trt | Fold | P-value | Compound 1 | Compound2 |
|---|---|---|---|---|---|---|---|---|
| 77 | 28.21 | 99.0681 | 4 days | VPA | −1.81 | 0.020 | N-Methyl-2-pyrrolidinone | |
| 103 | 12.00 | 103.0991 | 4 days | VPA | −2.24 | 0.028 | Gamma-Aminobutryic acid | 2-Aminoisobutyric acid |
| 141 | 34.03 | 113.0840 | 4 days | VPA | −1.43 | 0.013 | Unknown | |
| 189 | 12.08 | 119.0473 | 8 days | VPA | 1.22 | 0.040 | 4-Amino-3-hydroxybutanoate | |
| 210 | 96.44 | 120.0436 | 4 days | VPA | −4.22 | 0.006 | 3,4-Dihydroxybutyric acid | |
| 263 | 19.93 | 129.0426 | 4 days | VPA | −1.27 | 0.021 | Pyroglutamic acid | 1-Pyrroline-4-hydroxy-2-carboxylate |
| 323 | 29.83 | 134.0939 | 4 days | VPA | −1.43 | 0.034 | Unknown | |
| 329 | 16.96 | 136.0384 | 24 hours | VPA | −2.09 | 0.038 | Hypoxanthine | Allopurinol |
| 343 | 12.98 | 141.0412 | 4 days | VPA | −1.24 | 0.011 | 1,4,4,6-Tetrahydro-6-oxonicotinate | 2-Aminomuconate semialdehyde |
| 362 | 11.40 | 141.9381 | 4 days | VPA | 1.19 | 0.034 | Unknown | |
| 396 | 11.97 | 146.0683 | 4 days | VPA | −1.02 | 0.002 | Glutamine | |
| 413 | 44.84 | 148.0638 | 8 days | VPA | −2.72 | 0.004 | Unknown | |
| 444 | 12.37 | 144.0687 | 8 days | VPA | −1.42 | 0.014 | Unknown | |
| 449 | 20.19 | 146.0066 | 8 days | VPA | −1.24 | 0.002 | 2,4-dicarboxylic acid | |
| 496 | 30.40 | 161.0688 | 8 days | VPA | −1.23 | 0.019 | 4-Methyl-L-glutamate | 2,2'-Iminodipropanoate |
| 431 | 24.83 | 164.4009 | 4 days | VPA | −1.17 | 0.049 | Unknown | |
| 603 | 72.83 | 173.9844 | 8 days | VPA | −1.80 | 0.017 | Unknown | |
| 604 | 20.34 | 174.0160 | 4 days | VPA | −1.36 | 0.003 | cis-Aconitate | Dehydroascorbate |
| 636 | 42.18 | 178.0994 | 8 days | VPA | 1.47 | 0.002 | Phenylvaleric acid | |
| 646 | 24.00 | 181.0740 | 4 days | VPA | −1.11 | 0.004 | Salsolinol | Homophenylalanine |
| 671 | 24.90 | 187.0609 | 4 days | VPA | −1.40 | 0.018 | Unknown | |
| 674 | 36.08 | 187.0973 | 4 days | VPA | 2.14 | 0.042 | Unknown | |
| 812 | 29.93 | 204.0899 | 8 days | VPA | 1.08 | 0.034 | L-Tryptophan | |
| 843 | 24.94 | 208.0840 | 4 days | VPA | −1.14 | 0.004 | Kynurenine | Formyl-4-hydroxykynurenamine |
| 893 | 44.64 | 214.1680 | 8 days | VPA | −2.11 | 0.005 | Fenamic acid | |
| 1089 | 47.40 | 242.0808 | 8 days | VPA | 1.87 | 0.02 | Unknown | |
| 1104 | 7.98 | 243.9760 | 4 days | VPA | 1.92 | 0.032 | Unknown | |
| 1282 | 44.30 | 274.0947 | 8 days | VPA | 1.78 | 0.019 | 3-Oxo-delta4-steroid | |
| 1447 | 43.40 | 300.2784 | 8 days | VPA | −2.22 | 0.033 | Unknown | |
| 1440 | 27.94 | 314.2032 | 4 day | VPA | −1.12 | 0.012 | Unknown | |
| 1637 | 24.91 | 330.1480 | 4 day | VPA | −1.42 | 0.004 | Unknown | |

TABLE 4-continued

Cellular metabolites produced in hESCs treated with 22 μM valproate

| cpdID | RT | MASSavg | time | _trt | Fold | P-value | Compound 1 | Compound2 |
|---|---|---|---|---|---|---|---|---|
| 1684 | 11.94 | 336.1634 | 4 days | VPA | −1.13 | 0.023 | Unknown | |
| 1691 | 34.87 | 338.0974 | 4 days | VPA | 1.74 | 0.033 | Unknown | |
| 1776 | 39.67 | 342.1130 | 4 day | VPA | 1.46 | 0.044 | Unknown | |
| 1816 | 24.40 | 348.1139 | 8 days | VPA | 2.56 | 0.025 | Unknown | |
| 1838 | 11.00 | 361.9194 | 4 days | VPA | −1.08 | 0.004 | Unknown | |
| 1948 | 12.00 | 384.1664 | 8 days | VPA | 1.38 | 0.018 | Unknown | |
| 1949 | 14.98 | 387.1498 | 4 days | VPA | −1.26 | 0.001 | Unknown | |
| 2084 | 64.24 | 414.2934 | 4 days | VPA | −1.20 | 0.031 | Unknown | |
| 2131 | 88.14 | 426.2983 | 4 days | VPA | 1.85 | 0.022 | Cholanoic acid | |
| 2134 | 74.20 | 427.1200 | 8 day | VPA | −1.88 | 0.044 | Unknown | |
| 2138 | 26.91 | 428.2423 | 8 day | VPA | 1.70 | 0.003 | Unknown | |
| 2144 | 34.14 | 431.2733 | 4 days | VPA | −1.24 | 0.041 | Unknown | |
| 2186 | 32.68 | 441.1394 | 8 days | VPA | −1.16 | 0.022 | Folate | Folic acid |
| 2191 | 64.67 | 442.2934 | 8 days | VPA | 1.79 | 0.001 | Unknown | |
| 2214 | 92.89 | 440.3448 | 8 days | VPA | −1.84 | 0.037 | Unknown | |
| 2233 | 12.00 | 444.0841 | 8 days | VPA | −1.30 | 0.041 | Unknown | |
| 2244 | 64.41 | 449.3198 | 24 hours | VPA | −1.78 | 0.024 | Unknown | |
| 2291 | 87.74 | 470.3249 | 4 days | VPA | −0.18 | 0.002 | Unknown | |
| 2244 | 30.91 | 467.2631 | 8 days | VPA | 1.69 | 0.004 | Unknown | |
| 743 | 13.81 | 197.0186 | 8 day | VPA | −1.39 | 0.016 | Unknown | |
| 636 | 42.18 | 178.0994 | 8 days | | 1.47 | 0.010 | Unknown | |

TABLE 6

Cellular metabolites measured in neural precursors derived from hESells treated with 1 mM of valproate

| EXP | RT | roundMASS | time | trt | Fold | annotation.1 | annotation.2 |
|---|---|---|---|---|---|---|---|
| NS 1 mM VPA | 36.648 | 102.0322438 | 2 d | NS 1 mM VPA | −2.23119 | 2-Ketobutyric acid | Acetoacetic acid |
| NS 1 mM VPA | 36.648 | 102.0322438 | 4 d | NS 1 mM VPA | −1.83846 | 2-Ketobutyric acid | Acetoacetic acid |
| NS 1 mM VPA | 9.33225 | 119.958645 | 4 d | NS 1 mM VPA | 6.98086 | Unknown | |
| NS 1 mM VPA | 12.2841 | 121.0621387 | 4 d | NS 1 mM VPA | 3.502341 | Unknown | |
| NS 1 mM VPA | 24.10558 | 125.0838833 | 2 d | NS 1 mM VPA | 1.79316 | Unknown | |
| NS 1 mM VPA | 30.43985 | 125.08394 | 2 d | NS 1 mM VPA | 1.529012 | 1-Methylhistamine | |
| NS 1 mM VPA | 30.43985 | 125.08394 | 4 d | NS 1 mM VPA | 1.576622 | 1-Methylhistamine | |
| NS 1 mM VPA | 23.33772 | 129.0573222 | 2 d | NS 1 mM VPA | 1.543375 | Pyroglutamic acid | |
| NS 1 mM VPA | 23.33772 | 129.0573222 | 4 d | NS 1 mM VPA | 1.663008 | Pyroglutamic acid | |
| NS 1 mM VPA | 12.13216 | 131.0941359 | 4 d | NS 1 mM VPA | 1.577796 | L-Isoleucine | Aminocaproic acid |
| NS 1 mM VPA | 12.13216 | 131.0941359 | 2 d | NS 1 mM VPA | 2.474877 | L-Isoleucine | Aminocaproic acid |
| NS 1 mM VPA | 8.881211 | 136.0366263 | 2 d | NS 1 mM VPA | 2.287439 | Erythronic acid | Erythronic acid |
| NS 1 mM VPA | 8.881211 | 136.0366263 | 4 d | NS 1 mM VPA | 2.653537 | Erythronic acid | Erythronic acid |
| NS 1 mM VPA | 12.00967 | 136.0376917 | 2 d | NS 1 mM VPA | 2.346054 | Erythronic acid | Erythronic acid |
| NS 1 mM VPA | 12.00967 | 136.0376917 | 4 d | NS 1 mM VPA | 2.914393 | Erythronic acid | Erythronic acid |
| NS 1 mM VPA | 3.9669 | 138.04396 | 2 d | NS 1 mM VPA | 1.521407 | Urocanic acid | Nicotinamide N-oxide |
| NS 1 mM VPA | 3.9669 | 138.04396 | 4 d | NS 1 mM VPA | 2.642558 | Urocanic acid | Nicotinamide N-oxide |
| NS 1 mM VPA | 4.28225 | 141.9392625 | 2 d | NS 1 mM VPA | 1.077336 | 5,10-Methylenetetrahydrofolate | |
| NS 1 mM VPA | 4.28225 | 141.9392625 | 4 d | NS 1 mM VPA | 1.111532 | 5,10-Methylenetetrahydrofolate | |
| NS 1 mM VPA | 23.33784 | 143.0734947 | 2 d | NS 1 mM VPA | 1.728349 | Unknown | |
| NS 1 mM VPA | 23.33784 | 143.0734947 | 4 d | NS 1 mM VPA | 1.986515 | Unknown | |
| NS 1 mM VPA | 55.5845 | 144.1153313 | 4 d | NS 1 mM VPA | 10.83178 | Caprylic acid | Valproic acid |

TABLE 6-continued

Cellular metabolites measured in neural precursors derived from hESells treated with 1 mM of valproate

| EXP | RT | roundMASS | time | trt | Fold | annotation.1 | annotation.2 |
|---|---|---|---|---|---|---|---|
| NS 1 mM VPA | 55.5845 | 144.1153313 | 2 d | NS 1 mM VPA | 11.64535 | Caprylic acid | Valproic acid |
| NS 1 mM VPA | 5.609182 | 145.1572818 | 2 d | NS 1 mM VPA | 1.00993 | Spermidine | |
| NS 1 mM VPA | 5.609182 | 145.1572818 | 4 d | NS 1 mM VPA | 1.117314 | Spermidine | |
| NS 1 mM VPA | 33.6357 | 148.03738 | 4 d | NS 1 mM VPA | −5.75294 | Citramalic acid | Hydroxyglutaric acid |
| NS 1 mM VPA | 33.6357 | 148.03738 | 2 d | NS 1 mM VPA | −1.49356 | Citramalic acid | Hydroxyglutaric acid |
| NS 1 mM VPA | 62.42614 | 152.1201762 | 4 d | NS 1 mM VPA | 2.50602 | Unknown | |
| NS 1 mM VPA | 62.42614 | 152.1201762 | 2 d | NS 1 mM VPA | 3.371426 | Unknown | |
| NS 1 mM VPA | 8.862333 | 158.0177333 | 2 d | NS 1 mM VPA | 1.596402 | Unknown | |
| NS 1 mM VPA | 8.862333 | 158.0177333 | 4 d | NS 1 mM VPA | 2.236076 | Unknown | |
| NS 1 mM VPA | 8.269857 | 158.1374571 | 4 d | NS 1 mM VPA | 3.106829 | Unknown | |
| NS 1 mM VPA | 8.269857 | 158.1374571 | 2 d | NS 1 mM VPA | 3.626498 | Unknown | |
| NS 1 mM VPA | 10.07033 | 159.0688667 | 2 d | NS 1 mM VPA | −2.87026 | Indoleacetaldehyde | |
| NS 1 mM VPA | 10.07033 | 159.0688667 | 4 d | NS 1 mM VPA | −1.35298 | Indoleacetaldehyde | |
| NS 1 mM VPA | 12.85888 | 161.0509118 | 2 d | NS 1 mM VPA | 2.601443 | Unknown | |
| NS 1 mM VPA | 12.85888 | 161.0509118 | 4 d | NS 1 mM VPA | 5.136057 | Unknown | |
| NS 1 mM VPA | 6.713565 | 166.0840609 | 4 d | NS 1 mM VPA | 33.80296 | Unknown | |
| NS 1 mM VPA | 6.713565 | 166.0840609 | 2 d | NS 1 mM VPA | 90.97629 | Unknown | |
| NS 1 mM VPA | 23.58909 | 168.0687909 | 2 d | NS 1 mM VPA | 4.649885 | Unknown | |
| NS 1 mM VPA | 23.58909 | 168.0687909 | 4 d | NS 1 mM VPA | 5.02165 | Unknown | |
| NS 1 mM VPA | 31.08471 | 171.1250706 | 4 d | NS 1 mM VPA | 1.626943 | Unknown | |
| NS 1 mM VPA | 62.57554 | 172.1454 | 4 d | NS 1 mM VPA | 1.745543 | Capric acid | Decanoic acid |
| NS 1 mM VPA | 62.57554 | 172.1454 | 2 d | NS 1 mM VPA | 1.8794 | Caprica cid | Decanoic acid |
| NS 1 mM VPA | 20.68721 | 175.0830857 | 2 d | NS 1 mM VPA | 1.153935 | N-Carboxyethyl-gamma-aminobutyric acid | |
| NS 1 mM VPA | 20.68721 | 175.0830857 | 4 d | NS 1 mM VPA | 2.294392 | N-Carboxyethyl-gamma-aminobutyric acid | |
| NS 1 mM VPA | 41.71109 | 176.0946 | 2 d | NS 1 mM VPA | −1.60014 | Serotonin | |
| NS 1 mM VPA | 41.71109 | 176.0946 | 4 d | NS 1 mM VPA | −1.23797 | Serotonin | |
| NS 1 mM VPA | 25.29 | 177.0469231 | 2 d | NS 1 mM VPA | 3.379693 | N-Formyl-L-methionine | |
| NS 1 mM VPA | 25.29 | 177.0469231 | 4 d | NS 1 mM VPA | 3.82485 | N-Formyl-L-methionine | |
| NS 1 mM VPA | 26.75621 | 177.0789684 | 2 d | NS 1 mM VPA | 1.26513 | 5-Hydroxytryptophol | |
| NS 1 mM VPA | 26.75621 | 177.0789684 | 4 d | NS 1 mM VPA | 1.423219 | 5-Hydroxytryptophol | |
| NS 1 mM VPA | 8.503333 | 177.113375 | 2 d | NS 1 mM VPA | −6.74695 | Unknown | |
| NS 1 mM VPA | 8.503333 | 177.113375 | 4 d | NS 1 mM VPA | −2.88736 | Unknown | |
| NS 1 mM VPA | 27.53982 | 179.0938118 | 2 d | NS 1 mM VPA | −2.71897 | Salsolinol | Homophenylalanine |
| NS 1 mM VPA | 27.53982 | 179.0938118 | 4 d | NS 1 mM VPA | −1.71231 | Salsolinol | Homophenylalanine |
| NS 1 mM VPA | 55.15089 | 179.0949632 | 4 d | NS 1 mM VPA | −1.64525 | Salsolinol | Homophenylalanine |
| NS 1 mM VPA | 55.15089 | 179.0949632 | 2 d | NS 1 mM VPA | −1.39458 | Salsolinol | Homophenylalanine |
| NS 1 mM VPA | 37.08443 | 185.1406571 | 4 d | NS 1 mM VPA | −2.39254 | Unknown | |
| NS 1 mM VPA | 23.33726 | 187.0635211 | 2 d | NS 1 mM VPA | 1.674013 | Unknown | |

TABLE 6-continued

Cellular metabolites measured in neural precursors derived from hESells treated with 1 mM of valproate

| EXP | RT | roundMASS | time | trt | Fold | annotation.1 | annotation.2 |
|---|---|---|---|---|---|---|---|
| NS 1 mM VPA | 23.33726 | 187.0635211 | 4 d | NS 1 mM VPA | 1.921765 | Unknown | |
| NS 1 mM VPA | 28.77111 | 187.1206333 | 2 d | NS 1 mM VPA | 2.457813 | 8-Amino-7-oxononanoic acid | |
| NS 1 mM VPA | 28.77111 | 187.1206333 | 4 d | NS 1 mM VPA | 3.559361 | 8-Amino-7-oxononanoic acid | |
| NS 1 mM VPA | 62.50765 | 190.1720118 | 4 d | NS 1 mM VPA | 1.758553 | Unknown | |
| NS 1 mM VPA | 62.50765 | 190.1720118 | 2 d | NS 1 mM VPA | 1.940004 | Unknown | |
| NS 1 mM VPA | 7.850167 | 196.0933333 | 4 d | NS 1 mM VPA | 1.937281 | Unknown | |
| NS 1 mM VPA | 7.850167 | 196.0933333 | 2 d | NS 1 mM VPA | 6.390957 | Unknown | |
| NS 1 mM VPA | 45.36418 | 197.1060727 | 2 d | NS 1 mM VPA | 1.280472 | L-Metanephrine | |
| NS 1 mM VPA | 45.36418 | 197.1060727 | 4 d | NS 1 mM VPA | 1.62879 | L-Metanephrine | |
| NS 1 mM VPA | 8.363925 | 199.0952975 | 2 d | NS 1 mM VPA | 10.44025 | Unknown | |
| NS 1 mM VPA | 8.363925 | 199.0952975 | 4 d | NS 1 mM VPA | 10.88407 | Unknown | |
| NS 1 mM VPA | 22.22829 | 206.06375 | 4 d | NS 1 mM VPA | 2.263839 | Unknown | |
| NS 1 mM VPA | 22.22829 | 206.06375 | 2 d | NS 1 mM VPA | 4.317383 | Unknown | |
| NS 1 mM VPA | 62.46678 | 208.1829217 | 4 d | NS 1 mM VPA | 2.052914 | Unknown | |
| NS 1 mM VPA | 62.46678 | 208.1829217 | 2 d | NS 1 mM VPA | 2.734885 | Unknown | |
| NS 1 mM VPA | 9.2636 | 211.0349075 | 4 d | NS 1 mM VPA | 1.516795 | Creatine phosphate | |
| NS 1 mM VPA | 9.2636 | 211.0349075 | 2 d | NS 1 mM VPA | 1.893074 | Creatine phosphate | |
| NS 1 mM VPA | 44.11333 | 212.1400167 | 4 d | NS 1 mM VPA | −9.35257 | Unknown | |
| NS 1 mM VPA | 44.11333 | 212.1400167 | 2 d | NS 1 mM VPA | −6.85493 | Unknown | |
| NS 1 mM VPA | 7.746115 | 217.1048885 | 2 d | NS 1 mM VPA | 2.916422 | N-a-Acetylcitrulline | |
| NS 1 mM VPA | 7.746115 | 217.1048885 | 4 d | NS 1 mM VPA | 23.86569 | N-a-Acetylcitrulline | |
| NS 1 mM VPA | 22.26729 | 217.1307097 | 2 d | NS 1 mM VPA | 2.122093 | Propionylcarnitine | |
| NS 1 mM VPA | 22.26729 | 217.1307097 | 4 d | NS 1 mM VPA | 2.236406 | Propionylcarnitine | |
| NS 1 mM VPA | 16.1278 | 220.0841 | 2 d | NS 1 mM VPA | −1.25214 | 5-Hydroxytryptophan | 5-Hydroxy-L-tryptophan |
| NS 1 mM VPA | 16.1278 | 220.0841 | 4 d | NS 1 mM VPA | 1.215413 | 5-Hydroxytryptophan | 5-Hydroxy-L-tryptophan |
| NS 1 mM VPA | 9.809786 | 220.0845 | 2 d | NS 1 mM VPA | −1.06102 | 5-Hydroxytryptophan | 5-Hydroxy-L-tryptophan |
| NS 1 mM VPA | 9.809786 | 220.0845 | 4 d | NS 1 mM VPA | 1.371126 | 5-Hydroxytryptophan | 5-Hydroxy-L-tryptophan |
| NS 1 mM VPA | 12.15958 | 220.0845895 | 2 d | NS 1 mM VPA | −1.54275 | 5-Hydroxytryptophan | 5-Hydroxy-L-tryptophan |
| NS 1 mM VPA | 12.15958 | 220.0845895 | 4 d | NS 1 mM VPA | 1.162644 | 5-Hydroxytryptophan | 5-Hydroxy-L-tryptophan |
| NS 1 mM VPA | 8.4172 | 223.92951 | 2 d | NS 1 mM VPA | −3.24844 | Unknown | |
| NS 1 mM VPA | 8.4172 | 223.92951 | 4 d | NS 1 mM VPA | −2.85631 | Unknown | |
| NS 1 mM VPA | 22.009 | 225.62685 | 4 d | NS 1 mM VPA | 2.716119 | Unknown | |
| NS 1 mM VPA | 22.009 | 225.62685 | 2 d | NS 1 mM VPA | 3.854852 | Unknown | |
| NS 1 mM VPA | 10.0963 | 227.01938 | 4 d | NS 1 mM VPA | 1.631698 | L-Glutamic acid 5-phosphate | |
| NS 1 mM VPA | 6.0771 | 227.09052 | 4 d | NS 1 mM VPA | −5.41292 | Deoxycytidine | |
| NS 1 mM VPA | 6.0771 | 227.09052 | 2 d | NS 1 mM VPA | −2.98012 | Deoxycytidine | |
| NS 1 mM VPA | 14.51476 | 228.05894 | 4 d | NS 1 mM VPA | 3.339111 | Unknown | |
| NS 1 mM VPA | 14.51476 | 228.05894 | 2 d | NS 1 mM VPA | 6.425869 | Unknown | |

TABLE 6-continued

Cellular metabolites measured in neural precursors derived from hESells treated with 1 mM of valproate

| EXP | RT | roundMASS | time | trt | Fold | annotation.1 | annotation.2 |
|---|---|---|---|---|---|---|---|
| NS 1 mM VPA | 67.13919 | 230.1515667 | 4 d | NS 1 mM VPA | −5.02528 | Dodecanedioic acid | |
| NS 1 mM VPA | 67.13919 | 230.1515667 | 2 d | NS 1 mM VPA | −2.98776 | Dodecanedioic acid | |
| NS 1 mM VPA | 19.28286 | 234.1010143 | 2 d | NS 1 mM VPA | −1.25569 | 5-Methoxytryptophan | |
| NS 1 mM VPA | 19.28286 | 234.1010143 | 4 d | NS 1 mM VPA | −1.18869 | 5-Methoxytryptophan | |
| NS 1 mM VPA | 10.51438 | 236.0815625 | 4 d | NS 1 mM VPA | 1.367658 | N'-Formylkynurenine | |
| NS 1 mM VPA | 17.826 | 238.0864167 | 2 d | NS 1 mM VPA | 5.397657 | Propanoic acid | |
| NS 1 mM VPA | 17.826 | 238.0864167 | 4 d | NS 1 mM VPA | 5.703771 | Propanoic acid | |
| NS 1 mM VPA | 7.8115 | 239.087425 | 4 d | NS 1 mM VPA | 1.950568 | Unknown | |
| NS 1 mM VPA | 7.8115 | 239.087425 | 2 d | NS 1 mM VPA | 30.57925 | Unknown | |
| NS 1 mM VPA | 42.05716 | 246.1469838 | 4 d | NS 1 mM VPA | −2.28801 | 3-Hydroxydodecanedioic acid | |
| NS 1 mM VPA | 42.05716 | 246.1469838 | 2 d | NS 1 mM VPA | −1.71537 | 3-Hydroxydodecanedioic acid | |
| NS 1 mM VPA | 30.669 | 256.09664 | 4 d | NS 1 mM VPA | 1.692487 | Aryl beta-D-glucoside | |
| NS 1 mM VPA | 30.669 | 256.09664 | 2 d | NS 1 mM VPA | 1.966122 | Aryl beta-D-glucoside | |
| NS 1 mM VPA | 59.82681 | 256.1080938 | 2 d | NS 1 mM VPA | 2.962348 | Unknown | |
| NS 1 mM VPA | 59.82681 | 256.1080938 | 4 d | NS 1 mM VPA | 3.845884 | Unknown | |
| NS 1 mM VPA | 69.57173 | 258.18226 | 4 d | NS 1 mM VPA | 4.075358 | Tetradecanedioic acid | |
| NS 1 mM VPA | 69.57173 | 258.18226 | 2 d | NS 1 mM VPA | 5.744182 | Tetradecanedioic acid | |
| NS 1 mM VPA | 22.0274 | 264.11209 | 2 d | NS 1 mM VPA | 1.230997 | Acetyl-N-formyl-5-methoxykynurenamine | |
| NS 1 mM VPA | 22.0274 | 264.11209 | 4 d | NS 1 mM VPA | 1.338241 | Acetyl-N-formyl-5-methoxykynurenamine | |
| NS 1 mM VPA | 11.94583 | 268.0806 | 4 d | NS 1 mM VPA | 3.240011 | 3-Deoxy-D-glycero-D-galacto-2-nonulosonic acid | |
| NS 1 mM VPA | 11.94583 | 268.0806 | 2 d | NS 1 mM VPA | 3.329815 | 3-Deoxy-D-glycero-D-galacto-2-nonulosonic acid | |
| NS 1 mM VPA | 20.58271 | 270.1203286 | 2 d | NS 1 mM VPA | 1.808333 | L-gamma-Glutamyl-L-hypoglycin; | |
| NS 1 mM VPA | 20.58271 | 270.1203286 | 4 d | NS 1 mM VPA | 1.890677 | L-gamma-Glutamyl-L-hypoglycin; | |
| NS 1 mM VPA | 56.5351 | 272.08566 | 4 d | NS 1 mM VPA | 1.178071 | 5-S-Cysteinyldopamine | |
| NS 1 mM VPA | 56.5351 | 272.08566 | 2 d | NS 1 mM VPA | 1.718998 | 5-S-Cysteinyldopamine | |
| NS 1 mM VPA | 64.11407 | 278.0251024 | 4 d | NS 1 mM VPA | 5.17024 | Unknown | |
| NS 1 mM VPA | 64.11407 | 278.0251024 | 2 d | NS 1 mM VPA | 6.667641 | Unknown | |
| NS 1 mM VPA | 28.90879 | 290.1501643 | 4 d | NS 1 mM VPA | 3.329013 | Unknown | |
| NS 1 mM VPA | 28.90879 | 290.1501643 | 2 d | NS 1 mM VPA | 8.490919 | Unknown | |
| NS 1 mM VPA | 26.42889 | 295.1063913 | 2 d | NS 1 mM VPA | 7.265582 | Unknown | |
| NS 1 mM VPA | 26.42889 | 295.1063913 | 4 d | NS 1 mM VPA | 8.896581 | Unknown | |
| NS 1 mM VPA | 73.28533 | 315.2406111 | 4 d | NS 1 mM VPA | 2.599877 | Decanoylcarnitine | |
| NS 1 mM VPA | 73.28533 | 315.2406111 | 2 d | NS 1 mM VPA | 3.899691 | Decanoylcarnitine | |
| NS 1 mM VPA | 77.38144 | 318.2193688 | 4 d | NS 1 mM VPA | 1.932263 | Leukotriene A4 | |
| NS 1 mM VPA | 77.38144 | 318.2193688 | 2 d | NS 1 mM VPA | 2.342543 | Leukotriene A4 | |
| NS 1 mM VPA | 41.33024 | 324.1144588 | 4 d | NS 1 mM VPA | 3.317923 | Acetohexamide | |
| NS 1 mM VPA | 41.33024 | 324.1144588 | 2 d | NS 1 mM VPA | 3.713445 | Acetohexamide | |
| NS 1 mM VPA | 33.60576 | 330.1013765 | 4 d | NS 1 mM VPA | 2.25561 | Unknown | |

TABLE 6-continued

Cellular metabolites measured in neural precursors derived from hESells treated with 1 mM of valproate

| EXP | RT | roundMASS | time | trt | Fold | annotation.1 | annotation.2 |
|---|---|---|---|---|---|---|---|
| NS 1 mM VPA | 33.60576 | 330.1013765 | 2 d | NS 1 mM VPA | 2.310447 | Unknown | |
| NS 1 mM VPA | 35.06233 | 331.1049867 | 4 d | NS 1 mM VPA | 2.719086 | Unknown | |
| NS 1 mM VPA | 35.06233 | 331.1049867 | 2 d | NS 1 mM VPA | 3.041317 | Unknown | |
| NS 1 mM VPA | 52.557 | 349.22592 | 4 d | NS 1 mM VPA | 2.41993 | Unknown | |
| NS 1 mM VPA | 52.557 | 349.22592 | 2 d | NS 1 mM VPA | 6.652089 | Unknown | |
| NS 1 mM VPA | 53.57858 | 350.2096 | 4 d | NS 1 mM VPA | 1.508076 | Prostaglandin E3 | |
| NS 1 mM VPA | 53.57858 | 350.2096 | 2 d | NS 1 mM VPA | 1.612834 | Prostaglandin E3 | |
| NS 1 mM VPA | 65.76353 | 356.2702895 | 4 d | NS 1 mM VPA | 2.05875 | Tetracosahexaenoic acid | |
| NS 1 mM VPA | 65.76353 | 356.2702895 | 2 d | NS 1 mM VPA | 2.405825 | Tetracosahexaenoic acid | |
| NS 1 mM VPA | 81.79271 | 369.2880824 | 4 d | NS 1 mM VPA | 6.636435 | cis-5-Tetradecenoylcarnitine | |
| NS 1 mM VPA | 81.79271 | 369.2880824 | 2 d | NS 1 mM VPA | 9.965816 | cis-5-Tetradecenoylcarnitine | |
| NS 1 mM VPA | 27.34076 | 374.1222235 | 4 d | NS 1 mM VPA | 2.300022 | Unknown | |
| NS 1 mM VPA | 27.34076 | 374.1222235 | 2 d | NS 1 mM VPA | 2.889783 | Unknown | |
| NS 1 mM VPA | 8.881 | 380.164 | 4 d | NS 1 mM VPA | 2.519949 | Unknown | |
| NS 1 mM VPA | 8.881 | 380.164 | 2 d | NS 1 mM VPA | 2.633667 | Unknown | |
| NS 1 mM VPA | 22.46583 | 385.1025667 | 4 d | NS 1 mM VPA | 1.45497 | S-Inosyl-L-homocysteine | |
| NS 1 mM VPA | 22.46583 | 385.1025667 | 2 d | NS 1 mM VPA | 1.533705 | S-Inosyl-L-homocysteine | |
| NS 1 mM VPA | 68.31689 | 386.23145 | 4 d | NS 1 mM VPA | 6.386163 | 1-tridecanoyl-sn-glycero-3-phosphate | |
| NS 1 mM VPA | 68.31689 | 386.23145 | 2 d | NS 1 mM VPA | 7.117538 | 1-tridecanoyl-sn-glycero-3-phosphate | |
| NS 1 mM VPA | 89.1946 | 390.27608 | 2 d | NS 1 mM VPA | 1.682855 | 7-Hydroxy-3-oxocholanoic acid | |
| NS 1 mM VPA | 89.1946 | 390.27608 | 4 d | NS 1 mM VPA | 3.296512 | 7-Hydroxy-3-oxocholanoic acid | |
| NS 1 mM VPA | 26.42904 | 394.2127308 | 2 d | NS 1 mM VPA | 2.670186 | Unknown | |
| NS 1 mM VPA | 26.42904 | 394.2127308 | 4 d | NS 1 mM VPA | 3.50273 | unknown | |
| NS 1 mM VPA | 76.06971 | 398.2439857 | 4 d | NS 1 mM VPA | 2.845315 | Unknown | |
| NS 1 mM VPA | 76.06971 | 398.2439857 | 2 d | NS 1 mM VPA | 3.609136 | Unknown | |
| NS 1 mM VPA | 33.53038 | 399.2100125 | 2 d | NS 1 mM VPA | 6.345173 | unknown | |
| NS 1 mM VPA | 33.53038 | 399.2100125 | 4 d | NS 1 mM VPA | 8.777833 | unknown | |
| NS 1 mM VPA | 8.9305 | 406.1058875 | 4 d | NS 1 mM VPA | 1.976577 | unknown | |
| NS 1 mM VPA | 8.9305 | 406.1058875 | 2 d | NS 1 mM VPA | 2.00634 | unknown | |
| NS 1 mM VPA | 65.76447 | 409.3155632 | 4 d | NS 1 mM VPA | 4.662331 | Unknown | |
| NS 1 mM VPA | 65.76447 | 409.3155632 | 2 d | NS 1 mM VPA | 5.930421 | Unknown | |
| NS 1 mM VPA | 18.93053 | 416.0834333 | 4 d | NS 1 mM VPA | 3.527468 | Unknown | |
| NS 1 mM VPA | 18.93053 | 416.0834333 | 2 d | NS 1 mM VPA | 4.202864 | Unknown | |
| NS 1 mM VPA | 8.6127 | 416.20208 | 2 d | NS 1 mM VPA | 3.29783 | Lactone | |
| NS 1 mM VPA | 8.6127 | 416.20208 | 4 d | NS 1 mM VPA | 3.495266 | Lactone | |
| NS 1 mM VPA | 14.963 | 420.05275 | 2 d | NS 1 mM VPA | −3.434 | Unknown | |
| NS 1 mM VPA | 14.963 | 420.05275 | 4 d | NS 1 mM VPA | −3.09195 | Unknown | |
| NS 1 mM VPA | 62.93221 | 427.1025357 | 2 d | NS 1 mM VPA | 3.882014 | Unknown | |

TABLE 6-continued

Cellular metabolites measured in neural precursors derived from hESells treated with 1 mM of valproate

| EXP | RT | roundMASS | time | trt | Fold | annotation.1 | annotation.2 |
|---|---|---|---|---|---|---|---|
| NS 1 mM VPA | 62.93221 | 427.1025357 | 4 d | NS 1 mM VPA | 6.045912 | Unknown | |
| NS 1 mM VPA | 33.59771 | 430.1185143 | 2 d | NS 1 mM VPA | 3.469797 | N-Ethylmaleimide-S-glutathione | |
| NS 1 mM VPA | 33.59771 | 430.1185143 | 4 d | NS 1 mM VPA | 3.98295 | N-Ethylmaleimide-S-glutathione | |
| NS 1 mM VPA | 24.9718 | 434.19845 | 4 d | NS 1 mM VPA | 3.713915 | Unknown | |
| NS 1 mM VPA | 24.9718 | 434.19845 | 2 d | NS 1 mM VPA | 3.76882 | Unknown | |
| NS 1 mM VPA | 23.07 | 434.1985875 | 2 d | NS 1 mM VPA | 2.416021 | Unknown | |
| NS 1 mM VPA | 23.07 | 434.1985875 | 4 d | NS 1 mM VPA | 3.44524 | Unknown | |
| NS 1 mM VPA | 37.33089 | 438.1460579 | 2 d | NS 1 mM VPA | 2.829002 | Unknown | |
| NS 1 mM VPA | 37.33089 | 438.1460579 | 4 d | NS 1 mM VPA | 3.253909 | Unknown | |
| NS 1 mM VPA | 5.410909 | 441.9424 | 4 d | NS 1 mM VPA | −3.5345 | Unknown | |
| NS 1 mM VPA | 5.410909 | 441.9424 | 2 d | NS 1 mM VPA | −2.45689 | Unknown | |
| NS 1 mM VPA | 34.58505 | 443.2362947 | 2 d | NS 1 mM VPA | 2.648862 | Unknown | |
| NS 1 mM VPA | 34.58505 | 443.2362947 | 4 d | NS 1 mM VPA | 3.427563 | Unknown | |
| NS 1 mM VPA | 33.85267 | 445.1694 | 2 d | NS 1 mM VPA | −1.31487 | Tetrahydrofolic acid | Tetrahydrofolate |
| NS 1 mM VPA | 33.85267 | 445.1694 | 4 d | NS 1 mM VPA | −1.04073 | Tetrahydrofolic acid | Tetrahydrofolate |
| NS 1 mM VPA | 38.63717 | 449.1638333 | 2 d | NS 1 mM VPA | 3.04704 | Unknown | |
| NS 1 mM VPA | 38.63717 | 449.1638333 | 4 d | NS 1 mM VPA | 4.206864 | Unknown | |
| NS 1 mM VPA | 21.9772 | 456.2448 | 4 d | NS 1 mM VPA | 4.145738 | unknown | |
| NS 1 mM VPA | 21.9772 | 456.2448 | 2 d | NS 1 mM VPA | 8.390862 | unknown | |
| NS 1 mM VPA | 42.40369 | 467.1731077 | 2 d | NS 1 mM VPA | −10.3323 | Unknown | |
| NS 1 mM VPA | 42.40369 | 467.1731077 | 4 d | NS 1 mM VPA | −4.42263 | Unknown | |
| NS 1 mM VPA | 23.41189 | 474.1090778 | 4 d | NS 1 mM VPA | 2.094815 | Unknown | |
| NS 1 mM VPA | 23.41189 | 474.1090778 | 2 d | NS 1 mM VPA | 2.928466 | Unknown | |
| NS 1 mM VPA | 22.666 | 482.1554563 | 4 d | NS 1 mM VPA | 2.075721 | Unknown | |
| NS 1 mM VPA | 22.666 | 482.1554563 | 2 d | NS 1 mM VPA | 2.519832 | Unknown | |
| NS 1 mM VPA | 75.55014 | 493.3252405 | 4 d | NS 1 mM VPA | 2.09415 | 1-(9E-hexadecenoyl)-sn-glycero-3-phosphocholine | |
| NS 1 mM VPA | 75.55014 | 493.3252405 | 2 d | NS 1 mM VPA | 2.34894 | 1-(9E-hexadecenoyl)-sn-glycero-3- | phosphocholine |
| NS 1 mM VPA | 37.34533 | 506.1856556 | 2 d | NS 1 mM VPA | 2.031088 | Unknown | |
| NS 1 mM VPA | 37.34533 | 506.1856556 | 4 d | NS 1 mM VPA | 2.405509 | unknown | |
| NS 1 mM VPA | 23.67792 | 514.162208 | 2 d | NS 1 mM VPA | 2.2744 | unknown | |
| NS 1 mM VPA | 23.67792 | 514.162208 | 4 d | NS 1 mM VPA | 3.27837 | unknown | |
| NS 1 mM VPA | 36.44195 | 514.2430667 | 4 d | NS 1 mM VPA | 4.332807 | Unknown | |
| NS 1 mM VPA | 36.44195 | 514.2430667 | 2 d | NS 1 mM VPA | 4.565629 | Unknown | |
| NS 1 mM VPA | 41.29621 | 527.3552786 | 2 d | NS 1 mM VPA | 9.44893 | Unknown | |
| NS 1 mM VPA | 41.29621 | 527.3552786 | 4 d | NS 1 mM VPA | 12.3251 | Unknown | |
| NS 1 mM VPA | 21.94381 | 534.2784846 | 4 d | NS 1 mM VPA | 2.818876 | unknown | |
| NS 1 mM VPA | 21.94381 | 534.2784846 | 2 d | NS 1 mM VPA | 2.912693 | unknown | |
| NS 1 mM VPA | 26.05061 | 546.3146929 | 2 d | NS 1 mM VPA | 1.574871 | Unknown | |

TABLE 6-continued

Cellular metabolites measured in neural precursors derived from hESells treated with 1 mM of valproate

| EXP | RT | roundMASS | time | trt | Fold | annotation.1 | annotation.2 |
|---|---|---|---|---|---|---|---|
| NS 1 mM VPA | 26.05061 | 546.3146929 | 4 d | NS 1 mM VPA | 3.130802 | Unknown | |
| NS 1 mM VPA | 25.92929 | 556.13945 | 4 d | NS 1 mM VPA | 4.837329 | unknown | |
| NS 1 mM VPA | 25.92929 | 556.13945 | 2 d | NS 1 mM VPA | 5.293236 | unknown | |
| NS 1 mM VPA | 9.093727 | 575.1451545 | 4 d | NS 1 mM VPA | 2.795937 | Unknown | |
| NS 1 mM VPA | 9.093727 | 575.1451545 | 2 d | NS 1 mM VPA | 4.232054 | Unknown | |
| NS 1 mM VPA | 36.92372 | 575.3159222 | 2 d | NS 1 mM VPA | 2.816601 | Unknown | |
| NS 1 mM VPA | 36.92372 | 575.3159222 | 4 d | NS 1 mM VPA | 3.446719 | unknown | |
| NS 1 mM VPA | 80.9297 | 583.44194 | 2 d | NS 1 mM VPA | 1.503812 | Unknown | |
| NS 1 mM VPA | 80.9297 | 583.44194 | 4 d | NS 1 mM VPA | 4.532225 | Unknown | |
| NS 1 mM VPA | 4.824 | 594.2327 | 4 d | NS 1 mM VPA | 2.212473 | Unknown | |
| NS 1 mM VPA | 4.824 | 594.2327 | 2 d | NS 1 mM VPA | 4.279664 | Unknown | |
| NS 1 mM VPA | 41.278 | 632.232825 | 2 d | NS 1 mM VPA | 3.171377 | Unknown | |
| NS 1 mM VPA | 41.278 | 632.232825 | 4 d | NS 1 mM VPA | 4.764468 | Unknown | |
| NS 1 mM VPA | 14.97571 | 659.1506941 | 4 d | NS 1 mM VPA | 3.054219 | Unknown | |
| NS 1 mM VPA | 23.39707 | 660.1513786 | 2 d | NS 1 mM VPA | 3.542683 | Unknown | |
| NS 1 mM VPA | 23.39707 | 660.1513786 | 4 d | NS 1 mM VPA | 4.100844 | Unknown | |
| NS 1 mM VPA | 14.884 | 682.2853 | 2 d | NS 1 mM VPA | 2.823221 | Unknown | |
| NS 1 mM VPA | 14.884 | 682.2853 | 4 d | NS 1 mM VPA | 5.153298 | Unknown | |
| NS 1 mM VPA | 33.64471 | 822.2805429 | 2 d | NS 1 mM VPA | 2.668941 | Unknown | |
| NS 1 mM VPA | 33.64471 | 822.2805429 | 4 d | NS 1 mM VPA | 3.816104 | Unknown | |
| NS 1 mM VPA | 83.24742 | 907.54555 | 4 d | NS 1 mM VPA | 1.507945 | Unknown | |
| NS 1 mM VPA | 83.24742 | 907.54555 | 2 d | NS 1 mM VPA | 1.586431 | Unknown | |
| NS 1 mM VPA | 31.5316 | 908.22015 | 2 d | NS 1 mM VPA | 1.640148 | Unknown | |
| NS 1 mM VPA | 31.5316 | 908.22015 | 4 d | NS 1 mM VPA | 1.998983 | Unknown | |
| NS 1 mM VPA | 33.44333 | 1028.3246 | 2 d | NS 1 mM VPA | 5.833998 | Unknown | |
| NS 1 mM VPA | 33.44333 | 1028.3246 | 4 d | NS 1 mM VPA | 8.654592 | Unknown | |
| NS 1 mM VPA | 4.649125 | 1291.75965 | 2 d | NS 1 mM VPA | 1.739338 | beta-D-Glucosyl-1,4-N-acetyl-D-glucosaminyldiphosphoundecaprenol | |
| NS 1 mM VPA | 4.649125 | 1291.75965 | 4 d | NS 1 mM VPA | 1.793695 | beta-D-Glucosyl-1,4-N-acetyl-D-glucosaminyldiphosphoundecaprenol | |

TABLE 7

Cellular metabolites measured in hES cells treated with alcohol

| Experiment | Retention time | Mass | Time | Fold | p-value | Compound 1 | Compound 2 |
|---|---|---|---|---|---|---|---|
| ETOH 0.1 | 15.48433 | 99.0689 | 4 D | 1.434154 | 0.034571 | N-Methyl-2-pyrrolidinone | |
| ETOH 0.1 | 52.01225 | 99.1043 | 4 D | 2.703447 | 0.012638 | Unknown | |
| ETOH 0.1 | 13.40565 | 120.2112 | 4 D | 4.847027 | 0.029776 | Unknown | |
| ETOH 0.1 | 16.73904 | 129.0452 | 24 H | 1.502328 | 0.002871 | 3,4-Dihydroxybutyric acid | |
| ETOH 0.1 | 88.64043 | 130.9541 | 24 H | 1.631614 | 0.046779 | Unknown | |
| ETOH 0.1 | 22.22892 | 131.0746 | 24 H | −1.85703 | 0.037466 | 3-Methylindole | |
| ETOH 0.1 | 14.35336 | 131.076 | 4 D | 3.62907 | 0.014778 | Unknown | |
| ETOH 0.1 | 3.958833 | 148.0052 | 24 H | −1.94841 | 0.034059 | Unknown | |

TABLE 7-continued

Cellular metabolites measured in hES cells treated with alcohol

| Experiment | Retention time | Mass | Time | Fold | p-value | Compound 1 | Compound 2 |
|---|---|---|---|---|---|---|---|
| ETOH 0.1 | 52.88652 | 148.016 | 4 D | −2.44409 | 0.047122 | 2-Oxo-4-methylthiobutanoic acid | |
| ETOH 0.1 | 19.18355 | 168.0434 | 4 D | −1.46785 | 0.019426 | Homogentisic acid | Vanillic acid |
| ETOH 0.1 | 26.70635 | 171.1244 | 24 H | 2.376107 | 0.008413 | GABA analogue | |
| ETOH 0.1 | 22.17997 | 187.1343 | 24 H | 1.48782 | 0.045452 | (+/−)-2-(4'-Isobutylphenyl)propionitrile | |
| ETOH 0.1 | 46.31086 | 187.1348 | 4 D | 2.329144 | 4.21E−05 | (+/−)-2-(4'-Isobutylphenyl)propionitrile | |
| ETOH 0.1 | 5.935143 | 194.073 | 4 D | −1.38924 | 0.003217 | Phenanthrene-9,10-oxide | |
| ETOH 0.1 | 31.19917 | 195.124 | 4 D | −2.22499 | 0.004386 | Benzenemethanol, 2-(2-aminopropoxy)-3-methyl- | a-[1-(ethylamino)ethyl]-p-hydroxy-Benzyl alcohol |
| ETOH 0.1 | 38.99212 | 195.1253 | 4 D | 2.158606 | 0.00953 | Benzenemethanol, 2-(2-aminopropoxy)-3-methyl- | a-[1-(ethylamino)ethyl]-p-hydroxy-Benzyl alcohol |
| ETOH 0.1 | 48.37093 | 197.1769 | 4 D | −3.11904 | 0.016197 | Unknown | |
| ETOH 0.1 | 9.675726 | 203.1138 | 4 D | −1.70728 | 0.023636 | Acetylcarnitine | L-Glutamic acid n-butyl ester dimethylbutanamide |
| ETOH 0.1 | 6.747279 | 205.1304 | 4 D | −1.2578 | 0.005318 | Pantothenol | |
| ETOH 0.1 | 36.18938 | 210.0922 | 4 D | 1.864256 | 0.040527 | 3-(2,5-Dimethoxyphenylpropionic acid | |
| ETOH 0.1 | 24.52067 | 229.0949 | 24 H | −2.33044 | 0.008877 | Malonylcarnitine | |
| ETOH 0.1 | 17.7027 | 243.1089 | 4 D | −2.18071 | 0.016141 | Unknown | |
| ETOH 0.1 | 64.66999 | 266.1613 | 24 H | −1.51898 | 0.047652 | Unknown | |
| ETOH 0.1 | 42.3656 | 268.2487 | 4 D | −1.54971 | 0.015019 | Unknown | |
| ETOH 0.1 | 4.86619 | 271.9364 | 24 H | 2.629339 | 0.04245 | Unknown | |
| ETOH 0.1 | 43.99398 | 272.16 | 24 H | 1.929598 | 0.032191 | Unknown | |
| ETOH 0.1 | 43.99398 | 272.16 | 4 D | 2.186768 | 0.003018 | Unknown | |
| ETOH 0.1 | 63.00428 | 285.2285 | 24 H | 4.002774 | 0.018095 | Unknown | |
| ETOH 0.1 | 37.97297 | 292.1862 | 4 D | 2.239381 | 0.0496 | Unknown | |
| ETOH 0.1 | 4.014175 | 293.9773 | 4 D | 1.938848 | 0.036775 | Unknown | |
| ETOH 0.1 | 6.160071 | 294.0957 | 24 H | 1.269183 | 0.005089 | Unknown | |
| ETOH 0.1 | 8.967061 | 295.1521 | 4 D | 1.513407 | 0.042025 | Unknown | |
| ETOH 0.1 | 71.55535 | 296.2308 | 24 H | 3.545035 | 0.003758 | Unknown | |
| ETOH 0.1 | 50.75387 | 298.174 | 4 D | −3.00237 | 0.045113 | Unknown | |
| ETOH 0.1 | 18.88505 | 300.1147 | 4 D | 2.686262 | 0.023485 | Unknown | |
| ETOH 0.1 | 17.18696 | 300.1656 | 24 H | 1.548853 | 0.036582 | Unknown | |
| ETOH 0.1 | 7.719471 | 301.1345 | 4 D | 6.648828 | 0.030822 | Unknown | |
| ETOH 0.1 | 15.22357 | 312.1341 | 4 D | −2.01503 | 0.041156 | Unknown | |
| ETOH 0.1 | 26.51229 | 315.6732 | 4 D | 2.014609 | 0.010998 | Unknown | |
| ETOH 0.1 | 18.82373 | 325.2711 | 4 D | −1.75625 | 0.013853 | Unknown | |
| ETOH 0.1 | 20.94557 | 325.2714 | 4 D | −2.07426 | 0.00333 | Unknown | |
| ETOH 0.1 | 8.542672 | 337.2012 | 24 H | 1.402499 | 0.000372 | Unknown | |
| ETOH 0.1 | 3.85935 | 353.2765 | 4 D | 2.622059 | 0.002006 | Unknown | |
| ETOH 0.1 | 25.16993 | 357.1781 | 4 D | 2.217294 | 0.001346 | Unknown | |
| ETOH 0.1 | 24.01428 | 359.1532 | 4 D | 1.535704 | 0.033 | Unknown | |
| ETOH 0.1 | 18.50245 | 360.1321 | 4 D | 2.11023 | 0.004465 | Unknown | |
| ETOH 0.1 | 83.72506 | 362.2787 | 24 H | 2.819814 | 0.04795 | Unknown | |
| ETOH 0.1 | 83.72506 | 362.2787 | 4 D | 2.916423 | 0.023844 | Unknown | |
| ETOH 0.1 | 27.98054 | 368.2122 | 4 D | 1.69537 | 0.02565 | Unknown | |
| ETOH 0.1 | 20.76168 | 379.1771 | 24 H | −1.72285 | 0.021135 | Unknown | |
| ETOH 0.1 | 20.76168 | 379.1771 | 4 D | 1.539861 | 0.019592 | Unknown | |
| ETOH 0.1 | 15.20829 | 383.1721 | 4 D | 1.914543 | 0.043581 | Unknown | |
| ETOH 0.1 | 23.38956 | 384.2127 | 4 D | −2.55567 | 0.025704 | Unknown | |
| ETOH 0.1 | 51.65871 | 386.1724 | 4 D | 5.308852 | 0.032774 | (+)-Eudesmin | |
| ETOH 0.1 | 19.97914 | 387.0812 | 4 D | −1.97698 | 0.024641 | Unknown | |
| ETOH 0.1 | 19.97914 | 387.0812 | 24 H | 1.739051 | 0.018391 | Unknown | |
| ETOH 0.1 | 17.53242 | 388.1815 | 24 H | −1.44894 | 0.012322 | Unknown | |
| ETOH 0.1 | 46.346 | 388.2349 | 4 D | 1.946524 | 0.002762 | Unknown | |
| ETOH 0.1 | 15.90129 | 393.1889 | 24 H | −1.43098 | 0.022977 | Unknown | |
| ETOH 0.1 | 6.259963 | 396.1687 | 24 H | 1.717607 | 0.047952 | Unknown | |
| ETOH 0.1 | 51.66325 | 403.1978 | 4 D | 3.11601 | 0.048224 | Unknown | |
| ETOH 0.1 | 30.70733 | 405.2001 | 4 D | 2.668076 | 0.001676 | Unknown | |
| ETOH 0.1 | 16.21743 | 408.1636 | 4 D | 1.965641 | 0.028858 | Unknown | |
| ETOH 0.1 | 21.14975 | 417.2386 | 4 D | −1.97972 | 0.007183 | Unknown | |
| ETOH 0.1 | 33.09057 | 417.2338 | 4 D | 2.032563 | 0.016902 | Unknown | |
| ETOH 0.1 | 26.77212 | 420.1862 | 4 D | 3.282511 | 0.030236 | Unknown | |
| ETOH 0.1 | 18.03482 | 429.2533 | 4 D | −1.80751 | 0.006213 | Unknown | |
| ETOH 0.1 | 30.24237 | 429.2535 | 4 D | 1.804876 | 0.044332 | Unknown | |
| ETOH 0.1 | 35.58196 | 431.2501 | 4 D | 1.532408 | 0.037928 | Unknown | |
| ETOH 0.1 | 32.18393 | 437.2042 | 24 H | 24.53212 | 0.001124 | Unknown | |
| ETOH 0.1 | 4.808947 | 440.0223 | 4 D | −1.52785 | 0.03034 | Unknown | |
| ETOH 0.1 | 24.13915 | 443.2381 | 4 D | 2.985557 | 0.023682 | Unknown | |

TABLE 7-continued

Cellular metabolites measured in hES cells treated with alcohol

| Experiment | Retention time | Mass | Time | Fold | p-value | Compound 1 | Compound 2 |
|---|---|---|---|---|---|---|---|
| ETOH 0.1 | 67.0705 | 443.3216 | 4 D | 1.751997 | 0.037074 | Unknown | |
| ETOH 0.1 | 51.58546 | 444.2237 | 4 D | 2.130512 | 0.031074 | Unknown | |
| ETOH 0.1 | 33.51823 | 460.9391 | 4 D | −4.51805 | 0.005949 | Unknown | |
| ETOH 0.1 | 22.95657 | 462.2217 | 24 H | −1.98563 | 0.0437 | Unknown | |
| ETOH 0.1 | 25.3287 | 464.225 | 24 H | −1.63071 | 0.025852 | Unknown | |
| ETOH 0.1 | 46.51446 | 467.3804 | 4 D | 2.068091 | 0.042613 | Unknown | |
| ETOH 0.1 | 51.6158 | 468.2002 | 4 D | 1.875012 | 0.015762 | Unknown | |
| ETOH 0.1 | 30.37291 | 471.1928 | 4 D | 2.001387 | 0.022662 | glucuronide | |
| ETOH 0.1 | 30.72707 | 471.7804 | 4 D | −2.83569 | 0.037476 | Unknown | |
| ETOH 0.1 | 30.28867 | 478.2761 | 4 D | 1.698899 | 0.000475 | Unknown | |
| ETOH 0.1 | 72.7735 | 482.3062 | 24 H | −1.95925 | 0.042853 | Unknown | |
| ETOH 0.1 | 6.676207 | 485.2069 | 24 H | −2.01419 | 0.013732 | Unknown | |
| ETOH 0.1 | 66.73744 | 487.3472 | 4 D | 2.931014 | 0.007475 | Unknown | |
| ETOH 0.1 | 21.72729 | 489.2127 | 4 D | −1.51037 | 0.0314 | Unknown | |
| ETOH 0.1 | 31.22083 | 510.8202 | 4 D | 2.488196 | 0.011267 | Unknown | |
| ETOH 0.1 | 34.35986 | 521.9924 | 24 H | −1.44593 | 0.032994 | Unknown | |
| ETOH 0.1 | 34.57864 | 525.3161 | 4 D | 1.551324 | 0.037545 | Unknown | |
| ETOH 0.1 | 51.73057 | 526.2773 | 4 D | 3.445707 | 0.006877 | Unknown | |
| ETOH 0.1 | 23.87065 | 530.314 | 4 D | 1.964552 | 0.006366 | L-Oleandrosyl-oleandolide | |
| ETOH 0.1 | 32.50661 | 531.2876 | 4 D | 2.106138 | 0.024689 | Unknown | |
| ETOH 0.1 | 35.58454 | 531.3191 | 4 D | −1.25162 | 0.027019 | Unknown | |
| ETOH 0.1 | 66.31491 | 531.3736 | 4 D | 3.862674 | 0.01116 | Unknown | |
| ETOH 0.1 | 32.24719 | 541.3274 | 4 D | 2.161601 | 0.038319 | Unknown | |
| ETOH 0.1 | 17.6573 | 545.3029 | 4 D | −1.39484 | 0.043629 | Unknown | |
| ETOH 0.1 | 31.891 | 554.8471 | 4 D | 2.038489 | 0.037688 | Unknown | |
| ETOH 0.1 | 15.78741 | 555.2406 | 4 D | 1.835025 | 0.014923 | Unknown | |
| ETOH 0.1 | 5.742094 | 555.8505 | 4 D | −1.28922 | 0.017625 | Unknown | |
| ETOH 0.1 | 88.02533 | 556.3971 | 4 D | −3.11839 | 0.016192 | Unknown | |
| ETOH 0.1 | 31.97996 | 559.8329 | 4 D | −1.7213 | 0.049678 | Unknown | |
| ETOH 0.1 | 24.7039 | 574.3397 | 4 D | 1.58436 | 0.02116 | Unknown | |
| ETOH 0.1 | 31.71105 | 574.3427 | 4 D | 1.750055 | 0.026643 | Unknown | |
| ETOH 0.1 | 47.90467 | 576.096 | 4 D | 1.361314 | 0.021201 | Unknown | |
| ETOH 0.1 | 16.90923 | 577.2825 | 24 H | 1.727637 | 0.047154 | Unknown | |
| ETOH 0.1 | 35.26918 | 589.6938 | 4 D | 1.819573 | 0.027966 | Unknown | |
| ETOH 0.1 | 31.54325 | 591.3789 | 4 D | 1.578222 | 0.000714 | Unknown | |
| ETOH 0.1 | 25.14927 | 596.3543 | 4 D | 1.395808 | 0.049214 | L-Urobilinogen; | |
| ETOH 0.1 | 32.67372 | 603.3535 | 4 D | −2.62952 | 0.015253 | Unknown | |
| ETOH 0.1 | 8.056862 | 612.1509 | 24 H | −1.47366 | 0.02889 | Oxidized glutathione | Oxidized glutathione; Glutathione disulfide; GSSG; Oxiglutatione |
| ETOH 0.1 | 33.68866 | 619.3409 | 4 D | 1.856648 | 0.030722 | Unknown | |
| ETOH 0.1 | 32.73907 | 620.8861 | 4 D | 2.248558 | 0.00893 | Unknown | |
| ETOH 0.1 | 32.08734 | 635.4065 | 4 D | 1.392618 | 0.030885 | Unknown | |
| ETOH 0.1 | 5.903429 | 646.7084 | 4 D | −1.27147 | 0.020652 | Unknown | |
| ETOH 0.1 | 26.7452 | 661.3846 | 4 D | 1.295402 | 0.046573 | Unknown | |
| ETOH 0.1 | 33.48766 | 677.9101 | 24 H | −2.22083 | 0.028347 | Unknown | |
| ETOH 0.1 | 31.11764 | 693.4124 | 4 D | 2.318353 | 0.028562 | Unknown | |
| ETOH 0.1 | 28.2045 | 695.4286 | 24 H | −32.9384 | 0.027453 | Unknown | |
| ETOH 0.1 | 33.70266 | 699.9225 | 4 D | 1.719036 | 0.039493 | Unknown | |
| ETOH 0.1 | 40.84822 | 702.2497 | 4 D | −2.76945 | 0.001031 | Neu5Acalpha2-3Galbeta1-4Glcbeta-Sp | Neu5Acalpha2-6Galbeta1-4Glcbeta-Sp |
| ETOH 0.1 | 34.62439 | 707.3928 | 4 D | 2.136871 | 0.0353 | Unknown | |
| ETOH 0.1 | 56.18269 | 707.4296 | 24 H | 1.489574 | 0.046762 | Unknown | |
| ETOH 0.1 | 33.73428 | 708.9387 | 4 D | 2.159654 | 0.006959 | Unknown | |
| ETOH 0.1 | 4.826824 | 711.8344 | 24 H | −3.02053 | 0.013448 | Unknown | |
| ETOH 0.1 | 33.89008 | 730.4494 | 4 D | 2.613893 | 0.009133 | Unknown | |
| ETOH 0.1 | 47.76987 | 731.0954 | 4 D | −2.77579 | 0.004811 | Unknown | |
| ETOH 0.1 | 5.918027 | 732.007 | 4 D | 1.795393 | 0.021782 | Unknown | |
| ETOH 0.1 | 35.028 | 751.4193 | 4 D | 1.87008 | 0.032616 | Unknown | |
| ETOH 0.1 | 34.12668 | 752.4629 | 4 D | 2.066515 | 0.031345 | Unknown | |
| ETOH 0.1 | 69.32865 | 765.5211 | 24 H | 1.873064 | 0.033127 | Unknown | |
| ETOH 0.1 | 34.33545 | 774.4767 | 4 D | 2.103658 | 0.020363 | Unknown | |
| ETOH 0.1 | 89.29926 | 774.5055 | 4 D | −2.40077 | 0.006755 | Unknown | |
| ETOH 0.1 | 5.886782 | 780.241 | 4 D | −1.31403 | 0.025516 | Unknown | |
| ETOH 0.1 | 34.52749 | 796.4891 | 4 D | 1.926524 | 0.049615 | Unknown | |
| ETOH 0.1 | 34.60124 | 796.9917 | 4 D | 1.818186 | 0.015806 | Unknown | |
| ETOH 0.1 | 4.613879 | 820.8181 | 4 D | −1.47009 | 0.047535 | Unknown | |
| ETOH 0.1 | 5.259716 | 888.8041 | 4 D | −1.45771 | 0.021932 | Unknown | |
| ETOH 0.1 | 8.502051 | 909.5934 | 4 D | 2.274264 | 0.037836 | Unknown | |
| ETOH 0.1 | 5.217833 | 913.8074 | 24 H | −1.86064 | 0.028059 | Unknown | |
| ETOH 0.1 | 5.399211 | 921.0025 | 4 D | 1.677834 | 0.001526 | Unknown | |
| ETOH 0.1 | 3.646902 | 994.0917 | 24 H | 1.441829 | 0.019979 | Unknown | |
| ETOH 0.1 | 3.705141 | 1008.072 | 4 D | 1.30378 | 0.048393 | Unknown | |
| ETOH 0.1 | 5.177162 | 1038.786 | 4 D | 1.677834 | 0.030851 | Unknown | |

TABLE 7-continued

Cellular metabolites measured in hES cells treated with alcohol

| Experiment | Retention time | Mass | Time | Fold | p-value | Compound 1 | Compound 2 |
|---|---|---|---|---|---|---|---|
| ETOH 0.3 | 85.57399 | 83.0372 | 24 H | 2.472036 | 0.010882 | Unknown | |
| ETOH 0.3 | 15.48433 | 99.0689 | 4 D | 1.337742 | 0.043286 | N-Methyl-2-pyrrolidinone | |
| ETOH 0.3 | 15.48433 | 99.0689 | 24 H | 1.467845 | 0.043638 | N-Methyl-2-pyrrolidinone | |
| ETOH 0.3 | 52.01225 | 99.1043 | 24 H | 3.331103 | 0.000378 | Unknown | |
| ETOH 0.3 | 10.21225 | 101.1201 | 24 H | 2.191927 | 0.043209 | Hexylamine | |
| ETOH 0.3 | 4.032816 | 111.9839 | 4 D | −8.67642 | 0.018374 | Thiosulfate | |
| ETOH 0.3 | 3.767232 | 120.0436 | 4 D | 1.936297 | 0.034585 | 3,4-Dihydroxybutyric acid | |
| ETOH 0.3 | 13.40565 | 120.2112 | 4 D | 3.90007 | 0.046375 | Unknown | |
| ETOH 0.3 | 16.73904 | 129.0452 | 24 H | 1.795891 | 3.32E−05 | 3,4-Dihydroxybutyric acid | |
| ETOH 0.3 | 88.64043 | 130.9541 | 24 H | 2.024969 | 0.006982 | Unknown | |
| ETOH 0.3 | 22.22892 | 131.0746 | 4 D | 2.502205 | 0.049833 | 3-Methylindole | |
| ETOH 0.3 | 14.35336 | 131.076 | 4 D | 4.050219 | 0.020549 | Unknown | |
| ETOH 0.3 | 3.958833 | 148.0052 | 24 H | −1.72967 | 0.043053 | Unknown | |
| ETOH 0.3 | 7.479235 | 149.0511 | 4 D | −1.30477 | 0.014313 | Amino-4methylthiobutyric acid | |
| ETOH 0.3 | 27.80141 | 153.0811 | 24 H | −1.6976 | 0.025771 | Unknown | |
| ETOH 0.3 | 5.559732 | 155.0681 | 4 D | 1.637846 | 0.022817 | L-Histidine | 4-propionic acid |
| ETOH 0.3 | 14.22357 | 161.0805 | 24 H | −6.43527 | 0.032474 | Unknown | |
| ETOH 0.3 | 44.88033 | 162.0662 | 4 D | 1.799131 | 0.037703 | Unknown | |
| ETOH 0.3 | 23.6763 | 167.0941 | 24 H | −2.83 | 0.012984 | 3-Methoxytyramine | Phenylephrine |
| ETOH 0.3 | 19.18355 | 168.0434 | 4 D | 1.281914 | 0.028006 | Homogentisic acid | Vanillic acid |
| ETOH 0.3 | 26.70635 | 171.1244 | 24 H | 3.755227 | 0.001253 | GABA analogue | |
| ETOH 0.3 | 20.23014 | 173.084 | 24 H | −1.43983 | 0.019446 | 1,3-Dimethyl-8-isoquinolinol | |
| ETOH 0.3 | 28.52393 | 178.5546 | 24 H | −2.76389 | 0.001401 | Unknown | |
| ETOH 0.3 | 5.935143 | 194.073 | 4 D | −1.39988 | 0.002956 | Phenanthrene-9,10-oxide | 9-Hydroxyphenanthrene; 9-Phenanthrol |
| ETOH 0.3 | 22.61355 | 194.0836 | 24 H | −1.70303 | 0.030955 | Unknown | |
| ETOH 0.3 | 31.19917 | 195.124 | 4 D | −1.86013 | 0.015911 | Benzenemethanol, 2-(2-aminopropoxy)-3-methyl- | a-[1-(ethylamino)ethyl]-p-hydroxy-Benzyl alcohol |
| ETOH 0.3 | 19.48063 | 201.1709 | 4 D | −2.97874 | 0.009458 | Unknown | |
| ETOH 0.3 | 6.747279 | 205.1304 | 4 D | −1.33858 | 0.014168 | Pantothenol | dimethylbutanamide; |
| ETOH 0.3 | 36.18938 | 210.0922 | 4 D | 1.849968 | 0.042032 | 3-(2,5-Dimethoxy phenylpropionic acid | |
| ETOH 0.3 | 6.62669 | 218.0762 | 4 D | −1.77129 | 0.047105 | Unknown | |
| ETOH 0.3 | 27.57188 | 222.0401 | 24 H | −2.11155 | 0.040386 | Unknown | |
| ETOH 0.3 | 13.6845 | 223.119 | 24 H | −2.73967 | 0.024694 | Unknown | Unknown |
| ETOH 0.3 | 24.52067 | 229.0949 | 4 D | −1.74038 | 0.010344 | Malonylcarnitine | Malonylcarnitine |
| ETOH 0.3 | 55.50731 | 229.1457 | 4 D | −1.53336 | 0.028395 | Unknown | |
| ETOH 0.3 | 32.9941 | 229.2025 | 24 H | −1.37697 | 0.03113 | Unknown | |
| ETOH 0.3 | 47.0879 | 234.125 | 24 H | −1.63184 | 0.029169 | 5-Methoxytryptophan | |
| ETOH 0.3 | 53.26863 | 234.1253 | 4 D | −1.62383 | 0.026291 | 5-Methoxytryptophan | |
| ETOH 0.3 | 3.673694 | 237.0041 | 24 H | 2.989077 | 0.011016 | Unknown | |
| ETOH 0.3 | 5.176232 | 239.9592 | 24 H | 1.640005 | 0.018097 | Unknown | |
| ETOH 0.3 | 27.39631 | 243.11 | 4 D | −1.49547 | 0.024259 | Unknown | |
| ETOH 0.3 | 6.626769 | 247.1049 | 4 D | −4.47566 | 0.039425 | Unknown | |
| ETOH 0.3 | 9.0276 | 247.1408 | 4 D | −2.75089 | 0.000424 | Unknown | |
| ETOH 0.3 | 18.84552 | 256.1066 | 4 D | −2.14073 | 0.02288 | 5-Ethyl-5-(1-methyl-3-carboxypropyl)barbituric acid | |
| ETOH 0.3 | 40.75868 | 267.2543 | 4 D | −1.6481 | 0.029485 | Unknown | |
| ETOH 0.3 | 40.75868 | 267.2543 | 24 H | −1.49599 | 0.021245 | Unknown | |
| ETOH 0.3 | 42.3656 | 268.2487 | 4 D | −1.51708 | 0.030774 | Unknown | |
| ETOH 0.3 | 4.86619 | 271.9364 | 24 H | 4.069637 | 0.02742 | Unknown | |
| ETOH 0.3 | 22.86183 | 275.1193 | 24 H | −2.23674 | 0.044504 | Unknown | |
| ETOH 0.3 | 5.69776 | 284.9798 | 4 D | −1.2223 | 0.026683 | Unknown | |
| ETOH 0.3 | 14.88092 | 286.1519 | 4 D | −1.86167 | 0.033393 | Unknown | |
| ETOH 0.3 | 75.76147 | 288.2632 | 24 H | 1.96905 | 0.001271 | Unknown | |
| ETOH 0.3 | 66.86661 | 293.1952 | 4 D | −2.15382 | 0.004487 | Unknown | |
| ETOH 0.3 | 4.014175 | 293.9773 | 4 D | −2.26718 | 0.013307 | Unknown | |
| ETOH 0.3 | 20.67831 | 294.1535 | 4 D | −1.42237 | 0.008416 | Unknown | |
| ETOH 0.3 | 24.21651 | 294.1531 | 24 H | −1.89159 | 0.02267 | Unknown | |
| ETOH 0.3 | 8.967061 | 295.1521 | 4 D | 1.467032 | 0.021323 | Unknown | |
| ETOH 0.3 | 66.35884 | 298.1537 | 24 H | 3.758351 | 0.016783 | Unknown | |
| ETOH 0.3 | 19.66398 | 299.1929 | 24 H | −1.57058 | 0.041283 | Unknown | |
| ETOH 0.3 | 7.719471 | 301.1345 | 4 D | 2.678267 | 0.046654 | Unknown | |
| ETOH 0.3 | 4.954547 | 303.8875 | 24 H | 2.069669 | 0.049847 | Unknown | |
| ETOH 0.3 | 44.09424 | 313.199 | 24 H | 2.291989 | 0.005146 | Unknown | |
| ETOH 0.3 | 26.51229 | 315.6732 | 4 D | −2.86533 | 0.000573 | Unknown | |
| ETOH 0.3 | 23.90107 | 322.1166 | 4 D | −2.4215 | 0.010241 | Unknown | |
| ETOH 0.3 | 30.19245 | 324.1666 | 24 H | −1.59251 | 0.037632 | Unknown | |
| ETOH 0.3 | 20.72194 | 332.1367 | 4 D | −2.077 | 0.009795 | Unknown | |

TABLE 7-continued

Cellular metabolites measured in hES cells treated with alcohol

| Experiment | Retention time | Mass | Time | Fold | p-value | Compound 1 | Compound 2 |
|---|---|---|---|---|---|---|---|
| ETOH 0.3 | 8.542672 | 337.2012 | 24 H | 1.287435 | 0.004465 | Unknown | |
| ETOH 0.3 | 5.033976 | 340.9252 | 24 H | −1.83604 | 0.037709 | Unknown | |
| ETOH 0.3 | 5.033976 | 340.9252 | 4 D | 2.624968 | 0.049915 | Unknown | |
| ETOH 0.3 | 68.02448 | 342.1482 | 24 H | −1.85279 | 0.043066 | Unknown | |
| ETOH 0.3 | 3.85935 | 353.2765 | 4 D | 4.904139 | 0.000229 | Unknown | |
| ETOH 0.3 | 18.50245 | 360.1321 | 24 H | −2.28881 | 0.005116 | Unknown | |
| ETOH 0.3 | 83.72506 | 362.2787 | 24 H | −2.54153 | 0.005266 | Unknown | |
| ETOH 0.3 | 20.16372 | 365.1606 | 4 D | −1.92519 | 0.027055 | Unknown | |
| ETOH 0.3 | 11.47109 | 375.1898 | 4 D | 2.131693 | 0.028486 | Unknown | |
| ETOH 0.3 | 26.07722 | 375.1886 | 4 D | −4.75123 | 0.000746 | Unknown | |
| ETOH 0.3 | 41.28494 | 378.2956 | 24 H | 1.636485 | 0.027631 | Unknown | |
| ETOH 0.3 | 15.20829 | 383.1721 | 4 D | 3.377369 | 0.002214 | Unknown | |
| ETOH 0.3 | 51.65871 | 386.1724 | 4 D | 4.85106 | 0.031786 | (+)-Eudesmin | (+)-Eudesmin |
| ETOH 0.3 | 19.97914 | 387.0812 | 4 D | −1.69949 | 0.015257 | Unknown | |
| ETOH 0.3 | 46.346 | 388.2349 | 4 D | −1.53209 | 0.040255 | Unknown | |
| ETOH 0.3 | 15.90129 | 393.1889 | 24 H | −1.51089 | 0.011717 | Unknown | |
| ETOH 0.3 | 19.69092 | 393.1886 | 4 D | −2.05894 | 0.011258 | Unknown | |
| ETOH 0.3 | 6.259963 | 396.1687 | 4 D | 2.422002 | 0.013544 | Unknown | |
| ETOH 0.3 | 17.27421 | 403.1984 | 4 D | −2.30266 | 0.00281 | Unknown | |
| ETOH 0.3 | 21.14975 | 417.2386 | 4 D | −1.57309 | 0.03368 | Unknown | |
| ETOH 0.3 | 33.09057 | 417.2338 | 4 D | −1.77978 | 0.026439 | Unknown | |
| ETOH 0.3 | 13.35295 | 420.0513 | 4 D | −1.90198 | 0.003417 | Unknown | |
| ETOH 0.3 | 27.46219 | 421.2201 | 4 D | −2.27332 | 0.012803 | Unknown | |
| ETOH 0.3 | 18.03482 | 429.2533 | 4 D | −2.20091 | 0.002807 | Unknown | |
| ETOH 0.3 | 54.46495 | 440.0284 | 24 H | 2.51037 | 0.011972 | Unknown | |
| ETOH 0.3 | 30.87201 | 443.2339 | 4 D | 2.171362 | 0.0186 | Unknown | |
| ETOH 0.3 | 67.0705 | 443.3216 | 4 D | 1.688451 | 0.048544 | Unknown | |
| ETOH 0.3 | 51.58546 | 444.2237 | 24 H | 2.241866 | 0.044444 | Unknown | |
| ETOH 0.3 | 51.58546 | 444.2237 | 4 D | 2.030169 | 0.032667 | Unknown | |
| ETOH 0.3 | 30.05687 | 444.2789 | 24 H | −1.83503 | 0.021764 | Unknown | |
| ETOH 0.3 | 54.8719 | 446.0431 | 24 H | −2.22145 | 0.049006 | Unknown | |
| ETOH 0.3 | 54.8719 | 446.0431 | 4 D | 1.933882 | 0.047398 | Unknown | |
| ETOH 0.3 | 29.86415 | 447.2509 | 4 D | −1.85819 | 0.025964 | Unknown | |
| ETOH 0.3 | 29.86415 | 447.2509 | 24 H | 2.10322 | 0.036254 | Unknown | |
| ETOH 0.3 | 30.45343 | 449.2653 | 4 D | −2.41429 | 0.016795 | Unknown | |
| ETOH 0.3 | 44.98056 | 449.2611 | 24 H | −3.47136 | 0.038457 | Unknown | |
| ETOH 0.3 | 28.27806 | 455.2052 | 24 H | −2.50898 | 0.005338 | Unknown | |
| ETOH 0.3 | 33.51823 | 460.9391 | 4 D | −3.60151 | 0.010558 | Unknown | |
| ETOH 0.3 | 22.95657 | 462.2217 | 4 D | 1.935626 | 0.03474 | Unknown | |
| ETOH 0.3 | 33.5733 | 463.2914 | 24 H | −1.66521 | 0.034862 | Unknown | |
| ETOH 0.3 | 25.3287 | 464.225 | 24 H | −1.71665 | 0.033532 | Unknown | |
| ETOH 0.3 | 30.46172 | 466.2921 | 24 H | −1.95938 | 0.012601 | Unknown | |
| ETOH 0.3 | 33.68894 | 466.615 | 24 H | −3.27865 | 0.008212 | Unknown | |
| ETOH 0.3 | 46.51446 | 467.3804 | 24 H | −2.13465 | 0.013009 | Unknown | |
| ETOH 0.3 | 51.6158 | 468.2002 | 4 D | 1.919859 | 0.003122 | Unknown | |
| ETOH 0.3 | 30.37291 | 471.1928 | 4 D | 2.725649 | 0.008164 | glucuronide | |
| ETOH 0.3 | 30.72707 | 471.7804 | 4 D | −3.44069 | 0.010281 | Unknown | |
| ETOH 0.3 | 30.28867 | 478.2761 | 4 D | 1.509949 | 0.018484 | Unknown | |
| ETOH 0.3 | 10.82859 | 482.1942 | 24 H | −1.52795 | 0.033711 | Unknown | |
| ETOH 0.3 | 72.7735 | 482.3062 | 24 H | −2.61806 | 0.0161 | Unknown | |
| ETOH 0.3 | 10.8217 | 485.204 | 24 H | 2.038065 | 0.038466 | Unknown | |
| ETOH 0.3 | 66.73744 | 487.3472 | 4 D | 2.877867 | 0.020235 | Unknown | |
| ETOH 0.3 | 30.83472 | 488.305 | 24 H | −2.18525 | 0.009407 | Unknown | |
| ETOH 0.3 | 30.88032 | 488.8071 | 24 H | −1.91959 | 0.040672 | Unknown | |
| ETOH 0.3 | 21.72729 | 489.2127 | 4 D | 2.372158 | 0.000369 | Unknown | |
| ETOH 0.3 | 13.78553 | 502.2258 | 4 D | 1.866325 | 0.010364 | Unknown | |
| ETOH 0.3 | 18.36887 | 505.2616 | 4 D | 2.008892 | 0.036368 | Unknown | |
| ETOH 0.3 | 5.891069 | 509.6704 | 4 D | 1.467845 | 0.0228 | Unknown | |
| ETOH 0.3 | 31.20706 | 510.3182 | 24 H | −2.26373 | 0.006715 | Unknown | |
| ETOH 0.3 | 31.22083 | 510.8202 | 24 H | −2.04514 | 0.041219 | Unknown | |
| ETOH 0.3 | 31.22083 | 510.8202 | 4 D | 2.502378 | 0.010461 | Unknown | |
| ETOH 0.3 | 46.57666 | 518.3914 | 4 D | 2.288814 | 0.002533 | Unknown | |
| ETOH 0.3 | 46.57666 | 518.3914 | 24 H | −2.70682 | 0.017765 | Unknown | |
| ETOH 0.3 | 34.35986 | 521.9924 | 24 H | −1.58403 | 0.024454 | Unknown | |
| ETOH 0.3 | 31.53434 | 523.8187 | 24 H | −2.17272 | 0.02888 | Unknown | |
| ETOH 0.3 | 51.73057 | 526.2773 | 4 D | 2.714525 | 0.010415 | Unknown | |
| ETOH 0.3 | 71.36012 | 528.3631 | 4 D | 2.361003 | 0.026297 | Unknown | |
| ETOH 0.3 | 23.87065 | 530.314 | 4 D | 2.211921 | 0.001298 | L-Oleandrosyl-oleandolide | |
| ETOH 0.3 | 32.50661 | 531.2876 | 4 D | 2.36084 | 0.014947 | Unknown | |
| ETOH 0.3 | 35.58454 | 531.3191 | 4 D | −3.0409 | 0.000281 | Unknown | |
| ETOH 0.3 | 66.31491 | 531.3736 | 4 D | 2.87388 | 0.031879 | Unknown | |
| ETOH 0.3 | 31.58889 | 532.8335 | 24 H | −2.16926 | 0.015971 | Unknown | |
| ETOH 0.3 | 51.52268 | 539.4374 | 24 H | −1.92987 | 0.031525 | Unknown | |
| ETOH 0.3 | 32.24719 | 541.3274 | 24 H | −2.12255 | 0.01445 | Unknown | |
| ETOH 0.3 | 31.8519 | 554.3444 | 24 H | −2.36953 | 0.00655 | Unknown | |

TABLE 7-continued

Cellular metabolites measured in hES cells treated with alcohol

| Experiment | Retention time | Mass | Time | Fold | p-value | Compound 1 | Compound 2 |
|---|---|---|---|---|---|---|---|
| ETOH 0.3 | 31.891 | 554.8471 | 24 H | −2.29708 | 0.010734 | Unknown | |
| ETOH 0.3 | 15.78741 | 555.2406 | 4 D | 2.470837 | 0.001092 | Unknown | |
| ETOH 0.3 | 5.742094 | 555.8505 | 4 D | −1.3396 | 0.023948 | Unknown | |
| ETOH 0.3 | 5.742094 | 555.8505 | 24 H | −1.51803 | 0.031838 | Unknown | |
| ETOH 0.3 | 88.02533 | 556.3971 | 4 D | −2.38386 | 0.035829 | Unknown | |
| ETOH 0.3 | 31.97996 | 559.8329 | 4 D | −2.56596 | 0.002155 | Unknown | |
| ETOH 0.3 | 14.9927 | 566.2265 | 4 D | 1.624054 | 0.006806 | Unknown | |
| ETOH 0.3 | 24.7039 | 574.3397 | 4 D | 1.523934 | 0.011558 | Unknown | |
| ETOH 0.3 | 47.90467 | 576.096 | 4 D | 1.557573 | 0.020904 | Unknown | |
| ETOH 0.3 | 32.15777 | 576.3582 | 24 H | −2.20886 | 0.012421 | Unknown | |
| ETOH 0.3 | 16.90923 | 577.2825 | 4 D | −8.91726 | 0.02781 | Unknown | |
| ETOH 0.3 | 5.903169 | 579.2519 | 4 D | −2.11184 | 0.001075 | Ethanesulfonic acid | |
| ETOH 0.3 | 5.903169 | 579.2519 | 24 H | −1.48021 | 0.01083 | Ethanesulfonic acid | |
| ETOH 0.3 | 31.54325 | 591.3789 | 24 H | −1.98165 | 0.010883 | Unknown | |
| ETOH 0.3 | 25.14927 | 596.3543 | 4 D | 1.545421 | 0.015277 | L-Urobilinogen; | |
| ETOH 0.3 | 25.14927 | 596.3543 | 24 H | 1.834898 | 0.021555 | L-Urobilinogen; | |
| ETOH 0.3 | 32.67372 | 603.3535 | 4 D | −2.93997 | 0.007904 | Unknown | |
| ETOH 0.3 | 56.3513 | 611.4952 | 24 H | −1.9811 | 0.007557 | Unknown | |
| ETOH 0.3 | 4.936704 | 611.8727 | 4 D | 2.009588 | 0.018619 | Unknown | |
| ETOH 0.3 | 32.70236 | 611.871 | 24 H | −2.19208 | 0.044039 | Unknown | |
| ETOH 0.3 | 8.056862 | 612.1509 | 24 H | −1.59538 | 0.010611 | Oxidized glutathione | |
| ETOH 0.3 | 33.68866 | 619.3409 | 4 D | 2.125939 | 0.015211 | Unknown | |
| ETOH 0.3 | 32.73907 | 620.8861 | 24 H | −2.32076 | 0.039661 | Unknown | |
| ETOH 0.3 | 32.08734 | 635.4065 | 4 D | 1.394744 | 0.031645 | Unknown | |
| ETOH 0.3 | 32.95522 | 642.397 | 24 H | −2.21146 | 0.035834 | Unknown | |
| ETOH 0.3 | 5.903429 | 646.7084 | 4 D | 2.946495 | 2.66E−05 | Unknown | |
| ETOH 0.3 | 8.787827 | 658.2544 | 4 D | −3.20961 | 0.030138 | Unknown | |
| ETOH 0.3 | 26.7452 | 661.3846 | 4 D | 1.546707 | 0.010714 | Unknown | |
| ETOH 0.3 | 16.3338 | 666.3836 | 24 H | −1.37135 | 0.037278 | Unknown | |
| ETOH 0.3 | 33.48766 | 677.9101 | 24 H | −2.64653 | 0.009907 | Unknown | |
| ETOH 0.3 | 40.84822 | 702.2497 | 24 H | 1.283337 | 0.019733 | Neu5Acalpha2-3Galbeta1-4Glcbeta-Sp | |
| ETOH 0.3 | 40.84822 | 702.2497 | 4 D | −2.21591 | 0.004389 | Neu5Acalpha2-3Galbeta1-4Glcbeta-Sp | |
| ETOH 0.3 | 30.43889 | 707.3933 | 24 H | −1.79166 | 0.048232 | Unknown | |
| ETOH 0.3 | 56.18269 | 707.4296 | 24 H | −2.43361 | 0.009442 | Unknown | |
| ETOH 0.3 | 4.826824 | 711.8344 | 24 H | −2.25605 | 0.017007 | Unknown | |
| ETOH 0.3 | 47.76987 | 731.0954 | 4 D | −3.25036 | 0.027339 | Unknown | |
| ETOH 0.3 | 5.918027 | 732.007 | 4 D | 1.76125 | 0.038454 | Unknown | |
| ETOH 0.3 | 35.028 | 751.4193 | 24 H | −1.70279 | 0.045682 | Unknown | |
| ETOH 0.3 | 35.028 | 751.4193 | 4 D | 1.845101 | 0.0375 | Unknown | |
| ETOH 0.3 | 69.32865 | 765.5211 | 24 H | 1.884393 | 0.027105 | Unknown | |
| ETOH 0.3 | 34.33545 | 774.4767 | 24 H | −2.34161 | 0.036388 | Unknown | |
| ETOH 0.3 | 34.60124 | 796.9917 | 4 D | 1.688919 | 0.047852 | Unknown | |
| ETOH 0.3 | 4.613879 | 820.8181 | 24 H | −1.85112 | 0.038895 | Unknown | |
| ETOH 0.3 | 4.613879 | 820.8181 | 4 D | −1.57113 | 0.014605 | Unknown | |
| ETOH 0.3 | 5.259716 | 888.8041 | 24 H | 1.221624 | 0.043348 | Unknown | |
| ETOH 0.3 | 5.217833 | 913.8074 | 24 H | −1.88465 | 0.026148 | Unknown | |
| ETOH 0.3 | 5.399211 | 921.0025 | 4 D | 1.944905 | 2.78E−05 | Unknown | |
| ETOH 0.3 | 5.387775 | 922.0048 | 24 H | −2.75471 | 0.015691 | Unknown | |
| ETOH 0.3 | 3.680188 | 980.075 | 4 D | 1.480926 | 0.012893 | Unknown | |
| ETOH 0.3 | 3.646902 | 994.0917 | 4 D | 1.604696 | 0.000395 | Unknown | |
| ETOH 0.3 | 3.705141 | 1008.072 | 4 D | 1.415783 | 0.021503 | Unknown | |
| ETOH 0.3 | 5.177162 | 1038.786 | 4 D | 1.588208 | 0.030971 | Unknown | |
| ETOH 0.3 | 5.8905 | 1040.323 | 4 D | −1.47887 | 0.009656 | Unknown | |

All references cited herein are incorporated by reference. In addition, the invention is not intended to be limited to the disclosed embodiments of the invention. It should be understood that the foregoing disclosure emphasizes certain specific embodiments of the invention and that all modifications or alternatives equivalent thereto are within the spirit and scope of the invention as set forth in the appended claims.

What is claimed is:

1. A method for identifying one or a plurality of cellular metabolites having a molecular weight of from about 10 to about 1500 Daltons that is differentially produced in human embryonic stem cells (hESCs) or human pluripotent stem cells contacted with a test compound from a population of secreted cellular metabolites, the method comprising the steps of:

a) culturing hESCs or human pluripotent stem cells in the presence or absence of a test compound;

b) separating members of the population of cellular metabolites having a molecular weight of from about 10 to about 1500 Daltons that are secreted from hESCs or human pluripotent stem cells;

c) detecting one or a plurality of differentially produced cellular metabolites having a molecular weight of from about 10 to about 1500 Daltons from hESCs or human pluripotent stem cells; and d) identifying at least one cellular metabolite having a molecular weight of from about 10 to about 1500 Daltons that is differentially produced in cells cultured in the presence of the test compound.

2. A method according to claim 1, wherein at least one of the cellular metabolites is produced in greater amounts in the presence of the test compound than in the absence of the test compound.

3. A method according to claim 1, wherein at least one of the cellular metabolites is produced in greater amounts in the absence of the test compound than in the presence of the test compound.

4. A method according to claim 1, wherein the cellular metabolite has a molecular weight of from about 100 to about 1000 Daltons.

5. A method according to claim 1, wherein the test compound is a toxic or teratogenic compound.

6. A method according to claim 1, wherein one or a plurality of cellular metabolites is separated using a physical separation method.

7. A method according to claim 6, wherein the physical separation method is liquid chromatography/electrospray ionization time of flight mass spectrometry.

8. A method according to claim 1, wherein the cellular metabolites are tetrahydrofolate, dihydrofolate or other metabolites in the folate metabolic pathway, glutathione, or oxidized glutathione.

9. A method according to claim 1, wherein the cellular metabolites are kynurenine, 8-methoxykynurenate, N'-formylkynurenine 7,8-dihydro-7,8-dihydroxykynurenate, 5-Hydroxytryptophan, N-acetyl-D-tryptophan, glutamate, pyroglutamic acid or other metabolites in the tryptophan or glutamate metabolic pathways, histamine, dopamine, 3,4-dihydroxybutyric acid, serotonin, or gamma-aminobutyric acid (GABA).

10. A method according to claim 1, wherein a plurality of cellular metabolites are identified.

11. A method according to claim 10 wherein the plurality of identified cellular metabolites comprise a biomarker profile.

12. A method according to claim 11, wherein one of the cellular metabolites comprising a biomarker profile is kynurenine.

13. A method according to claim 10, wherein the test compound is a toxic or teratogenic compound.

14. A method according to claim 13, wherein the plurality of identified cellular metabolites comprise a biomarker profile characteristic of hESC or human pluripotent stem cell response to a toxic or teratogenic compound.

15. A method of claim 1, further comprising the step of identifying at least one cellular metabolite having a molecular weight of from about 10 to about 1500 Daltons that is differentially produced in the cells in the presence or absence of the test compound in a biomarker profile comprising one or a plurality of cellular metabolites having a molecular weight of from about 10 to about 1500 Daltons that are differentially produced in human embryonic stem cells (hESCs) or human pluripotent stem cells contacted with a toxic compound or compounds.

16. The method of claim 1, wherein at least two cellular metabolites having a molecular weight of from about 10 to about 1500 Daltons that are differentially produced in the cells in the presence or absence of the test compound are detected.

17. A method for screening a test compound to identify an effect of the compound on human embryonic stem cells (hESCs) or human pluripotent stem cells contacted with the test compound, the method comprising the steps of:
 a) culturing hESCs or human pluripotent stem cells in the presence or absence of a test compound;
 b) separating members of a population of cellular metabolites having a molecular weight of from about 10 to about 1500 Daltons that are secreted from hESCs or human pluripotent stem cells
 c) detecting one or a plurality of differentially produced cellular metabolites having a molecular weight of from about 10 to about 1500 Daltons; and
 d) identifying the effect of a compound on human embryonic stem cells (hESCs) or human pluripotent stem cells by identifying at least one cellular metabolite having a molecular weight of from about 10 to about 1500 Daltons that is differentially secreted between cells cultured in the presence versus the absence of the test compound.

18. A method according to claim 17, wherein at least one of the cellular metabolites is produced in greater amounts in the presence of the test compound than in the absence of the test compound.

19. A method according to claim 17, wherein at least one of the cellular metabolites is produced in greater amounts in the absence of the test compound than in the presence of the test compound.

20. A method according to claim 17, wherein at least one of the cellular metabolites has a molecular weight of from about 100 to about 1000 Daltons.

21. A method according to claim 17, wherein the test compound is a toxic or teratogenic compound.

22. A method according to claim 17, wherein one or a plurality of cellular metabolites is separated using a physical separation method.

23. A method according to claim 22, wherein the physical separation method is liquid chromatography/electrospray ionization time of flight mass spectrometry.

24. A method according to claim 17, wherein the cellular metabolites are tetrahydrofolate, dihydrofolate or other metabolites in the folate metabolic pathway, glutathione, or oxidized glutathione.

25. A method according to claim 17, wherein the cellular metabolites are kynurenine, 8-methoxykynurenate, N'-formylkynurenine 7,8-dihydro-7,8-dihydroxykynurenate, 5-Hydroxytryptophan, N-acetyl-D-tryptophan, glutamate, pyroglutamic acid or other metabolites in the tryptophan or glutamate metabolic pathways, histamine, dopamine, serotonin, gamma-aminobutyric acid (GABA) or other butyric acid species.

26. A method according to claim 17 wherein a plurality of cellular metabolites are identified.

27. A method according to claim 26, wherein the plurality of identified cellular metabolites comprise a biomarker profile.

28. A method according to claim 27, wherein one of the cellular metabolites comprising a biomarker profile is kynurenine.

29. A method according to claim 27, wherein the test compound is a toxic or teratogenic compound.

30. A method according to claim 29, wherein the plurality of identified cellular metabolites comprise a biomarker profile characteristic of hESC or human pluripotent stem cells response to a toxic or teratogenic compound.

31. A method of claim 17, further comprising the step of identifying at least one cellular metabolite having a molecular weight of from about 10 to about 1500 Daltons that is differentially produced in the cells in the presence or absence of the test compound in biomarker profile comprising one or a plurality of cellular metabolites having a molecular weight of from about 10 to about 1500 Daltons that are differentially produced in human embryonic stem cells (hESCs) or human pluripotent stem cells contacted with a toxic compound or compounds.

32. The method of claim 17, wherein at least two cellular metabolites having a molecular weight of from about 10 to about 1500 Daltons that are differentially produced in the cells in the presence or absence of the test compound are detected.

33. A method for assaying a test compound for toxicity or teratogenicity to hESC-derived lineage-specific cells or human pluripotent stem cell-derived lineage-specific cells contacted with the test compound, the method comprising the steps of:
 a) culturing hESC-derived lineage-specific cells or human pluripotent stem cell-derived lineage-specific cells in the presence or absence of a test compound;
 b) separating members of a population of cellular metabolites having a molecular weight of from about 10 to about 1500 Daltons secreted from or hESC-derived lineage-specific cells or human pluripotent stem cell-derived lineage-specific cells;
 c) detecting one or a plurality of cellular metabolites having a molecular weight of from about 10 to about 1500 Daltons produced by hESC-derived lineage-specific cells or human pluripotent stem cell-derived lineage-specific cells contacted with a compound; and
 d) identifying the toxicity or teratogenicity of the test compounds wherein hESC-derived lineage-specific cells or human pluripotent stem cell-derived lineage-specific cells contacted with a test compound differentially produce one or a plurality of cellular metabolites having a molecular weight of from about 10 to about 1500 Daltons.

34. A method according to claim 33, wherein at least one of the cellular metabolites is produced in greater amounts in the presence of the test compound than in the absence of the test compound.

35. A method according to claim 33, wherein at least one of the cellular metabolites is produced in greater amounts in the absence of the test compound than in the presence of the test compound.

36. A method according to claim 33, wherein the cellular metabolite has a molecular weight of from about 100 to about 1000 Daltons.

37. A method according to claim 33, wherein the test compound is a toxic or teratogenic compound.

38. A method according to claim 33, wherein one or a plurality of cellular metabolites is separated using a physical separation method.

39. A method according to claim 38, wherein the physical separation method is liquid chromatography/electrospray ionization time of flight mass spectrometry.

40. A method according to claim 33, wherein the cellular metabolites are tetrahydrofolate, dihydrofolate or other metabolites in the folate metabolic pathway, glutathione, or oxidized glutathione.

41. A method according to claim 33, wherein the cellular metabolites are kynurenine, 8-methoxykynurenate, N'-formylkynurenine 7,8-dihydro-7,8-dihydroxykynurenate 5-Hydroxytryptophan, N-acetyl-D-tryptophan, glutamate, pyroglutamic acid or other metabolites in the tryptophan or glutamate metabolic pathways, histamine, dopamine, 3,4-dihydroxybutyric acid, serotonin, gamma-aminobutyric acid (GABA) or other butyric acid species.

42. A method according to claim 33, wherein a plurality of cellular metabolites are identified.

43. A method according to claim 42, wherein the plurality of identified cellular metabolites comprise a biomarker profile.

44. A method according to claim 43, wherein one of the cellular metabolites comprising a biomarker profile is kynurenine.

45. A method according to claim 44, wherein the test compound is a toxic or teratogenic compound.

46. A method according to claim 33, wherein the plurality of identified cellular metabolites comprise a biomarker profile characteristic of hESC response to a toxic or teratogenic compound.

47. A method of claim 33, further comprising the step of identifying at least one cellular metabolite having a molecular weight of from about 10 to about 1500 Daltons that is differentially produced in the cells in the presence or absence of the test compound in a biomarker profile comprising one or a plurality of cellular metabolites having a molecular weight of from about 10 to about 1500 Daltons that are differentially produced in hESC-derived lineage-specific cells or human pluripotent stem cell-derived lineage-specific cells contacted with a toxic compound or compounds.

48. The method of claim 33, wherein at least two cellular metabolites having a molecular weight of from about 10 to about 1500 Daltons that are differentially produced in the cells in the presence or absence of the test compound are detected.

* * * * *